US008691753B2

(12) United States Patent
Devel et al.

(10) Patent No.: US 8,691,753 B2
(45) Date of Patent: Apr. 8, 2014

(54) PSEUDODIPEPTIDES AS MMP INHIBITORS

(75) Inventors: Laurent Devel, Malakoff (FR); Fabrice Beau, Massy (FR); Bertrand Czarny, Malakoff (FR); Vincent Dive, Palaiseau (FR)

(73) Assignee: Commissariat A l'Energie Atomique et Aux Energies Alternatives, Paris (FR)

( * ) Notice: Subject to any disclaimer, the term of this patent is extended or adjusted under 35 U.S.C. 154(b) by 0 days.

(21) Appl. No.: 13/392,358

(22) PCT Filed: Aug. 26, 2010

(86) PCT No.: PCT/FR2010/000581
§ 371 (c)(1),
(2), (4) Date: Apr. 18, 2012

(87) PCT Pub. No.: WO2011/023864
PCT Pub. Date: Mar. 3, 2011

(65) Prior Publication Data
US 2012/0309674 A1 Dec. 6, 2012

(30) Foreign Application Priority Data
Aug. 26, 2009 (FR) ..................................... 09 04061

(51) Int. Cl.
| | | |
|---|---|---|
| *A61K 38/00* | (2006.01) | |
| *A61P 9/10* | (2006.01) | |
| *C07K 14/47* | (2006.01) | |
| *C07D 409/00* | (2006.01) | |

(52) U.S. Cl.
USPC ......... 514/1.9; 514/21.9; 514/21.91; 546/213

(58) Field of Classification Search
None
See application file for complete search history.

(56) References Cited

U.S. PATENT DOCUMENTS

| 5,595,756 A * | 1/1997 | Bally et al. .................... 424/450 |
| 2003/0129672 A1 | 7/2003 | Dyer et al. |
| 2008/0194565 A1 | 8/2008 | Palle et al. |

FOREIGN PATENT DOCUMENTS

WO  2006 090235  8/2006

OTHER PUBLICATIONS

Sporn et at., Chemoprevention of Cancer, Carcinogenesis, 2000, vol. 21, 525-530.*
Auerbach et al., Cancer and Metastasis Reviews, 2000, 19, pp. 167-172.*
Gura, Science, 1997, 278 (5340): 1041-1042, encloses 1-5.*
Jain, Scientific American, Jul. 1994, 58-65.*
Cancer Druq Design and Discovery Neidle, Stephen, ed. (Elsevier/Academic Press, 2008) p. 431.*
Devel, L., et al., "Development of Selective Inhibitors and Substrate of Matrix Metalloproteinase-12," The Journal of Biological Chemistry, vol. 281, No. 16, pp. 11152-11160, (Apr. 21, 2006) XP002581157.
Dixon, S. M., et al., "Slow-Binding Human Serine Racemase Inhibitors from High-Throughput Screening of Combinatorial Libraries," Journal of Medicinal Chemistry, vol. 49, No. 8, pp. 2388-2397, (Mar. 21, 2006) XP002581158.
Dabert-Gay, A-S., et al., "Molecular Determinants of Matrix Metalloproteinase-12 Covalent Modification by a Photoaffinity Probe," The Journal of Biological Chemistry, vol. 283, No. 45, pp. 31058-31067, (Nov. 7, 2008) XP002615480.
Faust, A., et al., "Synthesis and Evaluation of a Novel Hydroxamate Based Fluorescent Photoprobe for Imaging of Matrix Metalloproteinases," Bioconjugate Chemistry, vol. 20, No. 5, pp. 904-912, (Apr. 17, 2009) XP002615481.
International Search Report Issued Jan. 14, 2011 in PCT/FR10/000581 Filed Aug. 26, 2010.

* cited by examiner

*Primary Examiner* — Marcela M Cordero Garcia
*Assistant Examiner* — Kaipeen Yang
(74) *Attorney, Agent, or Firm* — Oblon, Spivak, McClelland, Maier & Neustadt, L.L.P.

(57) ABSTRACT

The invention relates to compounds, in particular MMP inhibitors. The compounds of the invention have formula (1). The invention can be used in particular in the pharmaceutical field. The present invention also relates to labeled compounds of formula (2), and to the use thereof as contrast agents for detecting extracellular matrix metalloproteinases.

25 Claims, No Drawings

SEQUENCE LISTING

```
<160> NUMBER OF SEQ ID NOS: 1

<210> SEQ ID NO 1
<211> LENGTH: 8
<212> TYPE: PRT
<213> ORGANISM: artificial sequence
<220> FEATURE:
<223> OTHER INFORMATION: fragment of the consensus sequence of the TAG
      label

<400> SEQUENCE: 1

Arg Arg Met Gln Tyr Asn Arg Arg
1               5
```

PSEUDODIPEPTIDES AS MMP INHIBITORS

The invention relates to pseudodipeptide derivatives and to uses thereof in particular as inhibitors of metalloproteinases belonging to the family of zinc metalloproteinases, extracellular matrix metalloproteinases or MMPs, and also to labeled pseudopeptides derivatives and to uses thereof as contrast agents for detecting MMPs in active form.

It also relates to a pharmaceutical composition comprising these derivatives.

In humans, extracellular matrix metalloproteinases or MMPs represent a family of 23 members. All these members are very close from a structural point of view and are collectively capable of hydrolyzing all the protein components of the extracellular matrix (Brinckerhoff et al, 2002 Nat Rev Mol Cell Biol (1)).

Thus, this proteinase family has been implicated in all processes requiring tissue remodeling and associated cell movements (Page-McCaw et al, 2007 Nat Rev Mol Cell Biol (2)), which are the common characteristics observed in many human diseases such as cancer.

However, in the last ten years, the spectrum of proteins which can be hydrolyzed by MMPs has become much broader.

In fact, it now appears that these proteinases can also hydrolyze proteins which do not belong to the extracellular matrix, such as chemokines or cytokines, but also certain growth factor receptors, to mention but a few (Egeblad et al. 2002 Nat Rev cancer (3)).

This broad spectrum of activities has led to MMPs being considered as therapeutic targets in a vast range of human pathological conditions (Fingleton et al., 2007 Curr Pharm Des (4), and Hu et al. 2007 Nat Drug Dis (5)).

In the past, MMP inhibitors have mainly been evaluated in the treatment of cancer diseases (Overall et al., 2002 Nat Rev Cancer (6)).

However, these clinical trials have been disappointing, mainly because the inhibitors selected for this application were nonselective with respect to MMPs, i.e. they could block all MMPs with the same efficacy.

As it happens, at the current time, the therapeutic applications for MMP inhibitors are mainly centered on compounds which have a high selectivity profile, i.e. inhibitors capable of blocking only some MMPs or even better still just one MMP.

These inhibitors are called highly selective MMP inhibitors.

In particular, powerful and selective inhibitors of MMP-12 have been sought since this MMP is considered to be involved in numerous inflammatory diseases, in particular chronic obstructive pulmonary disease (COPD).

MMP-12 is also found to be implicated in human pathological conditions such as arthritis, rhumatoid arthritis, atherosclerosis and ruptured aneurysms.

Furthermore, an increase in MMP-12 expression in several human cancers has also been reported, suggesting a possible therapeutic application for MMP-12 inhibitors in certain cancers.

MMP-12 is also called "macrophage elastase".

Compounds which have a relatively good selectivity profile in favor of MMP-12 have been described, in particular in international application WO 2008/057254.

The chemical structure of these compounds is characterized by the presence of an alkyl carboxylate group, the function of which is to interact with the zinc atom present in the active site of all MMPs.

One of the compounds described has the following structure:

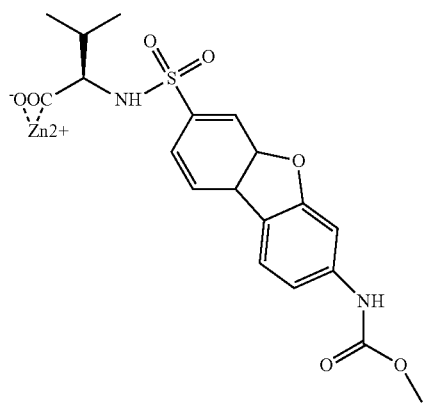

Devel et al. have reported the first example of a very powerful and very selective inhibitor of MMP-12, in J. Biol. Chem. 2006 (7).

This compound has the following formula:

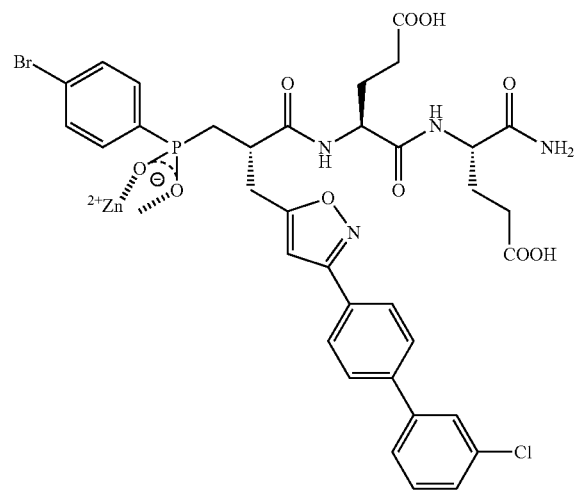

This compound, referred to hereinafter as RXP470, has an inhibition constant Ki value of 0.4 nM for human MMP-12 and is two to three orders of magnitude less powerful toward MMPs 1, 2, 3, 7, 8, 9, 11, 13 and 14.

Once again, the chemical structure of this inhibitor is characterized by the presence of a group, in this case a phosphoryl group, the function of which is to interact with the zinc atom of the active sites of the MMPs.

However, the presence of the negatively charged phosphoryl group ($PO_2^-$) in inhibitors of this type limits their crossing of the intestinal barrier and therefore prevents oral administration thereof.

MMP inhibitors, and in particular MMP-12 inhibitors, have therefore been sought which do not incorporate into their structures chemical groups capable of interacting with the zinc atom of the active site of MMPs.

The most encouraging results have been obtained for MMP-13 with compounds which have the following formula:

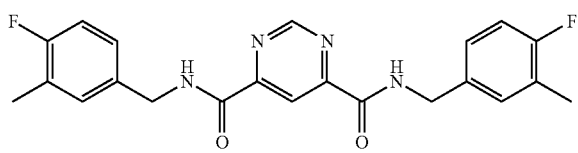 [SMILES: Cc1cc(CNC(=O)c2cc(C(=O)NCc3ccc(F)c(C)c3)ncn2)ccc1F]

This new family of inhibitors exploits the ability of these compounds to induce, when they bind to the active site of MMP-13, a conformational change in the deep cavity $S_{1'}$ located in the active site of MMP-13.

However, as discussed by the authors (Engel et al. 2005 Chem Biol (8)), only the $S_{1'}$ cavity of MMP-13 has this ability to change conformation following the binding of certain inhibitors, a property which explains the very high selectivity of these inhibitors for MMP-13, said inhibitors interacting only weakly with MMP-12.

Thus, there is in the prior art a need for MMP inhibitors, and in particular MMP-12 inhibitors, which do not comprise a zinc-binding group.

As it happens, it has been discovered that, surprisingly, compounds derived from RXP470, but not incorporating a substituted phosphoryl group, have an inhibitory activity with respect to MMPs, and in particular with respect to MMP-12.

Furthermore, after modification and optimization of their chemical structures, some of these compounds are powerful and selective inhibitors of MMP-12.

Thus, the invention proposes compounds of formula (1) below:

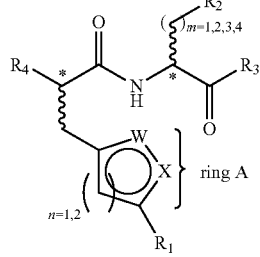

Formula (1)

in which:

n is 1 or 2, when n=1, W and X, independently of one another, are O, N or C, when n=2, W and X are C, $R_1$ is chosen from an iodine atom or a phenyl, biphenyl, 3'-chlorobiphenyl, phenoxy, phenoxymethyl, phenylethynyl, pyrimidine, 1-methyl-1H-pyrazole, 5-methyl-1,2,4-oxadiazole, 1,2,3-thiadiazole, 1H-pyrrole, thiazole, thiophene, 3a,7a-dihydrobenzo[d]thiazole, 3-aminophenyl, 3-hydroxyphenyl, 3-nitrophenyl, 3-carboxyphenyl, 3-chlorophenyl, 3,5-dichlorophenyl, 3-methoxyphenyl or 3-hydroxymethylphenyl group, or a thiophene ring substituted in positions, independently of one another, 2 and/or 3 and/or 4, with a group chosen from a methyl, phenyl or 3a,7a-dihydrobenzo[d]thiazole group or a hydrogen atom, m is an integer between 1 and 4 inclusive, and when m=1, $R_2$ is a carboxylic acid group or a 4-hydroxyphenyl group or a 1H-imidazole group or a hydroxyl group or an isopropyl group or a methyl group, when m=2, $R_2$ is a carboxylic acid or carboxamide group, when m=3, $R_2$ is a carboxylic acid group, when m=4, $R_2$ is an amino group, $R_3$ is chosen from an amino group; a carboxymethylpiperidine group, a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said $R_3$ group being bonded to the carbonyl group of formula (1) via an amino function, and $R_4$ is H or a carboxymethyl group —CH$_2$COOH, and preferably $R_4$ is H, and the diastereoisomers and enantiomers thereof.

In a first embodiment, the compounds of the invention are characterized in that, in formula (1), W is O, X is N, and n=1, forming a ring A which is an isoxazole ring, and in that they have the following formula (1-A):

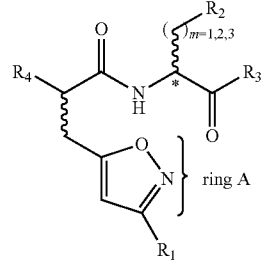

Formula (1-A)

in which:

$R_1$ is a phenyl, biphenyl or 3'-chlorobiphenyl group, m is an integer between 1 and 3 inclusive, $R_2$ is a carboxylic acid group when m is 1 or 3, or when m is 2, a carboxylic acid group or a carboxamide group, $R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said $R_3$ group being bonded to the carbonyl group of formula (1-A) via an amino function, and $R_4$ is H or a carboxymethyl group —CH$_2$COOH, and the diastereoisomers and enantiomers thereof.

In this first embodiment, the compounds of the invention are preferably chosen from the compounds having the following formulae (3) to (23):

Formula (3)
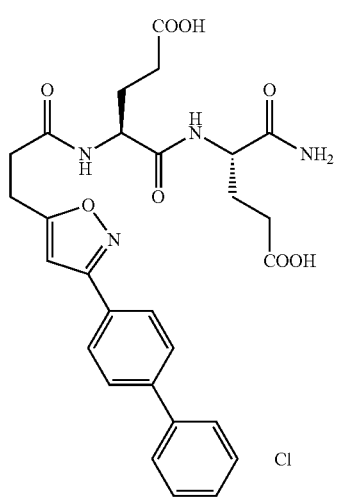
Formula (6)
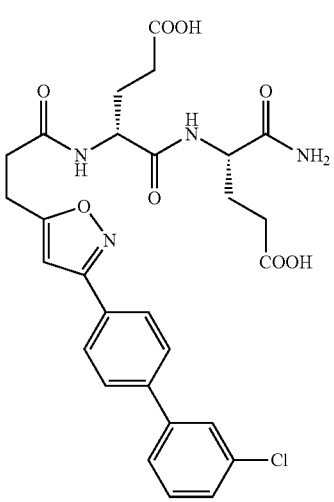
Formula (4)
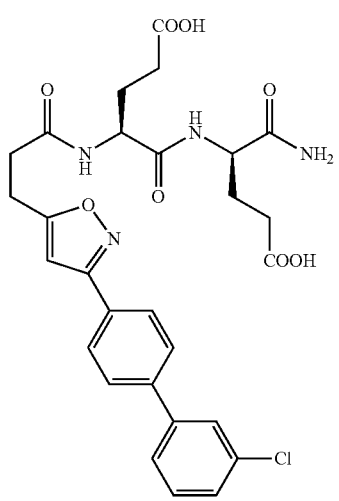
Formula (7)
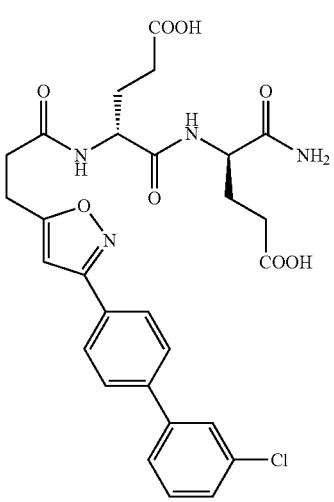
Formula (5)
Formula (8)

Formula (9)
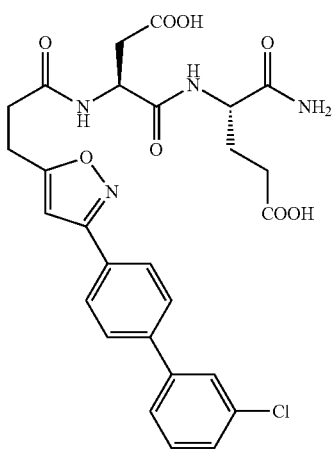
Formula (10)
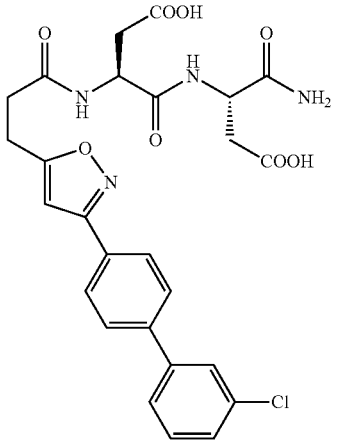
Formula (11)
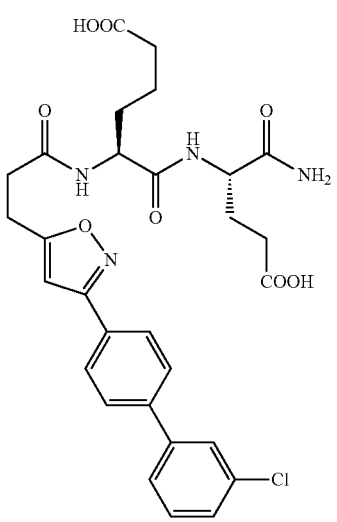
Formula (12)
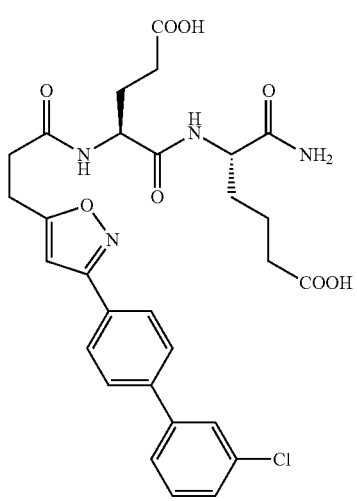
Formula (13)
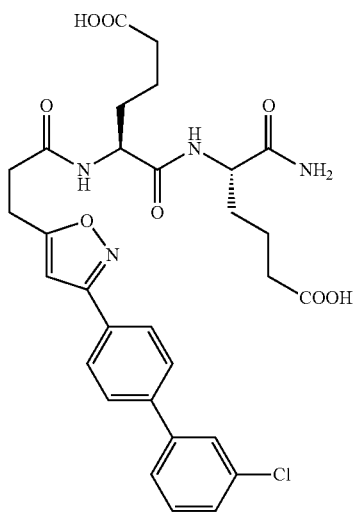
Formula (14)
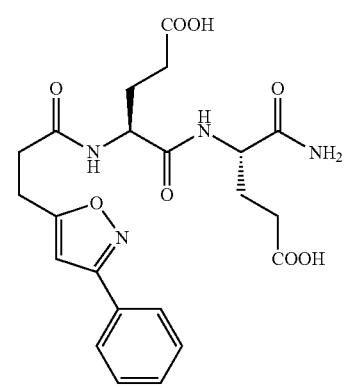

Formula (15)
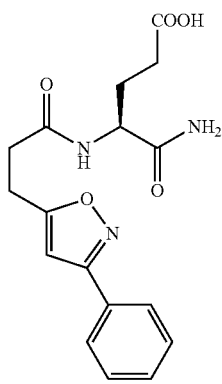
Formula (16)
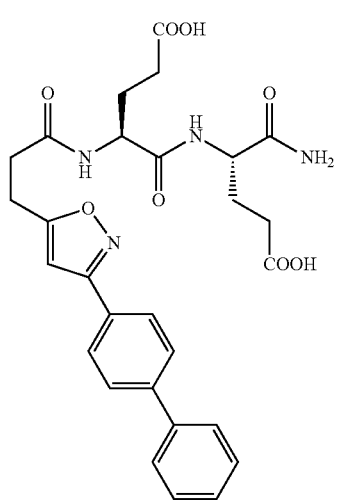
Formula (17)
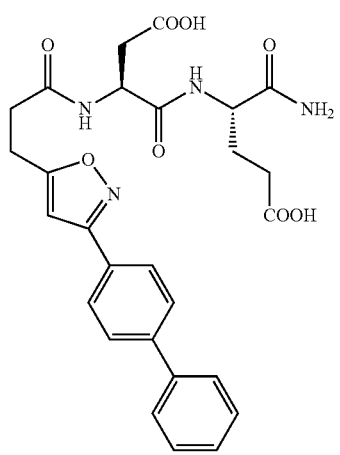
Formula (18)
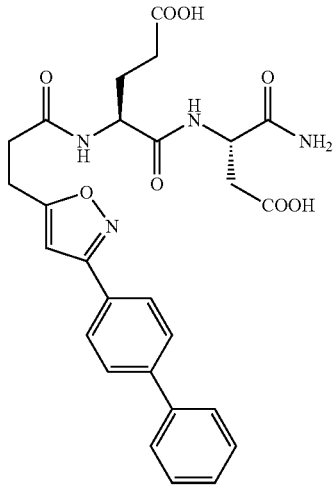
Formula (19)
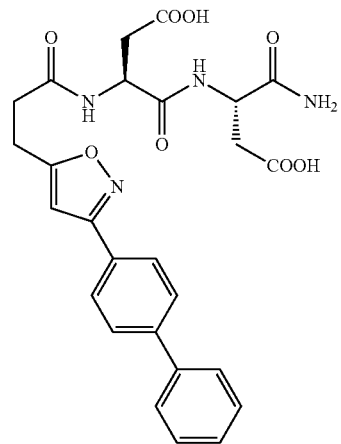
Formula (20)
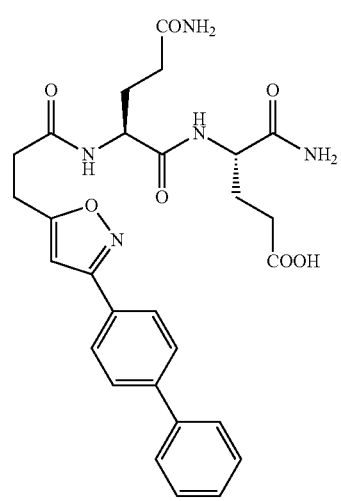

Formula (21)

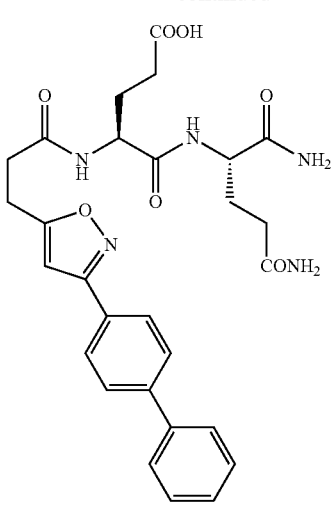

Formula (22)

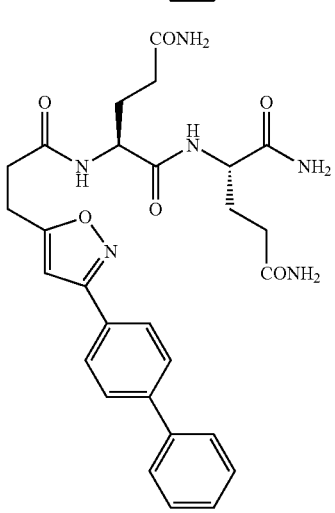

Formula (23)

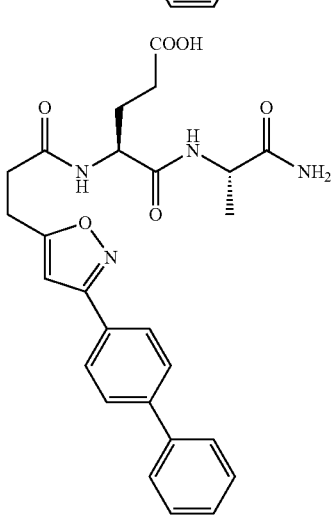

In a second embodiment, the compounds of the invention are characterized in that, in formula (1):
n=1,
W is N,
X is O,
$R_1$ is a phenyl, biphenyl or 3'-chlorobiphenyl group,
m=1, 2 or 3 when m=1 or 3, $R_2$ is a carboxylic acid group, and when m is 2, $R_2$ is a carboxylic acid or carboxamide group, $R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said $R_3$ group being bonded to the carbonyl group of formula (1) via an amino function, and $R_4$ is H or a carboxymethyl group —CH$_2$COOH, and in that they have the following formula (1-B):

Formula (1-B)

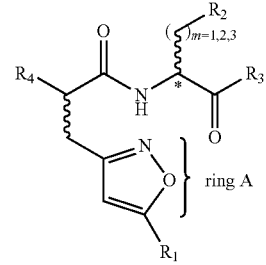

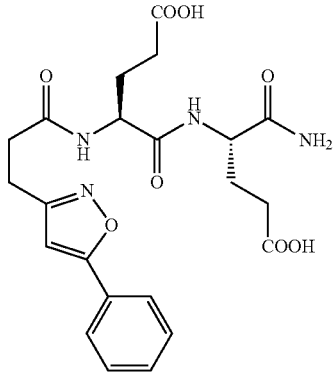

and the diastereoisomers and enantiomers thereof.

In this second embodiment, the preferred compound of the invention has the following formula (25):

Formula (25)

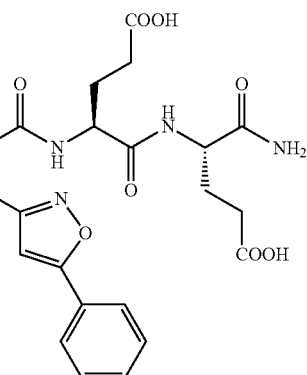

In a third embodiment, the compounds of the invention are characterized in that, in formula (1), W and X are C and n=2, thus forming a ring A which is a benzene ring, and in that they have the following formula (1-C):

Formula (1-C)

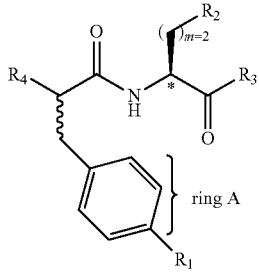

in which:
$R_1$ is chosen from an iodine atom or a phenyl, biphenyl, 3'-chlorobiphenyl, phenoxy, phenoxymethyl, phenylethynyl, pyrimidine, 1-methyl-1H-pyrazole, 5-methyl-1,2,4-oxadiazole, 1,2,3-thiadiazole, 1H-pyrrole, thiazole, thiophene and 3a,7a-dihydrobenzo[d]thiazole group, m=2, and $R_2$ is a carboxylic acid group, and $R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said $R_3$ group being bonded to the carbonyl group of formula (1-C) via an amino function, and $R_4$ is H or a carboxymethyl group —CH$_2$COOH, and the diastereoisomers thereof.

In these compounds, the asymmetric carbon is of (S) configuration.

In this third embodiment, the compounds of the invention are preferably chosen from the compounds having the following formulae (28) to (39):

Formula (28)
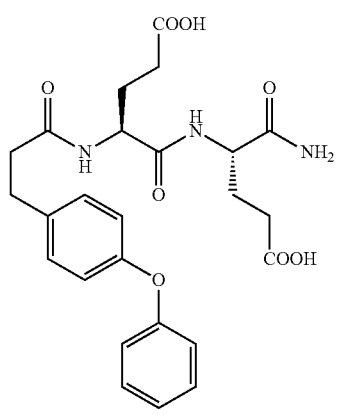

Formula (29)
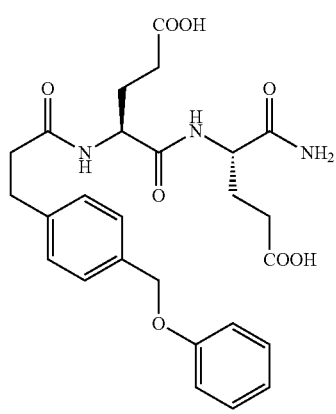

Formula (30)
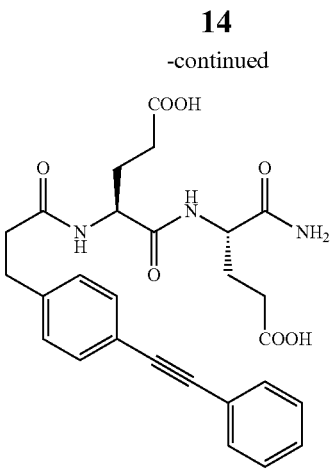

Formula (31)
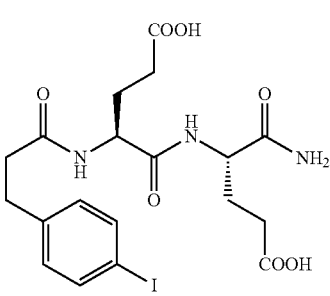

Formula (32)
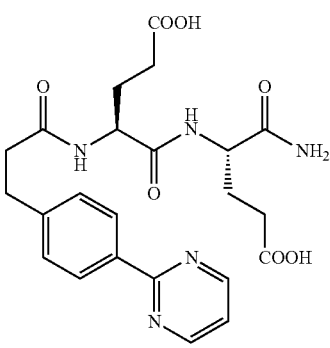

(Formula 33)
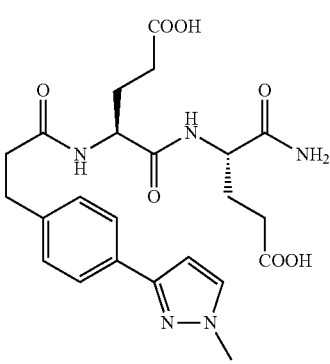

-continued

Formula (34)
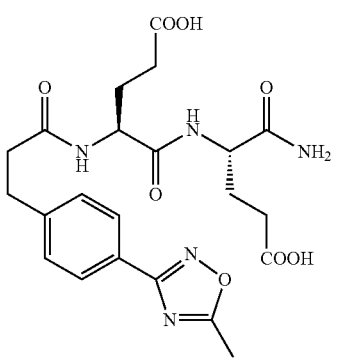

Formula (35)
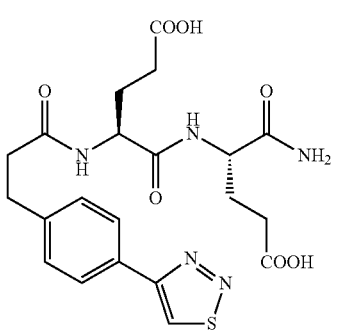

Formula (36)
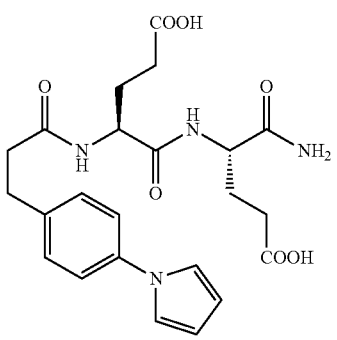

Formula (37)
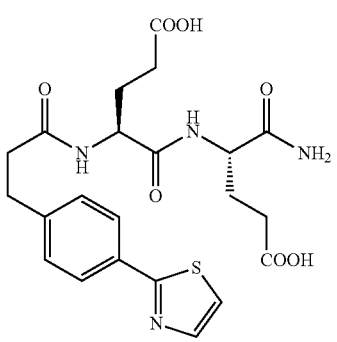

Formula (38)
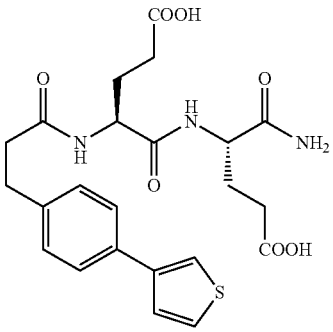

Formula (39)
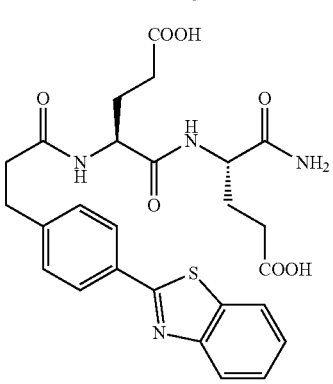

In a fourth embodiment, the compounds of the invention are characterized in that, in formula (1), W and X are C and n=2, thus forming a ring A which is a benzene ring, and in that they have the following formula (1-D):

Formula (1-D)
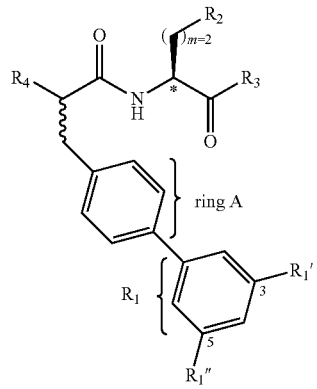

in which:
$R_1$ is:
either an unsubstituted phenyl group ($R_1$=H and $R_1''$=H),
or a phenyl group monosubstituted in position 3 with an amino group ($R_1$=NH$_2$, $R_1''$=H) or with a hydroxyl group ($R_1$=OH, $R_1''$=H) or with a nitro group ($R_1$=NO$_2$, $R_1''$=H) or with a carboxyl group ($R_1$=COOH, $R_1''$=H) or with a chlorine atom ($R_1$=Cl, $R_1''$=H) or with a methoxy group ($R_1$=OMe, $R_1''$=H) or with a hydroxymethyl group ($R_1$=CH$_2$OH, $R_1''$=H),
or a phenyl group disubstituted in positions 3 and 5 with a chlorine atom ($R_1$=Cl and $R_1''$=Cl), m=2, R$_2$ is a carboxylic acid group, and R$_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said R$_3$ group being bonded to the carbonyl group of formula (1-D) via an amino function, and R$_4$ is H or a carboxymethyl group —CH$_2$COOH, and the diastereoisomers thereof.

In this fourth embodiment, the compounds of the invention are preferably chosen from the compounds having the following formulae (40) and (42) to (60):

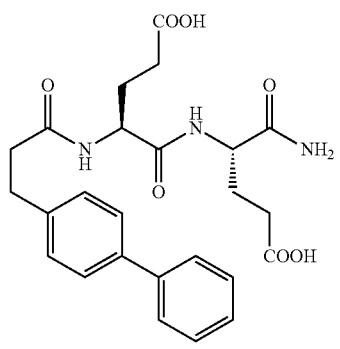

Formula (40)


Formula (42)

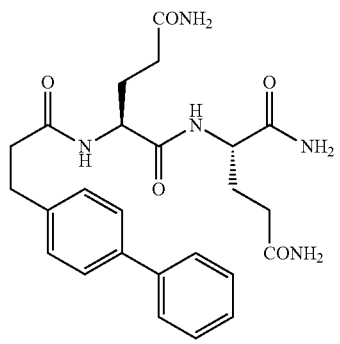

Formula (43)

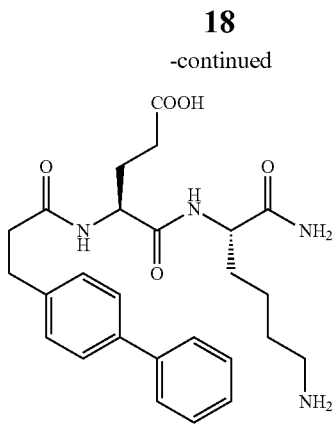

Formula (44)

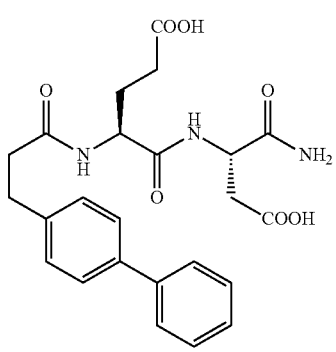

Formula (45)

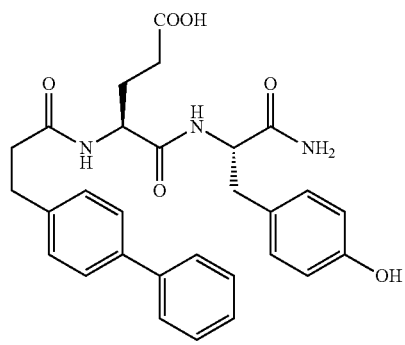

Formula (46)

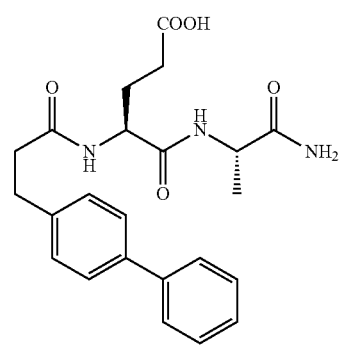

Formula (47)

Formula (48)
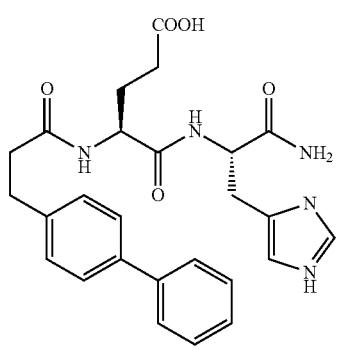
Formula (49)
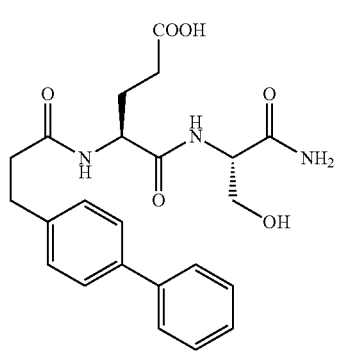
Formula (50)
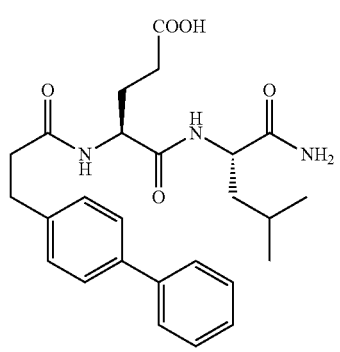
Formula (51)
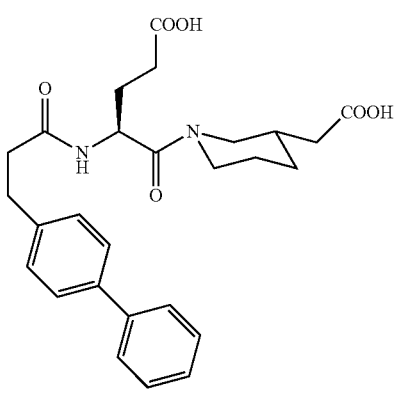
Formula (52)
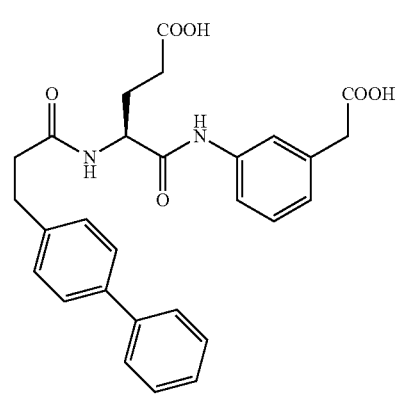
Formula (53)
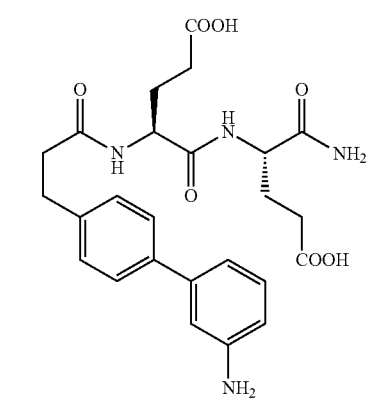
Formula (54)
Formula (55)

Formula (56)
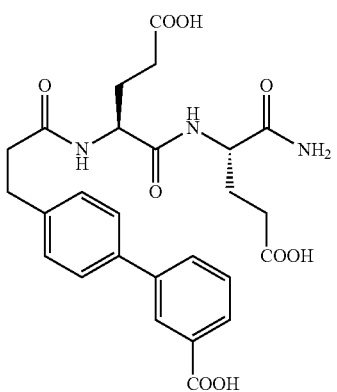

Formula (57)
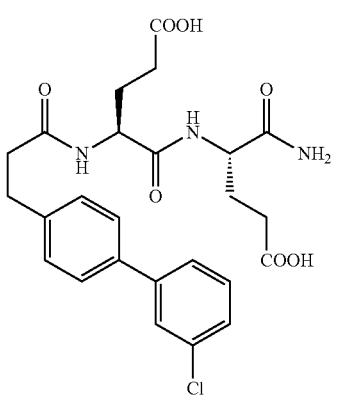

Formula (58)
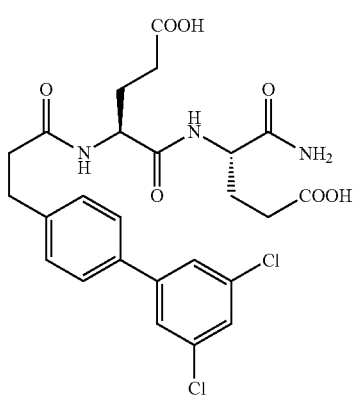

Formula (59)
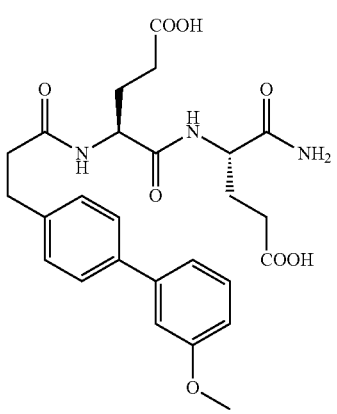

Formula (60)
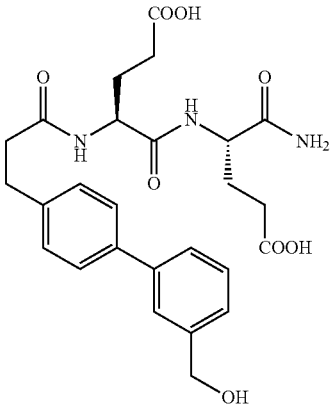

In a fifth embodiment, the compounds of the invention are characterized in that, in formula (1), W and X are C, n=2 and $R_1$ is a biphenyl group, and in that they correspond to the following formula (1-E):

Formula (1-E)
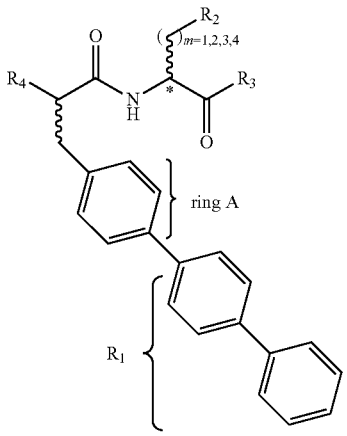

in which:
m=1, 2, 3 or 4,
when m=1, $R_2$ is a carboxylic acid, 4-hydroxyphenyl or 1H-imidazole or hydroxyl group or an isopropyl or methyl,
when m=2, $R_2$ is a carboxylic acid or carboxamide group,
when m=3, $R_2$ is a carboxlylic acid group,
when m=4, $R_2$ is an amino group,
$R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said $R_3$ group being bonded to the carbonyl group of formula (1-E) via an amino function, and
$R_4$ is H or a carboxymethyl group —CH$_2$COOH, and the diastereoisomers and enantiomers thereof.
In this fifth embodiment, the preferred compounds of the invention are chosen from the compounds having the following formulae (61) to (79):

Formula (61)
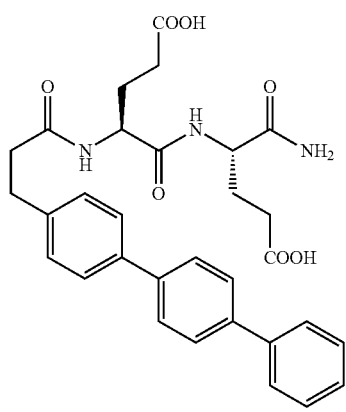
Formula (62)
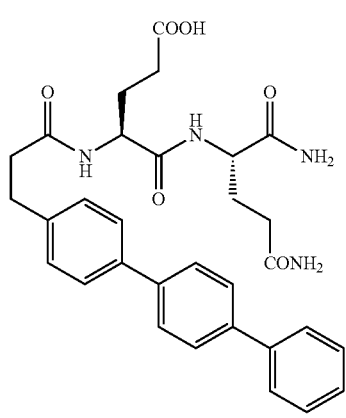
Formula (63)
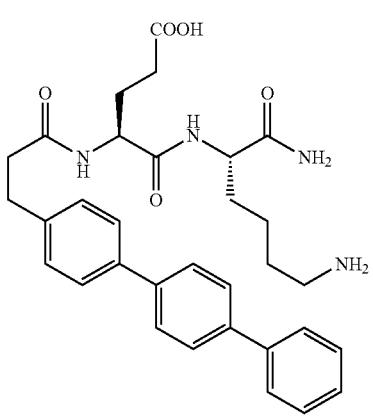
Formula (64)
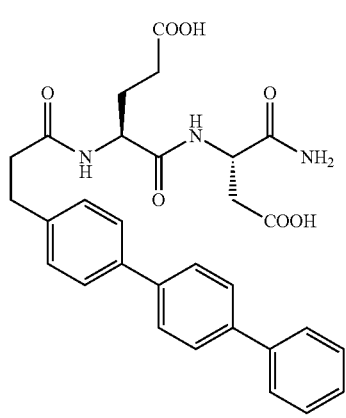
-continued
Formula (65)
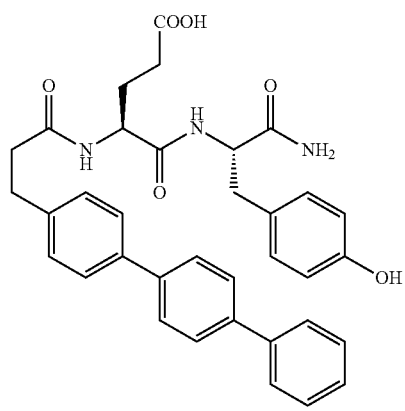
Formula (66)
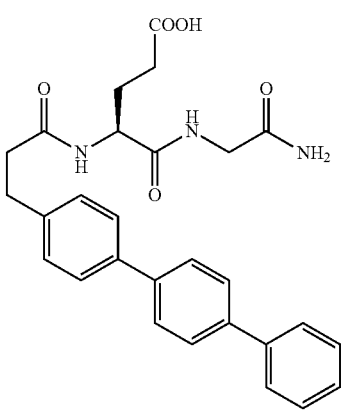
Formula (67)
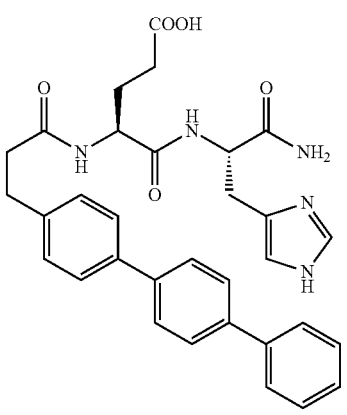
Formula (68)
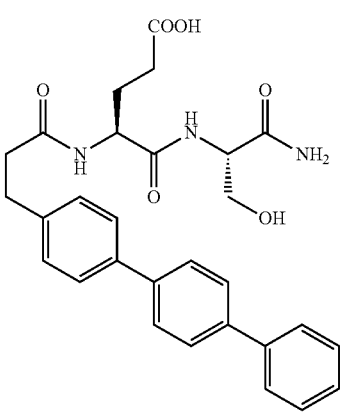

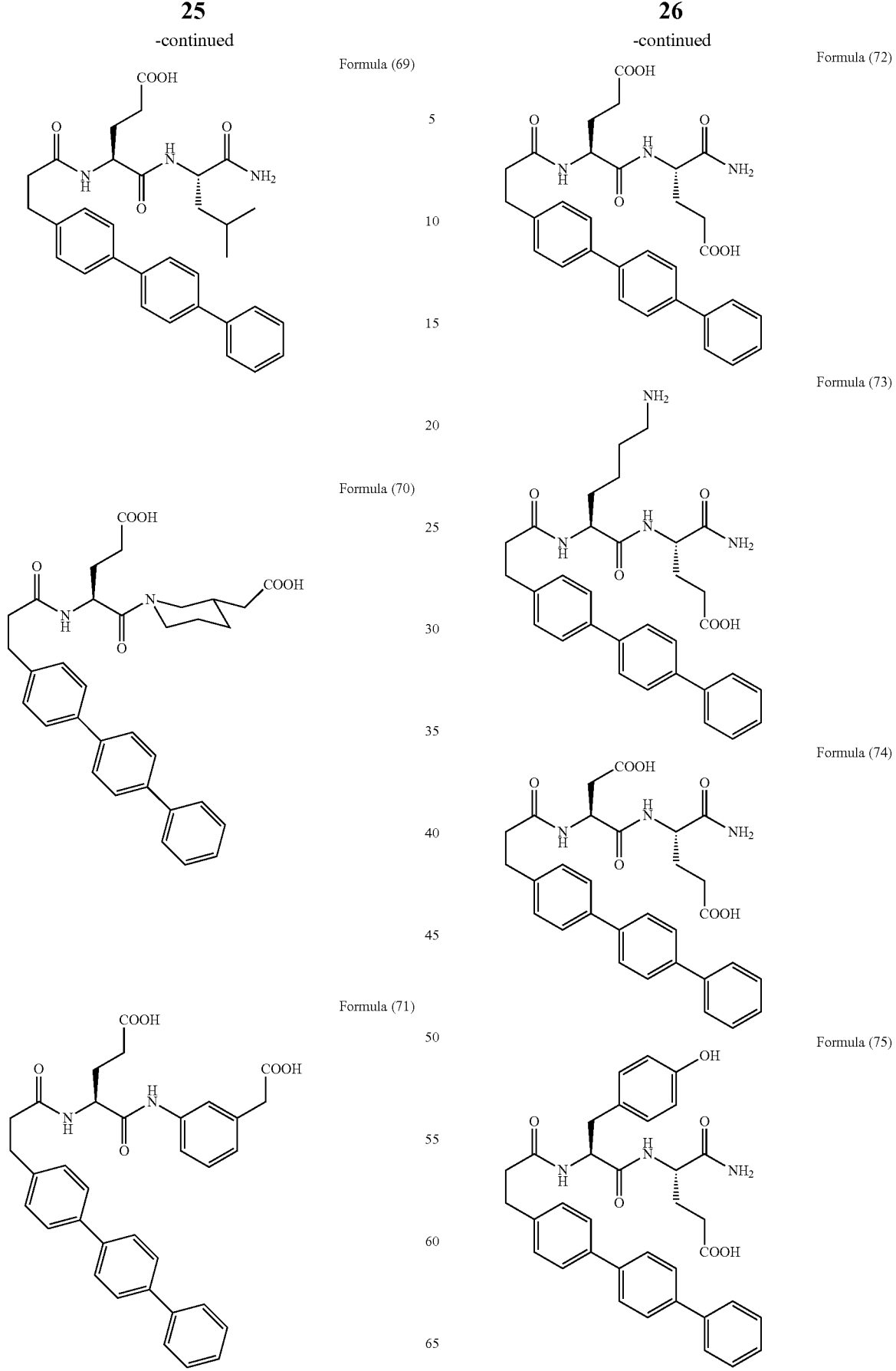

-continued

Formula (76)
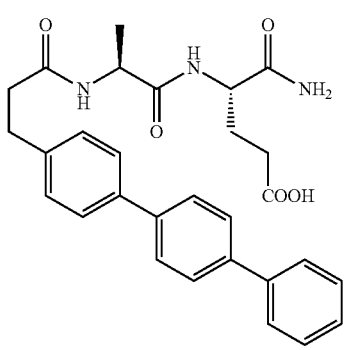

Formula (77)
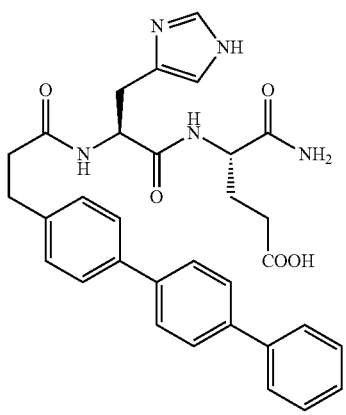

Formula (78)
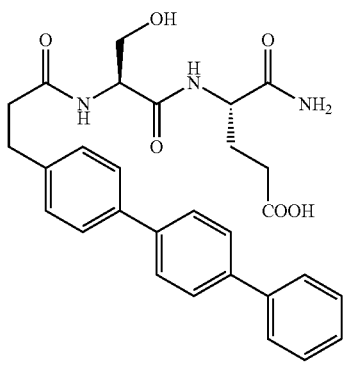

Formula (79)
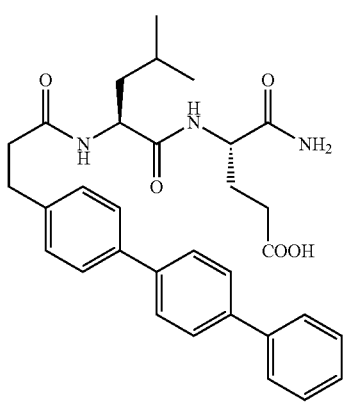

In a sixth embodiment, the compounds of the invention are characterized in that, in formula (1), W and X are C and n=2, forming a ring A which is a benzene ring, and $R_1$ is a thiophene ring substituted with an $R_1'''$ group, and in that they have the following formula (1-F):

Formula (1-F)
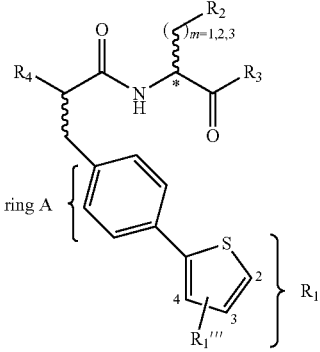

$R_1$ is:
either an unsubstituted thiophene ring ($R_1'''$=H),
or a thiophene ring monosubstituted in position 2 with a group chosen from a methyl ($R_1'''$=CH$_3$), phenyl ($R_1'''$=Ph) or 3a,7a-dihydrobenzo[d]thiazole group,
or a thiophene ring monosubstituted in position 3 with a group chosen from a methyl ($R_1'''$ . . . =CH$_3$) or phenyl ($R_1'''$=Ph) group,
or a thiophene ring monosubstituted in position 4 with a methyl group ($R_1'''$ . . . =CH$_3$), m=1, 2 or 3, and $R_2$ is a carboxylic acid or imidazole group when m=1, or a carboxylic acid or carboxamide group when m=2, or a carboxylic acid group when m=3, $R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said $R_3$ group being bonded to the carbonyl group of formula (1-F) via an amino function, and $R_4$ is H or a carboxymethyl group —CH$_2$COOH, and the diastereoisomers and enantiomers thereof.

In this sixth embodiment, the compounds of the invention are preferably chosen from the compounds having the following formulae (80) to (107):

Formula (80)
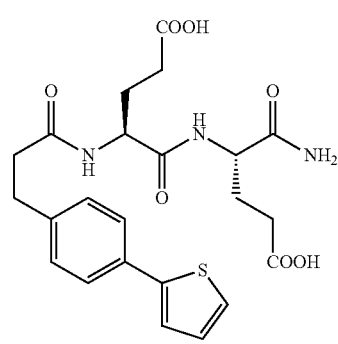

Formula (81)
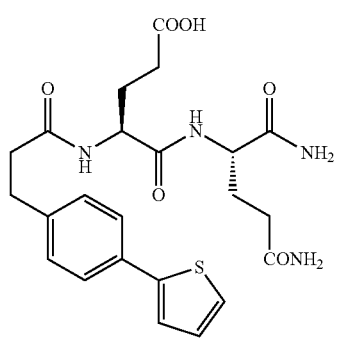
Formula (82)
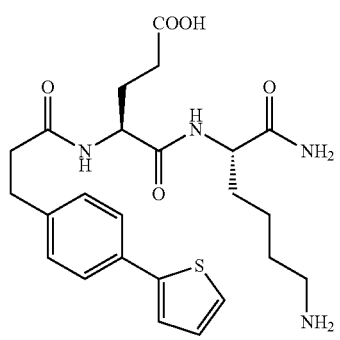
Formula (83)
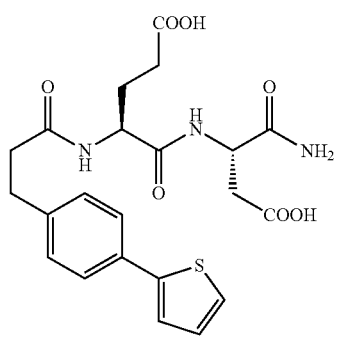
Formula (84)
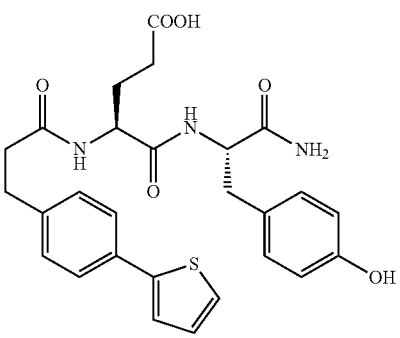
Formula (85)
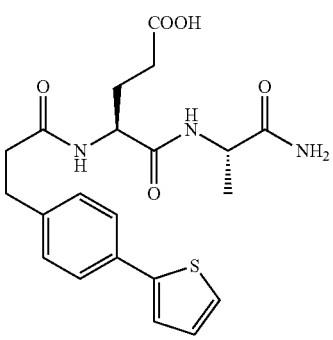
Formula (86)
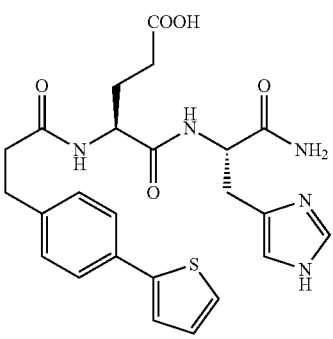
Formula (87)
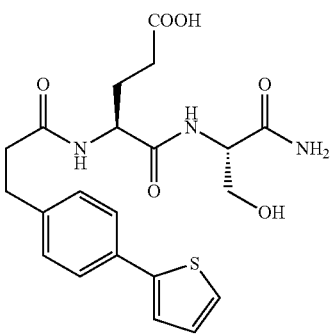
Formula (88)
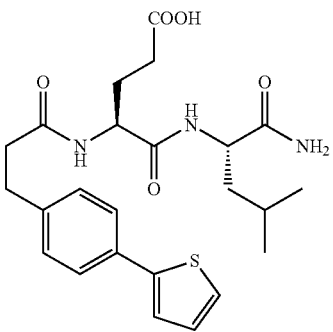

Formula (89)
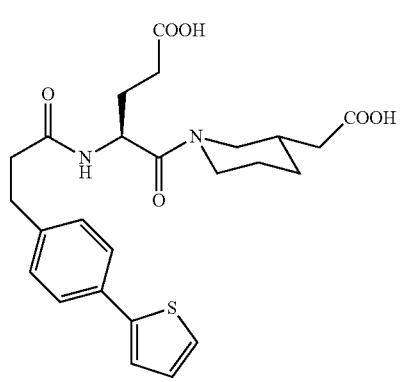
Formula (90)
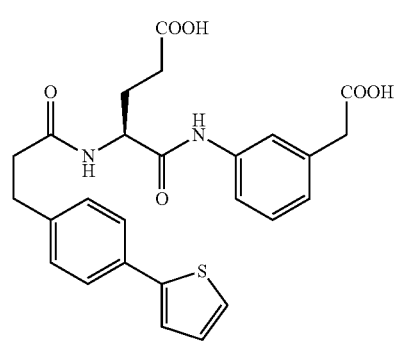
Formula (91)
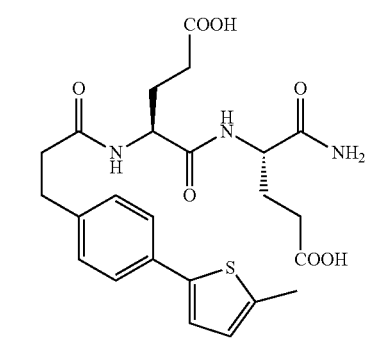
Formula (92)
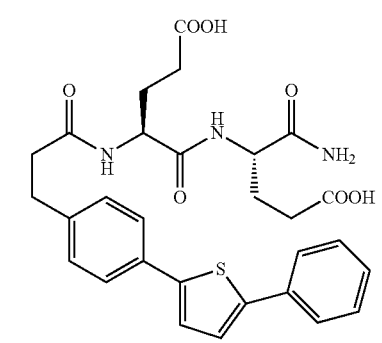
Formula (93)
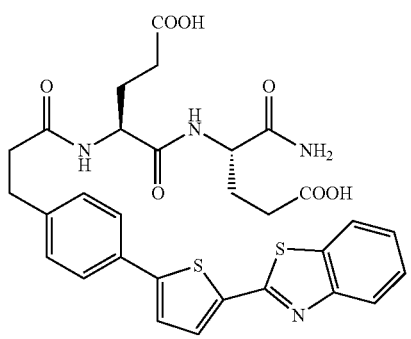
Formula (94)
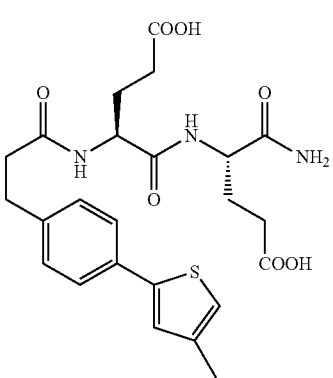
Formula (95)
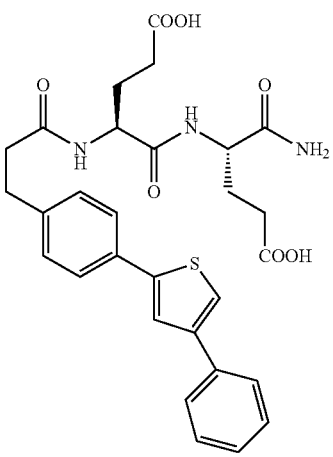
Formula (96)
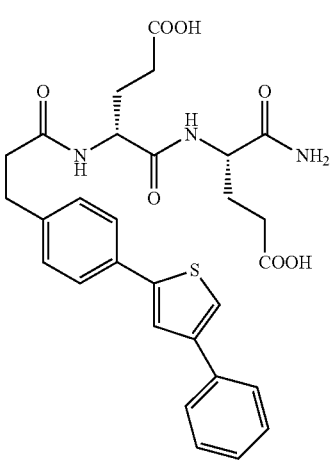

33
-continued
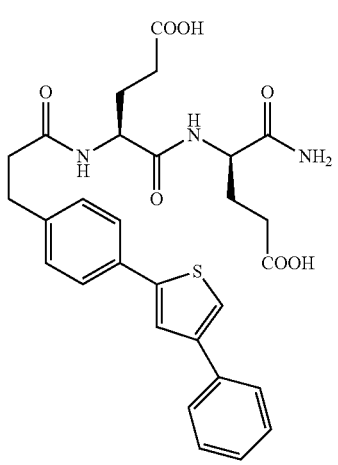
Formula (97)
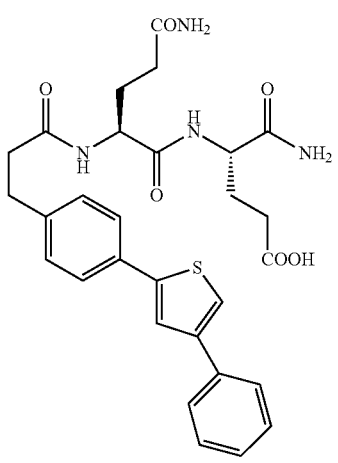
Formula (98)
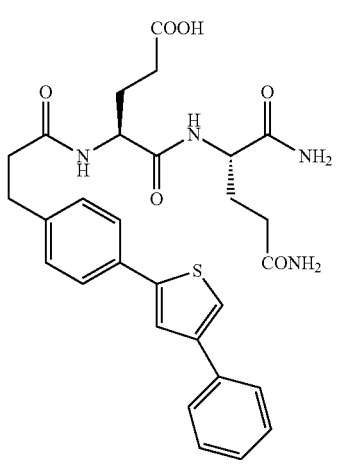
Formula (99)
34
-continued
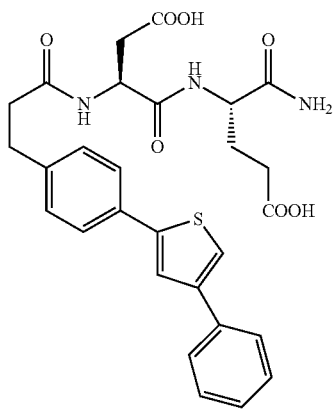
Formula (100)
Formula (101)
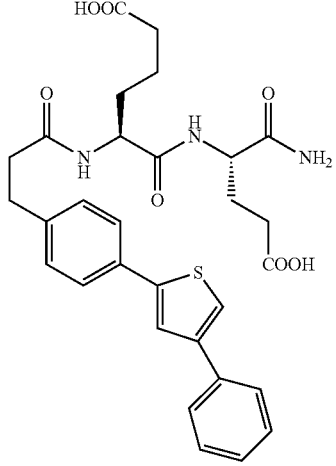
Formula (102)

Formula (103)
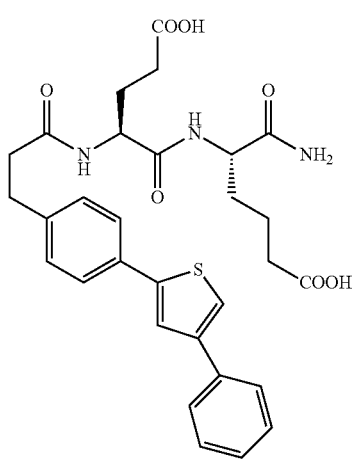
Formula (104)
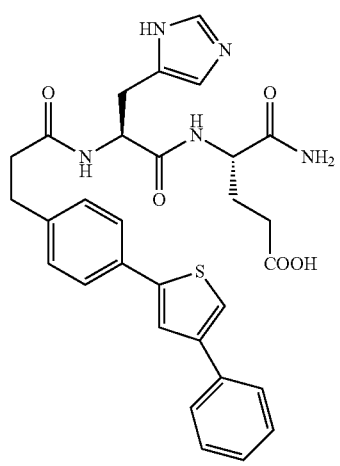
Formula (105)
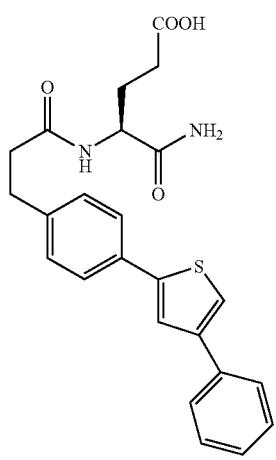
Formula (106)
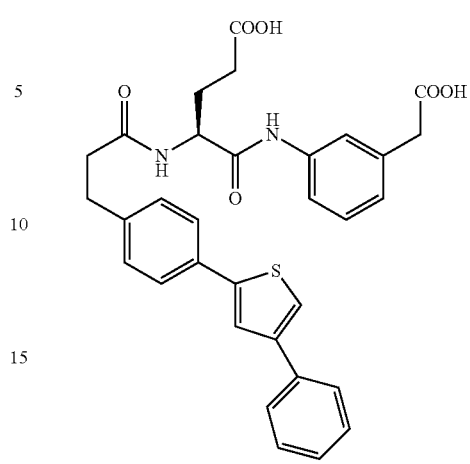
Formula (107)
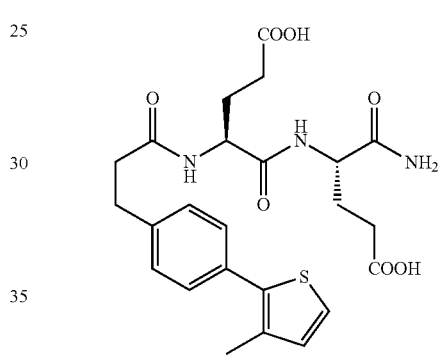
Formula (95bis)
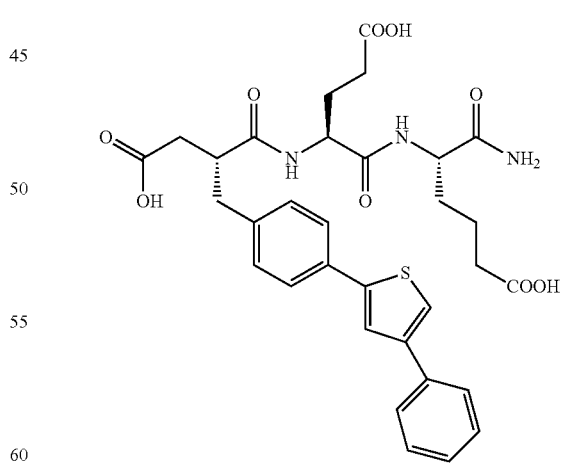
In this sixth embodiment, the most preferred compounds of the invention are chosen from the compounds of formula (1-F) in which the ring $R_1$ is a thiophene ring monosubstituted either in position 2 with a methyl or phenyl group, or in position 3 with a phenyl group.

These compounds have the following formula (1-F1):

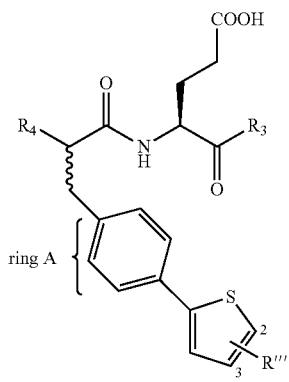

Formula (1-F1)

in which:

R$_1'''$ is either in position 2 or in position 3 of the thiophene ring and is chosen from a methyl (R$_1'''$=CH$_3$) or phenyl (R$_1'''$...=Ph) group, and R$_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said R$_3$ group being bonded to the carbonyl group of formula (1-F1) via an amino function, and R$_4$ is H or a carboxymethyl group —CH$_2$COOH, and the diastereoisomers thereof.

The preferred compounds of formula (1-F1) are the compounds having the following formulae (91), (92), (95), (97), (99), (101), (103), (105), (106) and (95 bis):

Formula (91)

Formula (92)

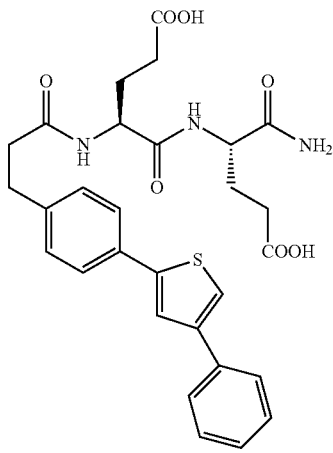

Formula (95)

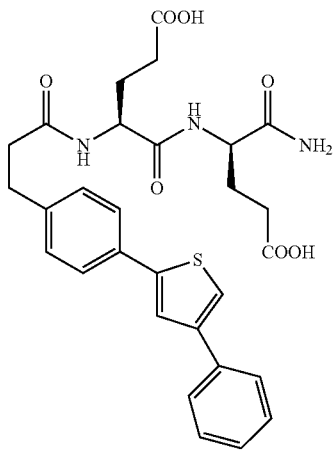

Formula (97)

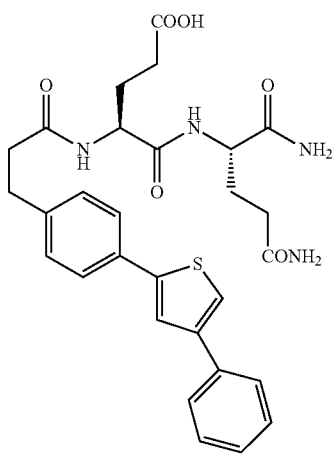

Formula (99)

Formula (101)
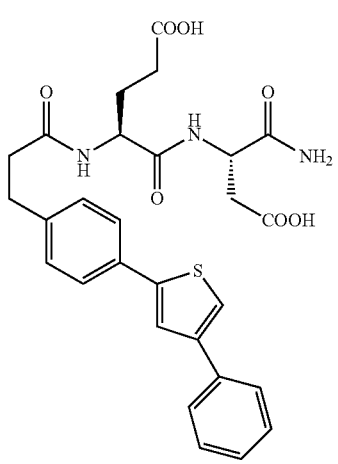
Formula (103)
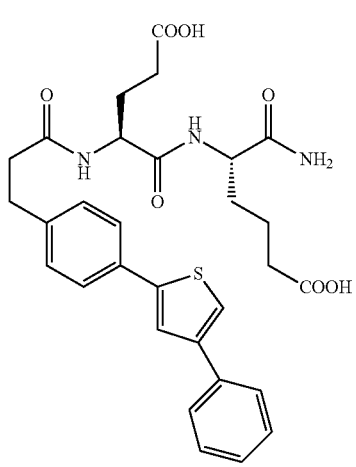
Formula (105)
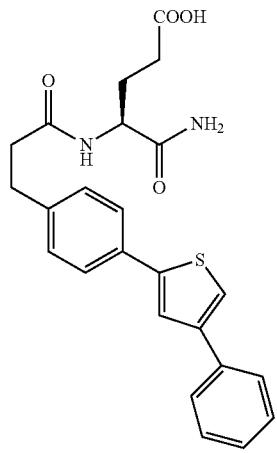
Formula (106)
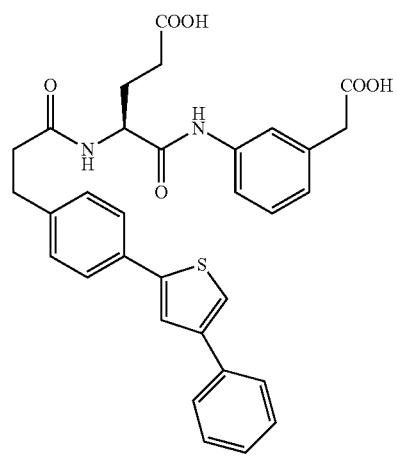
Formula (95bis)
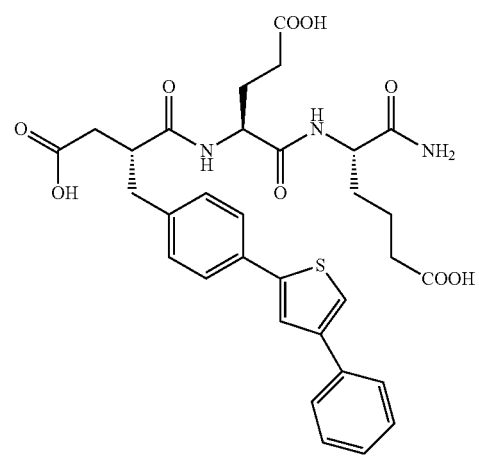
However, the most preferred compounds of the invention are the compounds of formula (1-F2) in which $R_1$ is a thiophene ring monosubstituted in position 3 with a phenyl ring, and which correspond to the following formula (1-F2):
Formula (1-F2)
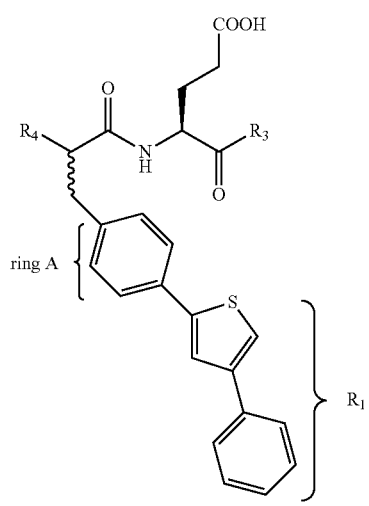

in which:

R₃ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH₂, and said R₃ group being bonded to the carbonyl group of formula (1-F2) via an amino function, and R₄ is H or a carboxymethyl group —CH₂COOH, and in particular the compounds having the following formulae (95), (97), (99), (101), (103), (105), (106) and (95 bis):

Formula (95)

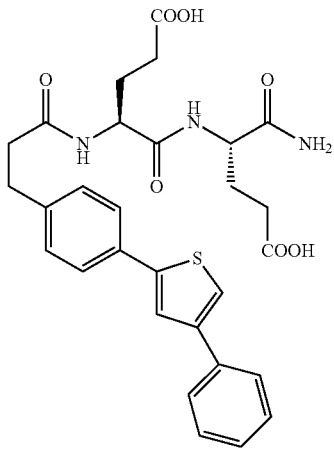

Formula (97)

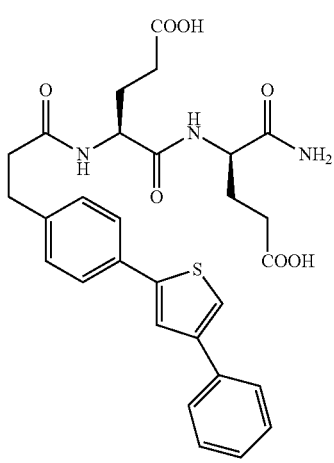

Formula (99)

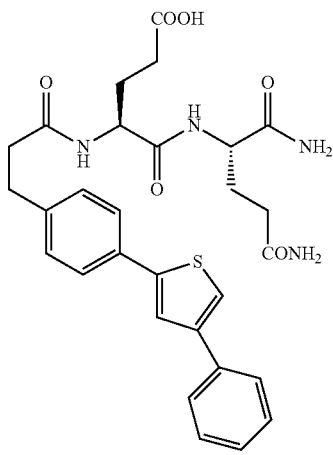

Formula (101)

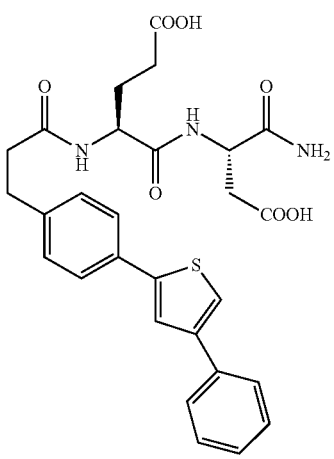

Formula (103)

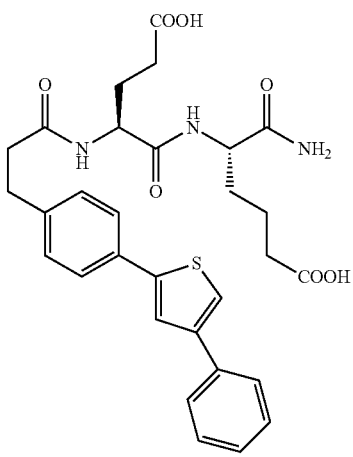

-continued

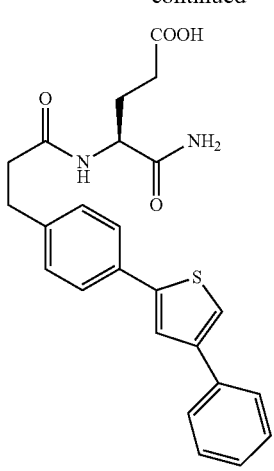

Formula (105)

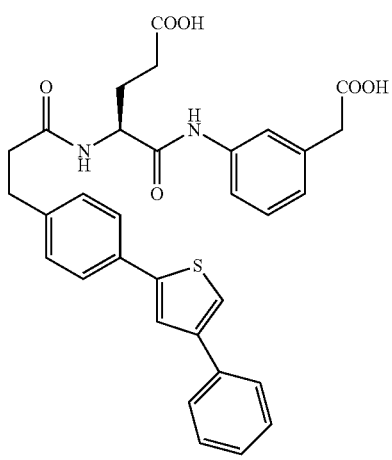

Formula (106)

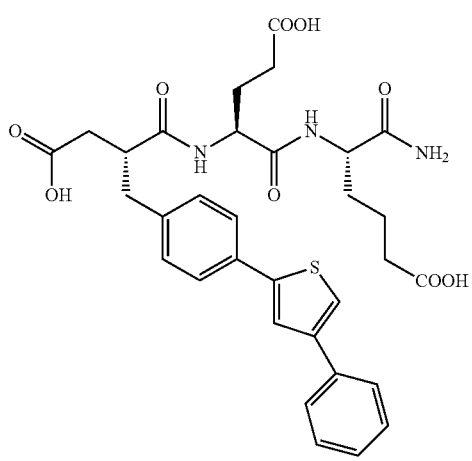

Formula (95bis)

and the diastereosimers thereof.

The invention also proposes the compounds of the invention and the enantiomers and diastereoisomers thereof, for use as a medicament.

The invention further proposes the compounds of the invention and the enantiomers and diastereoisomers thereof, for use as extracellular matrix metalloproteinase inhibitors.

More particularly, the invention proposes the compounds of formulae (91), (92), (95), (97), (99), (101), (103), (105), (106) and (95 bis), for use as extracellular matrix metalloproteinase 12 (MMP-12) inhibitors, and more particularly the compounds (95), (97), (99), (101), (103), (105), (106) and (95 bis).

The invention additionally proposes a pharmaceutical composition comprising at least one of the compounds of the invention or an enantiomer or diastereoisomer thereof, and a pharmaceutically acceptable excipient.

Finally, the invention proposes the compounds of the invention and the enantiomers and diastereoisomers thereof, for use as a medicament for treating cancer, inflammatory diseases, chronic obstructive pulmonary disease (COPD), arthritis, rhumatoid arthritis, atherosclerosis and a ruptured aneurysm.

The invention will be understood more clearly, and other characteristics and advantages thereof will emerge more clearly, on reading the description which follows.

The compounds of the invention have the following general formula (1):

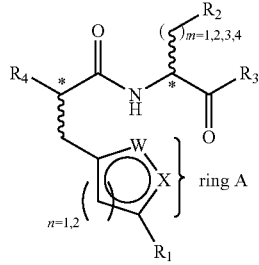

Formula (1)

in which:

n is 1 or 2, when n=1, W and X, independently of one another, are O, N or C, when n=2, W and X are C, $R_1$ is chosen from an iodine atom or a phenyl, biphenyl, 3'-chlorobiphenyl, phenoxy, phenoxymethyl, phenylethynyl, pyrimidine, 1-methyl-1H-pyrazole, 5-methyl-1,2,4-oxadiazole, 1,2,3-thiadiazole, 1H-pyrrole, thiazole, thiophene, 3a,7a-dihydrobenzo[d]thiazole, 3-aminophenyl, 3-hydroxyphenyl, 3-nitrophenyl, 3-carboxyphenyl, 3-chlorophenyl, 3,5-dichlorophenyl, 3-methoxyphenyl or 3-hydroxymethylphenyl group, or a thiophene ring substituted in positions, independently of one another, 2 and/or 3 and/or 4, with a group chosen from a methyl, phenyl or 3a,7a-dihydrobenzo[d]thiazole group or a hydrogen atom, m is an integer between 1 and 4 inclusive, and when m=1, $R_2$ is a carboxylic acid group or a 4-hydroxyphenyl group, or a 1H-imidazole group or a hydroxyl group or an isopropyl group or a methyl group, when m=2, $R_2$ is a carboxylic acid or carboxamide group, when m=3, $R_2$ is a carboxylic acid group, when m=4, $R_2$ is an amino group, $R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said $R_3$ group being bonded to the carbonyl group of formula (1) via an amino function, and $R_4$ is 1-1 or a carboxymethyl group —CH$_2$COOH, and preferably $R_4$ is H.

More specifically, when $R_2$ is a carboxylic acid group, i.e. a —COOH group, which is possible when m=1, 2 or 3, the $R_2$ group may be in the (S) configuration or (R) configuration when m is 2.

Likewise, when $R_3$ is a glutamate residue, this residue may be in the L or D configuration.

When the $R_4$ group is a carboxymethyl group —CH$_2$COOH, the asymmetric carbon (C*) carrying the $R_4$ group may be in the (S) configuration or (R) configuration, and preferably in the (S) configuration.

Thus, the diastereoisomers and enantiomers of the compounds of formula (1) above are also a subject of the invention.

Depending on the nature of the ring A, in formula (1), various families are defined.

In the first family, the ring A is an isoxazole ring, i.e. W is O, X is N, and n=1 and m is 1, 2 or 3.

The compounds belonging to this first family are the compounds having the following formula (1-A):

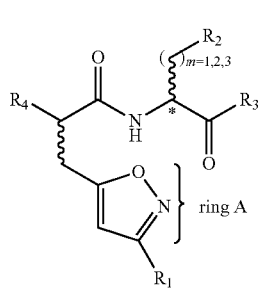

Formula (1-A)

in which:
$R_1$ is a phenyl, biphenyl or 3'-chlorobiphenyl group,
m is an integer between 1 and 3 inclusive,
$R_2$ is a carboxylic acid group when m is 1 or 3, or when m is 2, a carboxylic acid group or a carboxamide group,
$R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxyl functions of said amino acids to be carboxamide functions —C(=O)NH$_2$, and said $R_3$ group being bonded to the carbonyl group of formula (1-A) via an amino function, and
$R_4$ is H or a carboxymethyl group —CH$_2$COOH, and the diastereoisomers and enantiomers thereof.

It is noted that, in this first family:
when m=1, 2 or 3 and $R_2$ is a COOH group (carboxylic acid) group, $R_2$ forms, with the NH group and the C(=O)—$R_3$ group to which it is bonded, respectively an aspartate, glutamate and homoglutamate residue,
when m=2 and $R_2$ is a carboxamide group, $R_2$ forms, with the NH group and the C(=O)—$R_3$ group to which it is bonded, a glutamine residue,
when m=1 and $R_2$ is a 4-hydroxyphenyl or 1H-imidazole or hydroxyl or isopropyl or methyl group, $R_2$ forms, with the NH group and the C(=O)—$R_3$ group to which it is bonded, respectively a tyrosine, histidine, serine, leucine or alanine residue,
when m=4 and $R_2$ is an amino group, $R_2$ forms, with the NH group and the C(=O)—$R_3$ group to which it is bonded, a lysine residue.

The preferred compounds of this first family are the compounds having the following formulae (3) to (23):

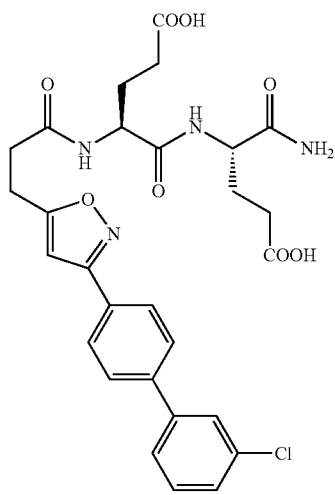 [SMILES: NC(=O)[C@H](CCC(=O)O)NC(=O)[C@H](CCC(=O)O)NC(=O)CCc1cc(-c2ccc(-c3cccc(Cl)c3)cc2)no1]

Formula (3)

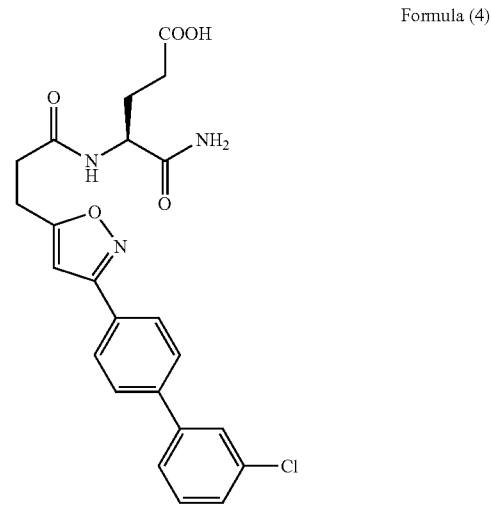

Formula (4)

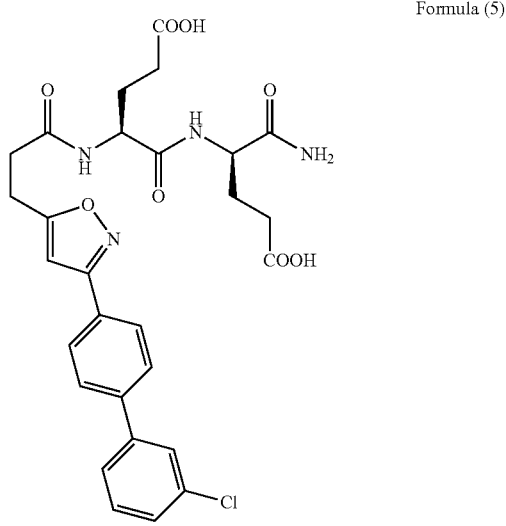

Formula (5)

Formula (6)
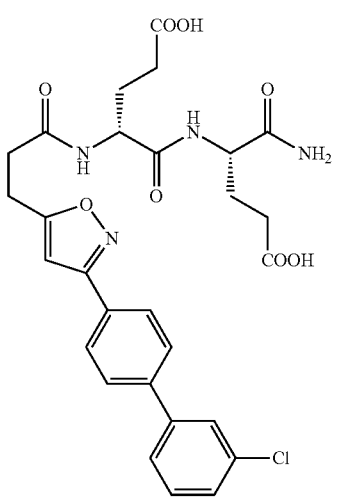 [SMILES: NC(=O)[C@H](CCC(=O)O)NC(=O)[C@@H](CCC(=O)O)NC(=O)CCc1cc(-c2ccc(-c3cccc(Cl)c3)cc2)no1]
Formula (7)
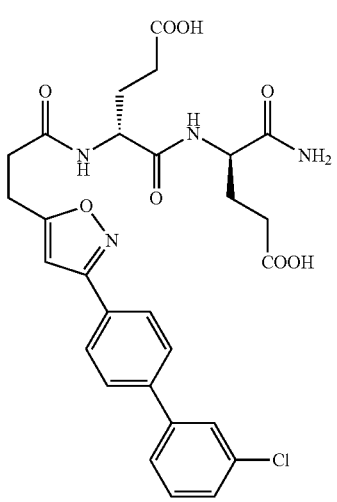 [SMILES: NC(=O)[C@@H](CCC(=O)O)NC(=O)[C@@H](CCC(=O)O)NC(=O)CCc1cc(-c2ccc(-c3cccc(Cl)c3)cc2)no1]
Formula (8)
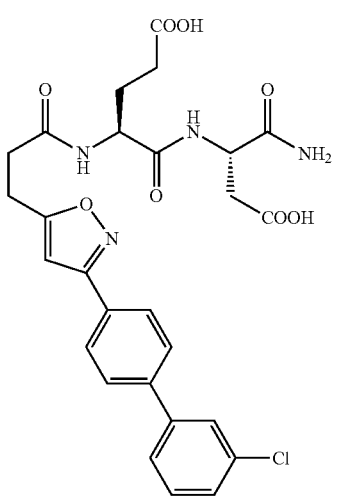 [SMILES: NC(=O)[C@H](CC(=O)O)NC(=O)[C@H](CCC(=O)O)NC(=O)CCc1cc(-c2ccc(-c3cccc(Cl)c3)cc2)no1]
Formula (9)
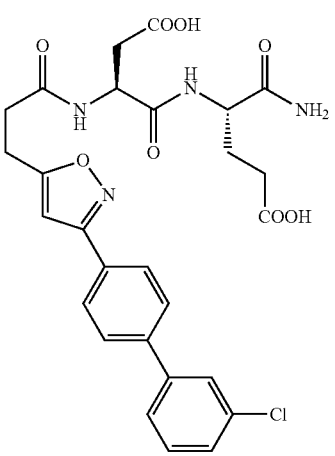 [SMILES: NC(=O)[C@H](CCC(=O)O)NC(=O)[C@H](CC(=O)O)NC(=O)CCc1cc(-c2ccc(-c3cccc(Cl)c3)cc2)no1]
Formula (10)
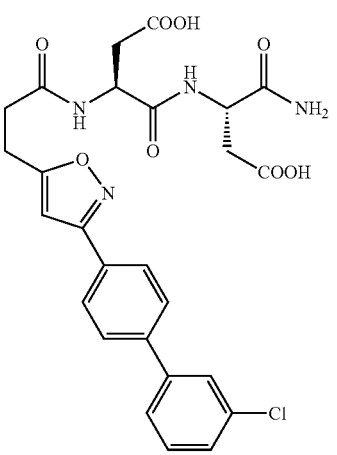 [SMILES: NC(=O)[C@H](CC(=O)O)NC(=O)[C@H](CC(=O)O)NC(=O)CCc1cc(-c2ccc(-c3cccc(Cl)c3)cc2)no1]
Formula (11)
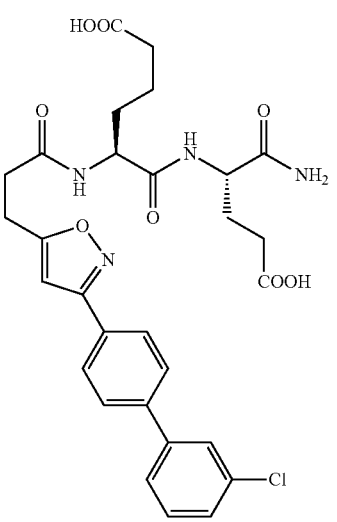

Formula (12)
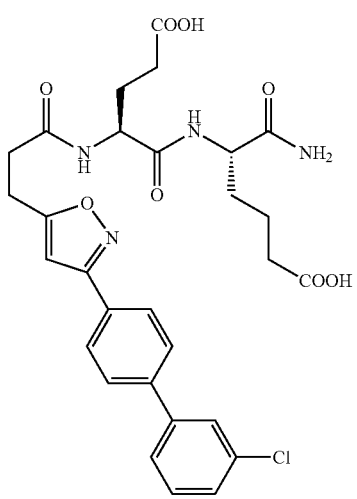 [SMILES: NC(=O)[C@H](CCCC(=O)O)NC(=O)[C@H](CCC(=O)O)NC(=O)CCc1cc(-c2ccc(-c3cccc(Cl)c3)cc2)no1]
Formula (13)
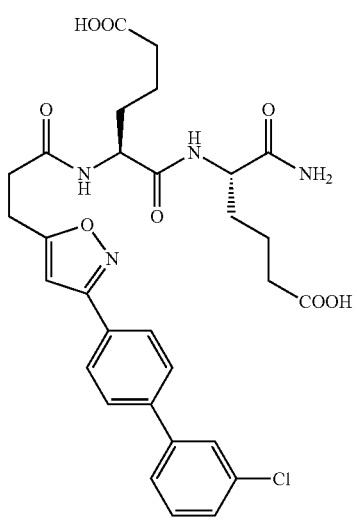 [SMILES: NC(=O)[C@H](CCCC(=O)O)NC(=O)[C@H](CCCC(=O)O)NC(=O)CCc1cc(-c2ccc(-c3cccc(Cl)c3)cc2)no1]
Formula (14)
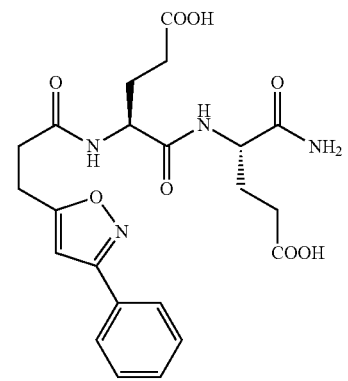 [SMILES: NC(=O)[C@H](CCC(=O)O)NC(=O)[C@H](CCC(=O)O)NC(=O)CCc1cc(-c2ccccc2)no1]
Formula (15)
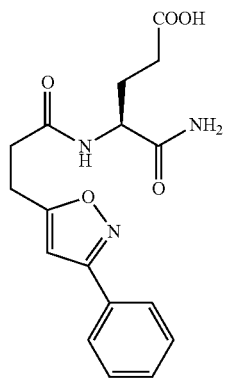 [SMILES: NC(=O)[C@H](CCC(=O)O)NC(=O)CCc1cc(-c2ccccc2)no1]
Formula (16)
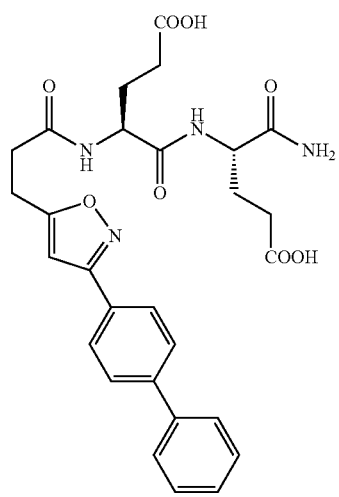 [SMILES: "COOH" ; CC[C@H](NC(=O)CCc1cc(-c2ccc(-c3ccccc3)cc2)no1)C(=O)N[C@@H](CCC(=O)O)C(N)=O]
Formula (17)
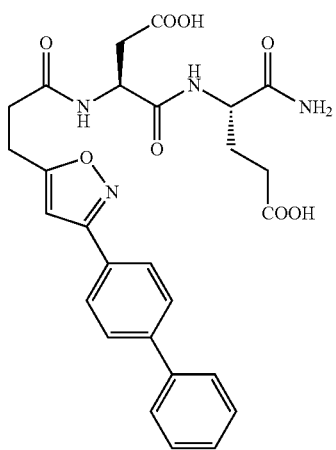 [SMILES: NC(=O)[C@H](CCC(=O)O)NC(=O)[C@H](CC(=O)O)NC(=O)CCc1cc(-c2ccc(-c3ccccc3)cc2)no1]

Formula (18)

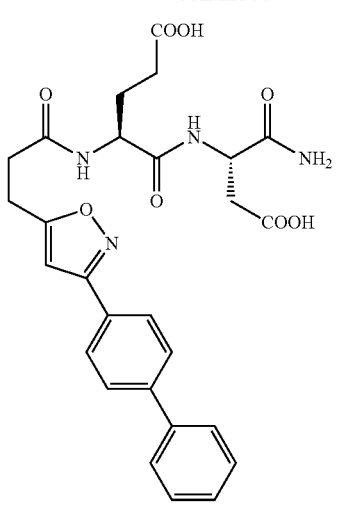 [SMILES: "COOH" ; CC[C@H](NC(=O)CCc1cc(-c2ccc(-c3ccccc3)cc2)no1)C(=O)N[C@@H](CC(=O)O)C(N)=O]

Formula (19)

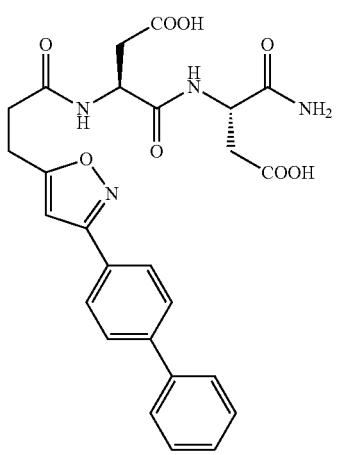 [SMILES: NC(=O)[C@H](CC(=O)O)NC(=O)[C@H](CC(=O)O)NC(=O)CCc1cc(-c2ccc(-c3ccccc3)cc2)no1]

Formula (20)

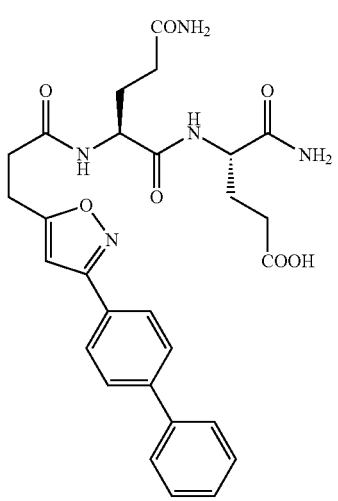 [SMILES: NC(=O)CC[C@H](NC(=O)CCc1cc(-c2ccc(-c3ccccc3)cc2)no1)C(=O)N[C@@H](CCC(=O)O)C(N)=O]

Formula (21)

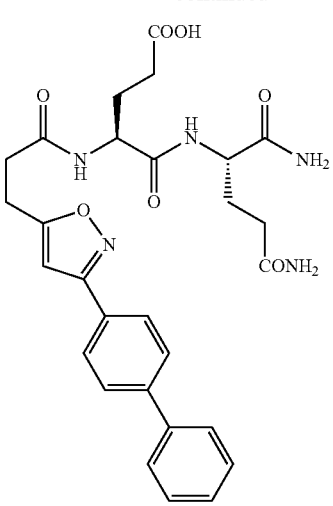 [SMILES: NC(=O)CC[C@H](NC(=O)[C@H](CCC(=O)O)NC(=O)CCc1cc(-c2ccc(-c3ccccc3)cc2)no1)C(N)=O]

Formula (22)

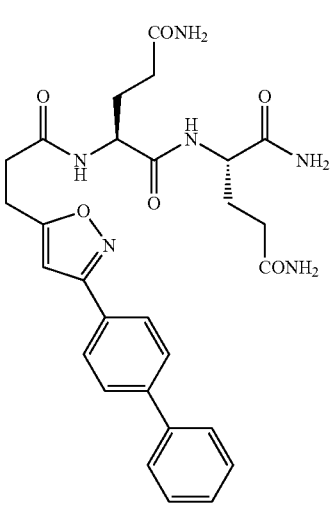 [SMILES: NC(=O)CC[C@H](NC(=O)[C@H](CCC(N)=O)NC(=O)CCc1cc(-c2ccc(-c3ccccc3)cc2)no1)C(N)=O]

Formula (23)

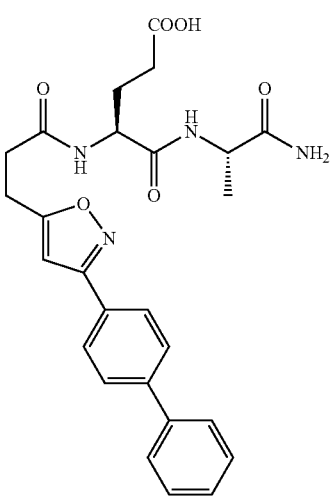 [SMILES: C[C@H](NC(=O)[C@H](CCC(=O)O)NC(=O)CCc1cc(-c2ccc(-c3ccccc3)cc2)no1)C(N)=O]

The inhibition constant Ki of these compounds has been determined according to the protocol described by Devel et al, 2006, J. Biol. Chem. (7).

The Ki values obtained are reported in table I.

It will be recalled that, the lower the Ki of a compound, the higher the inhibitory potential of said compound with respect to the target selected.

Compound (3) of this first subfamily corresponds to RXP470 having undergone removal of the substituted phosphinic group (R—PO$_2$—CH$_2$).

When comparing the Ki of compound (3) and that of the RXP470 compound (which is also reported in table I), it is noted that the selectivity of compound (3) with respect to the various MMPs is lower than that of the RXP470 compound; compound (3) is in fact quite a powerful inhibitor of MMPs 2, 3, 10, 12 and 13.

It is also noted that the inhibitory potential of compound (3) remains quite high with respect to MMP-12. This compound (3) therefore belongs to a new family of compounds which, after optimization of their chemical structure, would make it possible to gain access to selective inhibitors of MMP-12.

Thus, surprisingly, by removing the phosphinic part in the RXP470 compound and by varying the nature of the substituents R$_1$, R$_2$ and R$_3$, and also their various L or D or (S) or (R) configurations, MMP-12 inhibitors are obtained.

Even further, certain compounds of this series have comparable inhibitory powers toward three MMPs, MMP-10, MMP-12 and MMP-13, making these inhibitors active ingredients that can be used for the production of a medicament for treating pathological conditions in which these MMPs are overexpressed.

The second family of compounds of the invention is that in which the ring A is an isoxazole heterocycle where W is N, X is O and n is equal to 1.

These compounds have the following formula (1-B):

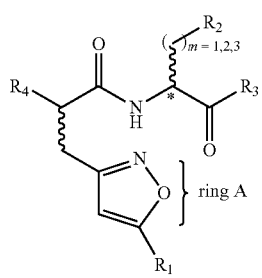

Formula (1-B)

in which:

n=1,

W is N,

X is O,

R$_1$ is a phenyl, biphenyl or 3'-chlorobiphenyl group, m is an integer between 1 and 3 inclusive, when m is 1 or 3, R$_2$ is a carboxylic acid group, and when m is 2, R$_2$ is a carboxylic acid group or a carboxamide group, R$_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said R$_3$ group being bonded to the carbonyl group of formula (1-B) via an amino function, and R$_4$ is H or a carboxymethyl group —CH$_2$COOH.

The diastereoisomers and enantiomers of the compounds of this second family are also part of the invention.

The preferred compound of this second family of compounds of the invention is the compound having the following formula (25):

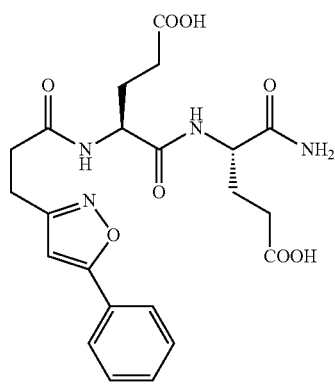

Formula (25)

The compounds having the following formulae (24), (26) and (27) have also been synthesized:

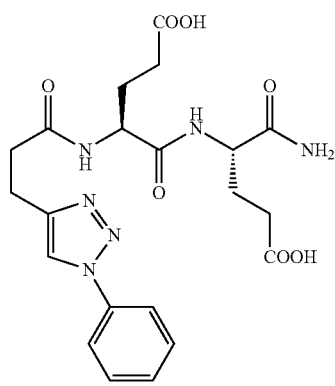 [SMILES: NC(=O)[C@H](CCC(=O)O)NC(=O)[C@H](CCC(=O)O)NC(=O)CCc1cn(-c2ccccc2)nn1]

Formula (24)

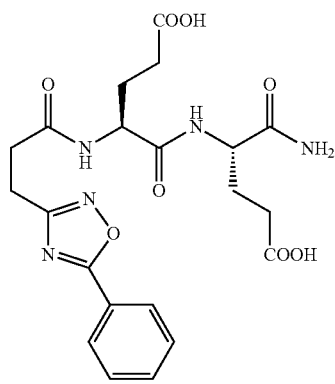 [SMILES: NC(=O)[C@H](CCC(=O)O)NC(=O)[C@H](CCC(=O)O)NC(=O)CCc1noc(-c2ccccc2)n1]

Formula (26)

-continued

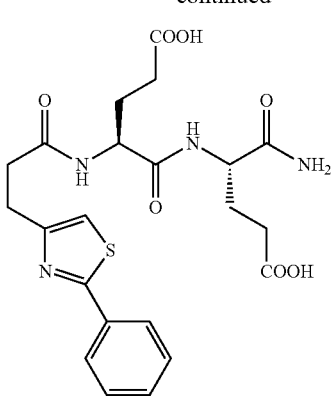

Formula (27)

In these compounds, the nature of the heteroatoms and the number thereof in the ring A, which is, as in the compound of formula (25), a 5-atom ring substituted in position 3 with a phenyl group, have been varied.

The Ki values of these compounds have been determined and are reported in table I.

It is seen from table I that the compounds of formulae (24), (26) and (27) do not have any inhibitory activity, whereas the compounds of the first family and that of formula (25) are MMP inhibitors.

This shows that the nature of the ring A plays a role in the inhibitory power toward MMPs.

Other compounds in which the ring A is a benzene ring have thus been synthesized.

Thus, in the third family of compounds of formula (1), the ring A is a benzene ring, i.e. W and X are C and n=2.

Furthermore, in these compounds, m=2.

These compounds have the following general formula (1-C):

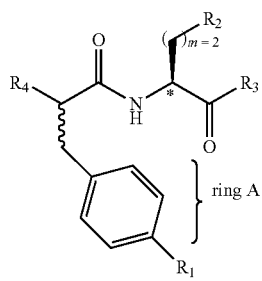

Formula (1-C)

in which:

$R_1$ is chosen from an iodine atom or a phenyl, biphenyl, 3'-chlorobiphenyl, phenoxy, phenoxymethyl, phenylethynyl, pyrimidine, 1-methyl-1H-pyrazole, 5-methyl-1,2,4-oxadiazole, 1,2,3-thiadiazole, 1H-pyrrole, thiazole, thiophene or 3a,7a-dihydrobenzo[d]thiazole group, m=2, $R_2$ is a carboxylic acid group, and $R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$ and said $R_3$ group being bonded to the carbonyl group of formula (1-C) via an amino function, and $R_4$ is H or a carboxymethyl group —CH$_2$COOH.

The diastereoisomers of these compounds are also part of the invention.

The preferred compounds of this third family have the following formulae (28) to (39):

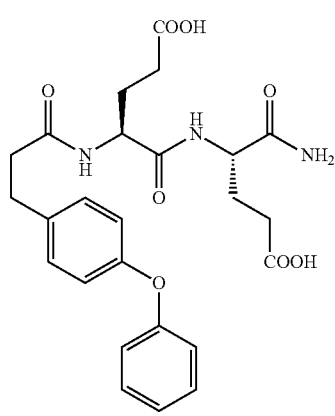 [SMILES: NC(=O)[C@H](CCC(=O)O)NC(=O)[C@H](CCC(=O)O)NC(=O)CCc1ccc(Oc2ccccc2)cc1]

Formula (28)

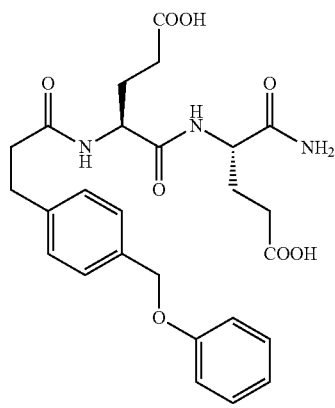 [SMILES: NC(=O)[C@H](CCC(=O)O)NC(=O)[C@H](CCC(=O)O)NC(=O)CCc1ccc(COc2ccccc2)cc1]

Formula (29)

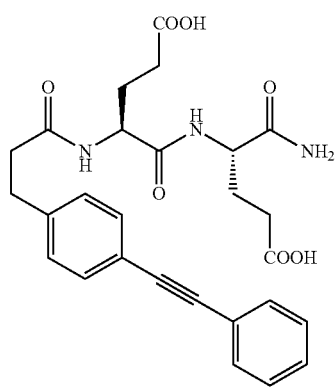 [SMILES: NC(=O)[C@H](CCC(=O)O)NC(=O)[C@H](CCC(=O)O)NC(=O)CCc1ccc(C#Cc2ccccc2)cc1]

Formula (30)

Formula (31)
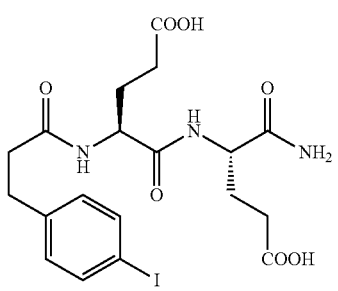 [SMILES: NC(=O)[C@H](CCC(=O)O)NC(=O)[C@H](CCC(=O)O)NC(=O)CCc1ccc(I)cc1]
Formula (32)
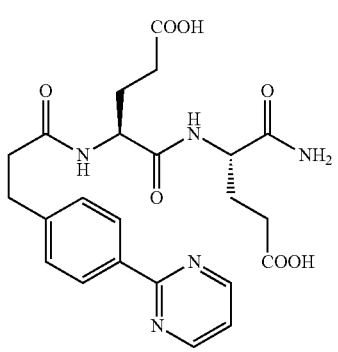 [SMILES: NC(=O)[C@H](CCC(=O)O)NC(=O)[C@H](CCC(=O)O)NC(=O)CCc1ccc(-c2ncccn2)cc1]
(Formula 33)
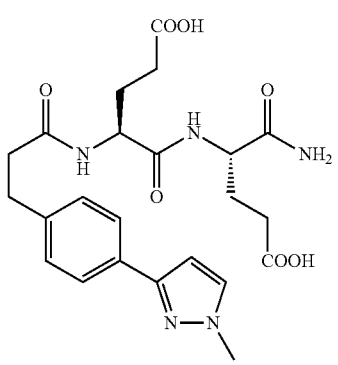 [SMILES: Cn1ccc(-c2ccc(CCC(=O)N[C@@H](CCC(=O)O)C(=O)N[C@@H](CCC(=O)O)C(N)=O)cc2)n1]
Formula (34)
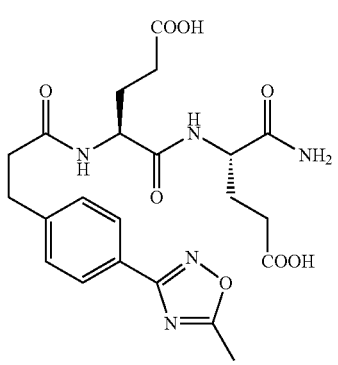
Formula (35)
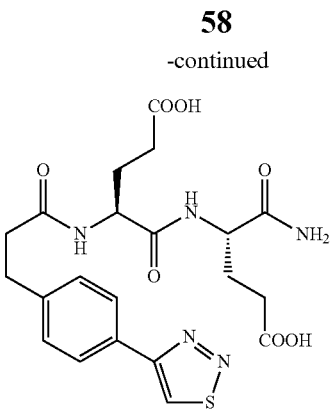
Formula (36)
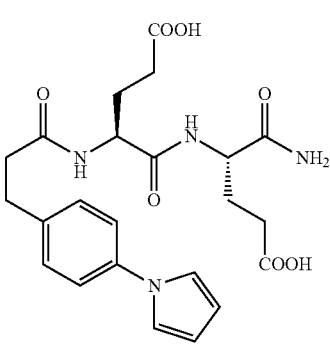 [SMILES: "COOH" ; CC[C@H](NC(=O)CCc1ccc(-n2cccc2)cc1)C(=O)N[C@@H](CCC(=O)O)C(N)=O]
Formula (37)
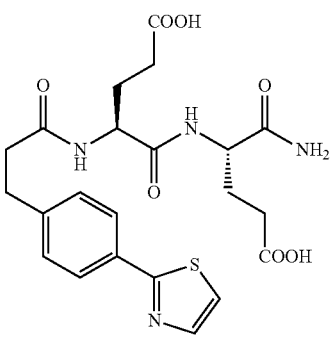 [SMILES: "COOH" ; CC[C@H](NC(=O)CCc1ccc(-c2nccs2)cc1)C(=O)N[C@@H](CCC(=O)O)C(N)=O]
Formula (38)
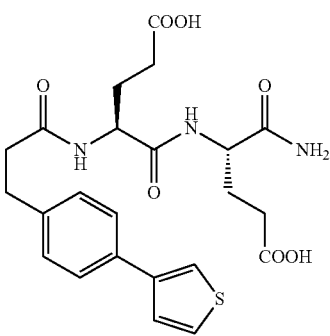 [SMILES: "COOH" ; CC[C@H](NC(=O)CCc1ccc(-c2ccsc2)cc1)C(=O)N[C@@H](CCC(=O)O)C(N)=O]

Formula (39)

The Ki values of these compounds have been determined and are reported in table I.

From the Ki values of these compounds, it is noted that, in certain cases, the inhibition constants are improved when the ring A is a phenyl ring.

Compounds in which the ring A is a phenyl ring, which is optionally itself substituted, have thus been synthesized.

The fourth subfamily of compounds of formula (1) of the invention is characterized by the presence of a ring A which is a benzene ring, i.e., in the ring A, W and X are C and n=2, and in that the $R_1$ group is a phenyl group, which is itself optionally substituted.

These compounds have the following general formula (1-D):

Formula (1-D)

in which:
$R_1$ is:
either an unsubstituted phenyl group ($R_1'$=H and $R_1''$=H),
or a phenyl group monosubstituted in position 3 with an amino group ($R_1'$=NH$_2$, $R_1''$=H) or with a hydroxyl group ($R_1'$=OH, $R_1''$=H) or with a nitro group ($R_1'$=NO$_2$, $R_1''$=H) or with a carboxyl group ($R_1'$=COOH, $R_1''$=H) or with a chlorine atom ($R_1'$=Cl, $R_1''$=H) or with a methoxy group ($R_1'$=OMe, $R_1''$=H) or with a hydroxymethyl group ($R_1'$=CH$_2$OH, $R_1''$=H),
or a phenyl group disubstituted in positions 3 and 5 with a chlorine atom ($R_1'$=Cl and $R_1''$=Cl),
m=2,
$R_2$ is a carboxylic acid group, and $R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said $R_3$ group being bonded to the carbonyl group of formula (1-D) via an amino function, and $R_4$ is H or a carboxymethyl group —CH$_2$COOH.

The diastereoisomers of these groups are also part of the invention.

In these compounds, the asymmetric carbon (C*) carrying the —CH$_2$—CH$_2$—R$_2$ group is of the (S) configuration.

The preferred compounds of this fourth family have the following formulae (40) and (42) to (60):

Formula (40)

Formula (42)

Formula (43)

Formula (44)
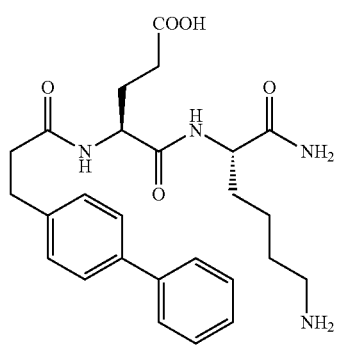 [SMILES: NCCCC[C@H](NC(=O)[C@H](CCC(=O)O)NC(=O)CCc1ccc(-c2ccccc2)cc1)C(N)=O]
Formula (45)
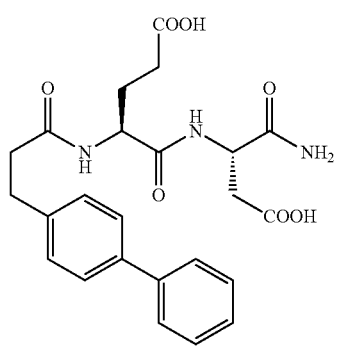 [SMILES: NC(=O)[C@H](CC(=O)O)NC(=O)[C@H](CCC(=O)O)NC(=O)CCc1ccc(-c2ccccc2)cc1]
Formula (46)
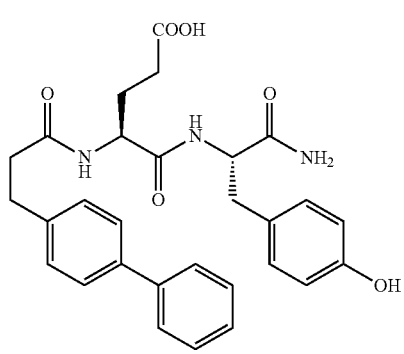 [SMILES: NC(=O)[C@H](Cc1ccc(O)cc1)NC(=O)[C@H](CCC(=O)O)NC(=O)CCc1ccc(-c2ccccc2)cc1]
Formula (47)
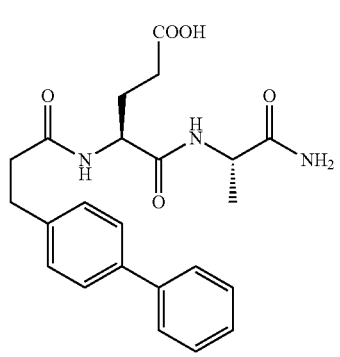 [SMILES: C[C@H](NC(=O)[C@H](CCC(=O)O)NC(=O)CCc1ccc(-c2ccccc2)cc1)C(N)=O]
Formula (48)
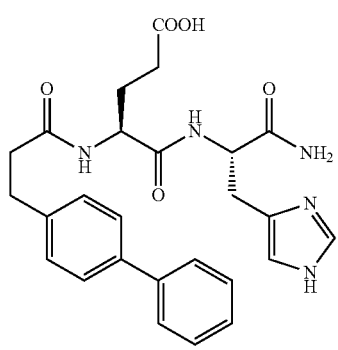 [SMILES: NC(=O)[C@H](Cc1c[nH]cn1)NC(=O)[C@H](CCC(=O)O)NC(=O)CCc1ccc(-c2ccccc2)cc1]
Formula (49)
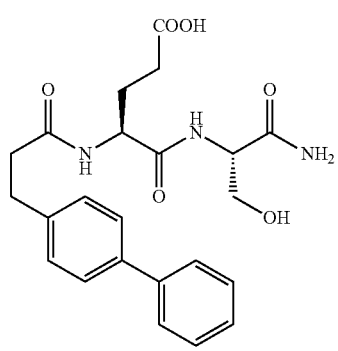 [SMILES: NC(=O)[C@H](CO)NC(=O)[C@H](CCC(=O)O)NC(=O)CCc1ccc(-c2ccccc2)cc1]
Formula (50)
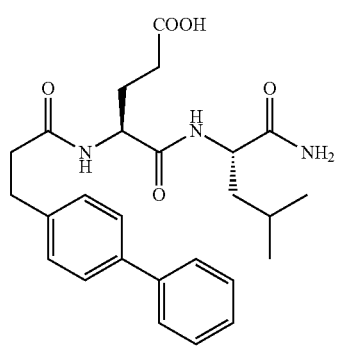 [SMILES: CC(C)C[C@H](NC(=O)[C@H](CCC(=O)O)NC(=O)CCc1ccc(-c2ccccc2)cc1)C(N)=O]
Formula (51)
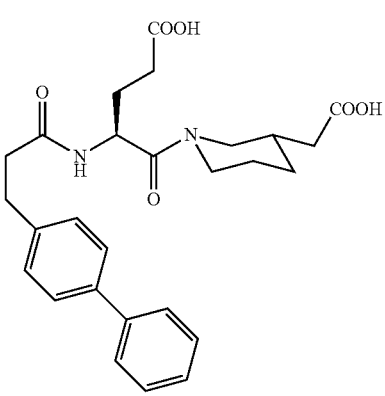

Formula (52)
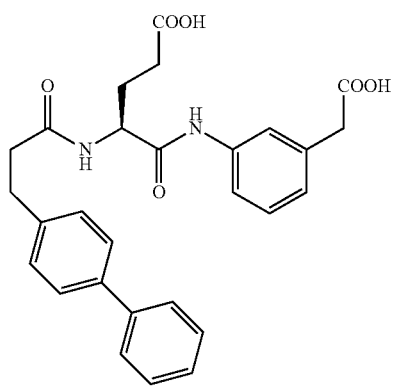 [SMILES: O=C(O)CC[C@H](NC(=O)CCc1ccc(-c2ccccc2)cc1)C(=O)Nc1cccc(CC(=O)O)c1]
Formula (53)
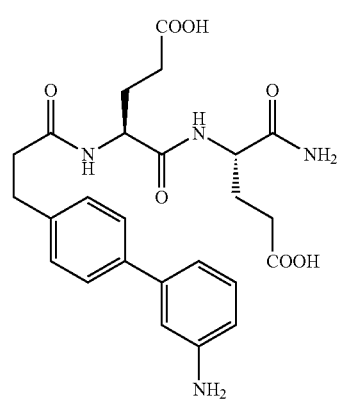
Formula (54)
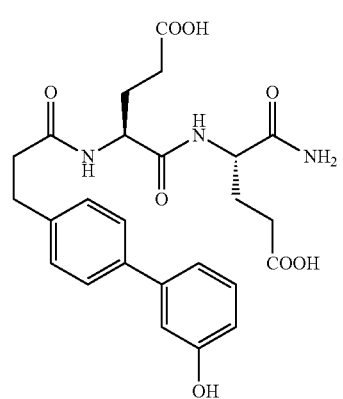 [SMILES: NC(=O)[C@H](CCC(=O)O)NC(=O)[C@H](CCC(=O)O)NC(=O)CCc1ccc(-c2cccc(O)c2)cc1]
Formula (55)
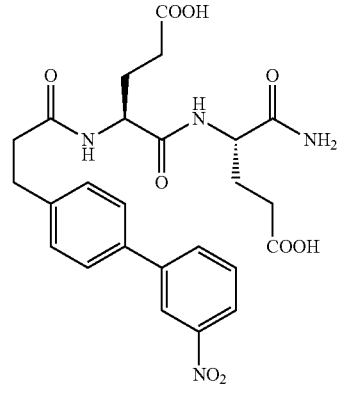 [SMILES: "COOH" ; CC[C@H](NC(=O)CCc1ccc(-c2cccc([N+](=O)[O-])c2)cc1)C(=O)N[C@@H](CCC(=O)O)C(N)=O]
Formula (56)
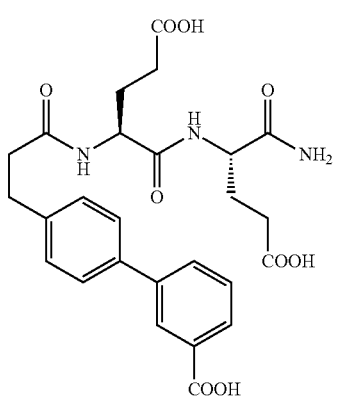 [SMILES: NC(=O)[C@H](CCC(=O)O)NC(=O)[C@H](CCC(=O)O)NC(=O)CCc1ccc(-c2cccc(C(=O)O)c2)cc1]
Formula (57)
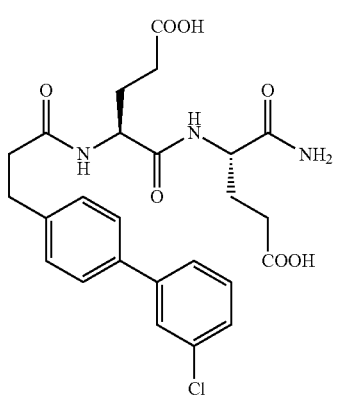 [SMILES: NC(=O)[C@H](CCC(=O)O)NC(=O)[C@H](CCC(=O)O)NC(=O)CCc1ccc(-c2cccc(Cl)c2)cc1]
Formula (58)
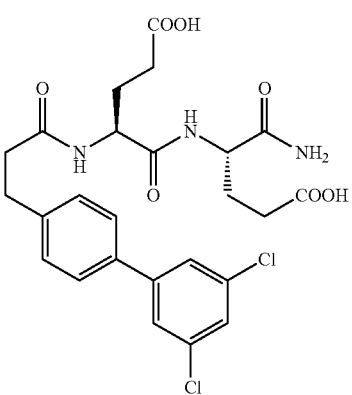 [SMILES: NC(=O)[C@H](CCC(=O)O)NC(=O)[C@H](CCC(=O)O)NC(=O)CCc1ccc(-c2cc(Cl)cc(Cl)c2)cc1]
Formula (59)
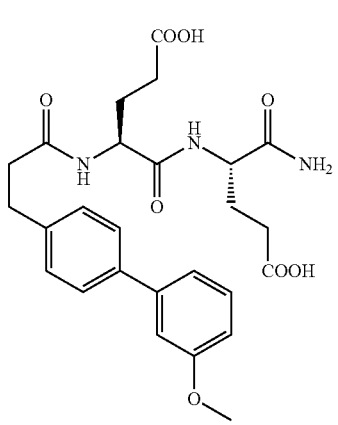 [SMILES: COc1cccc(-c2ccc(CCC(=O)N[C@@H](CCC(=O)O)C(=O)N[C@@H](CCC(=O)O)C(N)=O)cc2)c1]

Formula (60)

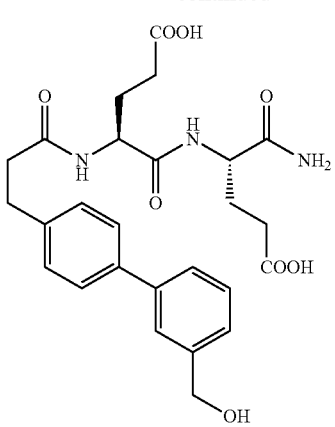 [SMILES: NC(=O)[C@H](CCC(=O)O)NC(=O)[C@H](CCC(=O)O)NC(=O)CCc1ccc(-c2cccc(CO)c2)cc1]

The Ki values of these compounds have been measured and are reported in table I.

It is seen from table I that these compounds exhibit improved selectivity with respect to MMP-12 or with respect to MMPs 2 and 12 or with respect to MMPs 3 and 12.

These compounds can therefore advantageously be used as a medicament for treating diseases in which these MMPs are overexpressed.

The fifth family of compounds of the invention is the family of compounds in which the ring A is a phenyl ring substituted with a biphenyl group, the substituents $R_2$, $R_3$ and $R_4$ being variable.

These compounds have the following formula (1-E):

Formula (1-E)

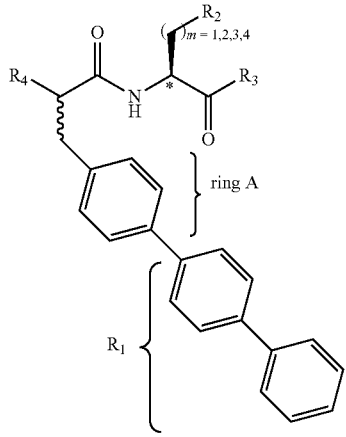

in which:

m is 1, 2, 3 or 4, when m=4, $R_2$ is an amino group, when m=1 or 2 or 3, $R_2$ is a carboxylic acid group, when m=2, $R_2$ is a carboxamide group, when m=1, $R_2$ is a 4-hydroxyphenyl group or a 1H-imidazole or hydroxyl or isopropyl or methyl, $R_3$ is chosen from a glutamate group of L or D configuration, a homoglutamate group, an aspartate group, a glutamine group, an alanine group, a lysine group, a tyrosine group, a histidine group, a serine group or a leucine group, it being possible for the terminal carboxylic functions of said amino acids to be carboxamide functions —C(=O)NH$_2$, or a carboxymethylpiperidine group, a carboxymethyl-3-aminophenyl group or an amino group, said $R_3$ group being bonded to the carbonyl group of formula (1-E) via an amino function, and $R_4$ is H or a carboxymethyl group —CH$_2$COOH.

The diastereoisomers and enantiomers of these compounds are also part of the invention.

The preferred compounds of this family are the compounds having the following formulae (61) to (79):

Formula (61)

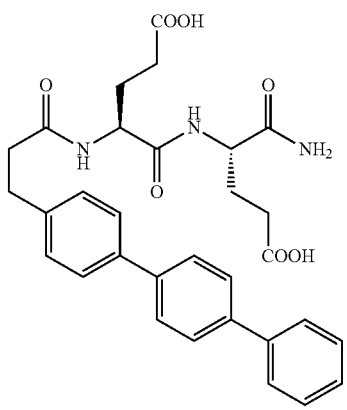 [SMILES: NC(=O)[C@H](CCC(=O)O)NC(=O)[C@H](CCC(=O)O)NC(=O)CCc1ccc(-c2ccc(-c3ccccc3)cc2)cc1]

Formula (62)

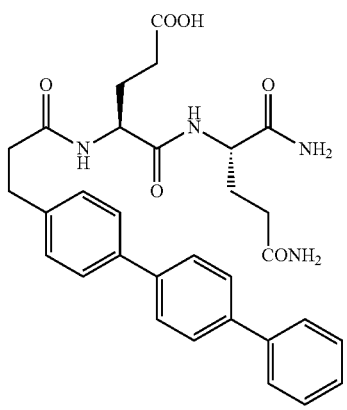 [SMILES: NC(=O)CC[C@H](NC(=O)[C@H](CCC(=O)O)NC(=O)CCc1ccc(-c2ccc(-c3ccccc3)cc2)cc1)C(N)=O]

Formula (63)

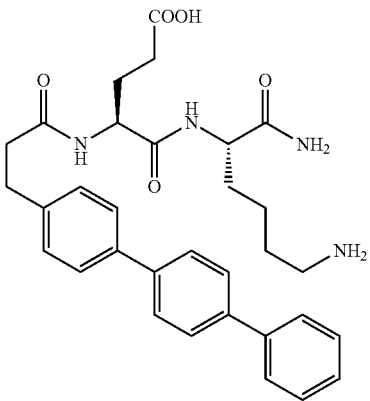 [SMILES: NCCCC[C@H](NC(=O)[C@H](CCC(=O)O)NC(=O)CCc1ccc(-c2ccc(-c3ccccc3)cc2)cc1)C(N)=O]

Formula (64)
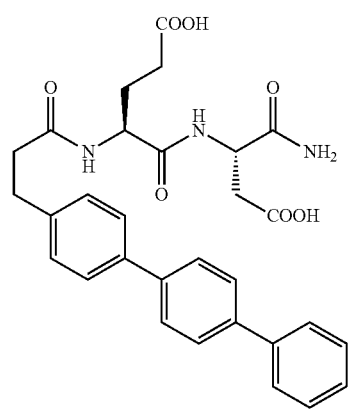 [SMILES: NC(=O)[C@H](CC(=O)O)NC(=O)[C@H](CCC(=O)O)NC(=O)CCc1ccc(-c2ccc(-c3ccccc3)cc2)cc1]
Formula (65)
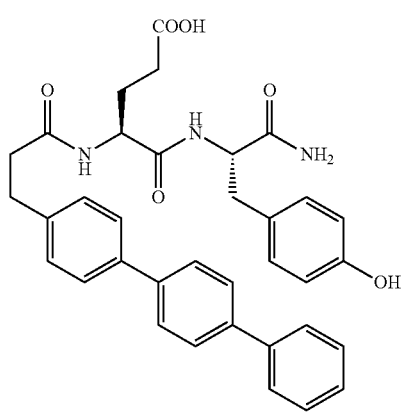 [SMILES: NC(=O)[C@H](Cc1ccc(O)cc1)NC(=O)[C@H](CCC(=O)O)NC(=O)CCc1ccc(-c2ccc(-c3ccccc3)cc2)cc1]
Formula (66)
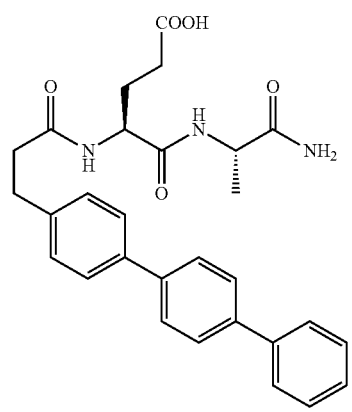 [SMILES: C[C@H](NC(=O)[C@H](CCC(=O)O)NC(=O)CCc1ccc(-c2ccc(-c3ccccc3)cc2)cc1)C(N)=O]
Formula (67)
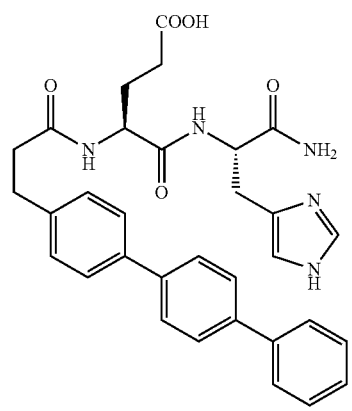 [SMILES: NC(=O)C(Cc1c[nH]cn1)NC(=O)[C@H](CCC(=O)O)NC(=O)CCc1ccc(-c2ccc(-c3ccccc3)cc2)cc1]
Formula (68)
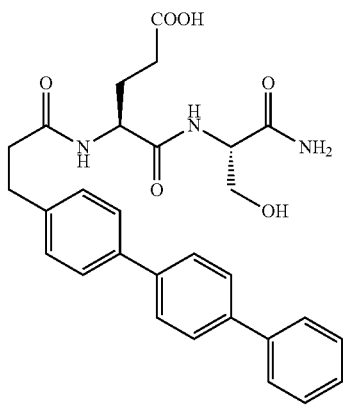 [SMILES: NC(=O)[C@H](CO)NC(=O)[C@H](CCC(=O)O)NC(=O)CCc1ccc(-c2ccc(-c3ccccc3)cc2)cc1]
Formula (69)
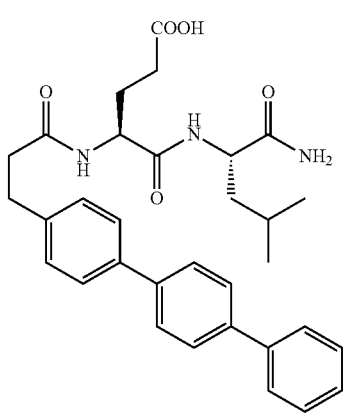 [SMILES: CC(C)C[C@H](NC(=O)[C@H](CCC(=O)O)NC(=O)CCc1ccc(-c2ccc(-c3ccccc3)cc2)cc1)C(N)=O]
Formula (70)
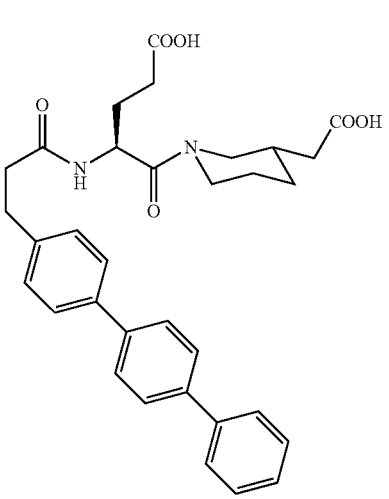

Formula (71)
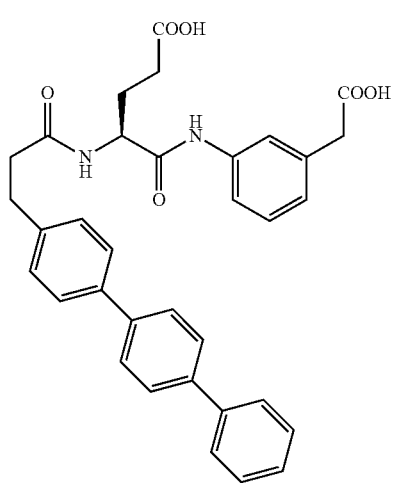 [SMILES: O=C(O)CC[C@H](NC(=O)CCc1ccc(-c2ccc(-c3ccccc3)cc2)cc1)C(=O)Nc1cccc(CC(=O)O)c1]
Formula (72)
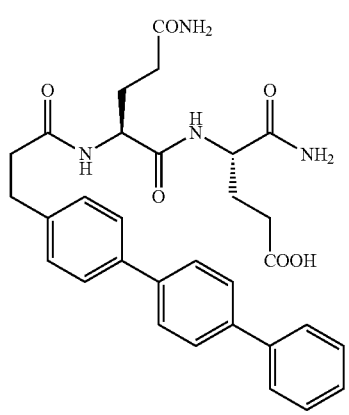 [SMILES: NC(=O)[C@H](CCC(=O)O)NC(=O)[C@H](CCC(=O)O)NC(=O)CCc1ccc(-c2ccc(-c3ccccc3)cc2)cc1]
Formula (73)
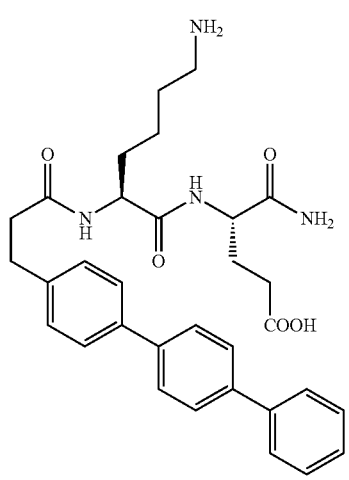 [SMILES: NCCCC[C@H](NC(=O)CCc1ccc(-c2ccc(-c3ccccc3)cc2)cc1)C(=O)N[C@@H](CCC(=O)O)C(N)=O]
Formula (74)
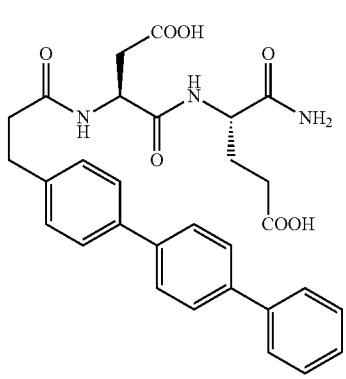 [SMILES: NC(=O)[C@H](CCC(=O)O)NC(=O)[C@H](CC(=O)O)NC(=O)CCc1ccc(-c2ccc(-c3ccccc3)cc2)cc1]
Formula (75)
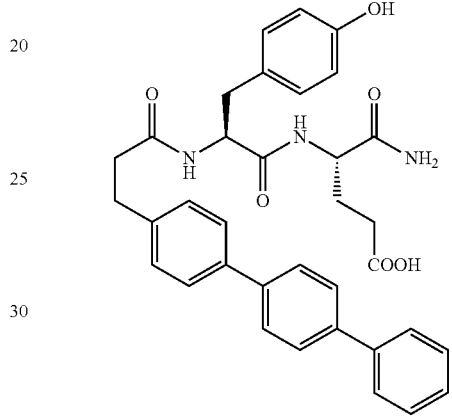
Formula (76)
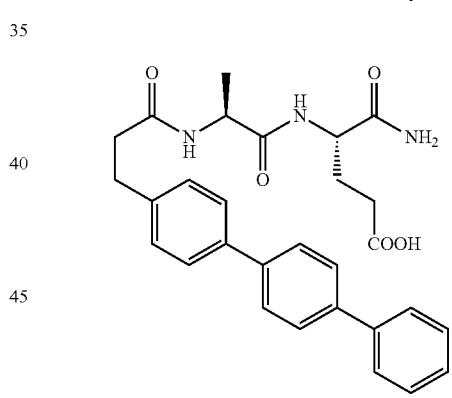
Formula (77)
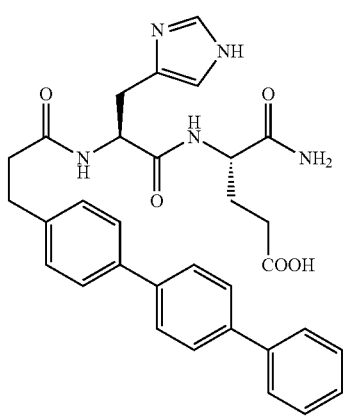 [SMILES: NC(=O)[C@H](CCC(=O)O)NC(=O)[C@H](Cc1c[nH]cn1)NC(=O)CCc1ccc(-c2ccc(-c3ccccc3)cc2)cc1]

Formula (78)

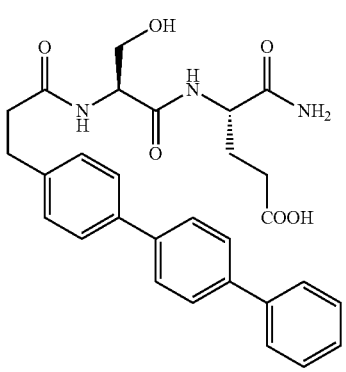 [SMILES: NC(=O)[C@H](CCC(=O)O)NC(=O)[C@H](CO)NC(=O)CCc1ccc(-c2ccc(-c3ccccc3)cc2)cc1]

Formula (79)

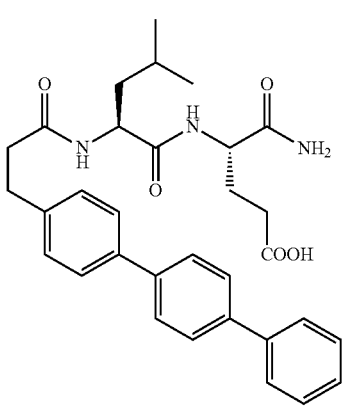 [SMILES: CC(C)C[C@H](NC(=O)CCc1ccc(-c2ccc(-c3ccccc3)cc2)cc1)C(=O)N[C@@H](CCC(=O)O)C(N)=O]

As indicated by the Ki values of these compounds, reported in table I, these compounds behave essentially as powerful inhibitors of MMP-12 and MMP-13. This series of compounds therefore has applications as an active ingredient for the production of a medicament for treating pathological conditions in which MMP-12 and MMP-13 are overexpressed.

However, when examining the Ki values of the compounds belonging to the third family (1C), but also those of the compounds belonging to the fourth family (1D) and to the fifth family (1E) of the invention, it is noted that the power and the selectivity of the compounds with respect to MMP-12 are improved not only when the ring A is a phenyl ring, but also when said ring is substituted with a thiophene heterocycle.

Compounds of formula (1) in which the ring A is a benzene ring, i.e. W and X are C and n=2, and in which $R_1$ is an unsubstituted or substituted thiophene ring, have therefore been synthesized.

These compounds have the following formula (1-F):

Formula (1-F)

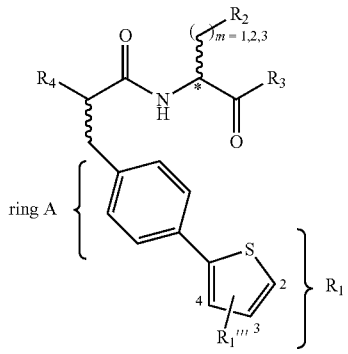

in which:

$R_1$ is:

either an unsubstituted thiophene ring ($R_1'''=H$), or a thiophene ring monosubstituted in position 2 with a group chosen from a methyl ($R_1'''=CH_3$), phenyl ($R_1'''=Ph$) or 3a,7a-dihydrobenzo[d]thiazole group, or a thiophene ring monosubstituted in position 3 with a group chosen from a methyl ($R_1'''=CH_3$) or phenyl ($R_1'''=Ph$) group, or a thiophene ring monosubstituted in position 4 with a methyl group ($R_1'''=CH_3$), m=1, 2 or 3, and $R_2$ is a carboxylic acid group or an imidazole group when m=1, or a carboxylic acid group or a carboxamide group when m=2, or a carboxylic acid group when m=3, $R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH_2, and said $R_3$ group being bonded to the carbonyl group of formula (1-F) via an amino function, and $R_4$ is H or a carboxymethyl group —CH_2COOH.

The diastereoisomers and enantiomers of these compounds are also part of the invention.

The preferred compounds of this family are the compounds having the following formulae (80) to (107):

Formula (80)

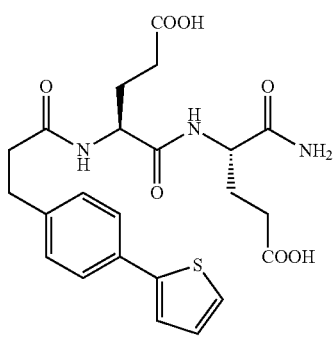 [SMILES: NC(=O)[C@H](CCC(=O)O)NC(=O)[C@H](CCC(=O)O)NC(=O)CCc1ccc(-c2cccs2)cc1]

Formula (81)

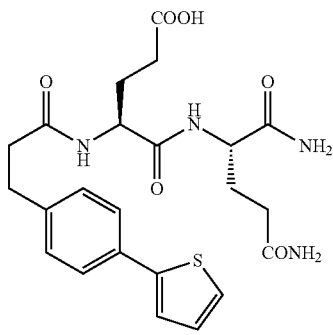 [SMILES: NC(=O)CC[C@H](NC(=O)[C@H](CCC(=O)O)NC(=O)CCc1ccc(-c2cccs2)cc1)C(N)=O]

Formula (82)
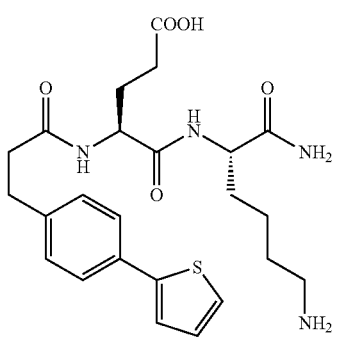 [SMILES: NCCCC[C@H](NC(=O)[C@H](CCC(=O)O)NC(=O)CCc1ccc(-c2cccs2)cc1)C(N)=O]
Formula (83)
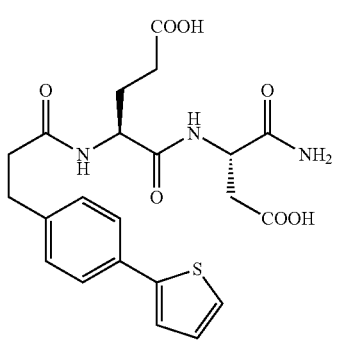 [SMILES: NC(=O)[C@H](CC(=O)O)NC(=O)[C@H](CCC(=O)O)NC(=O)CCc1ccc(-c2cccs2)cc1]
Formula (84)
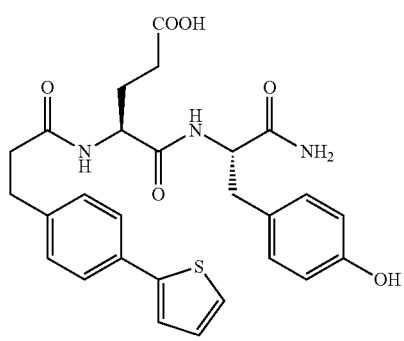 [SMILES: NC(=O)[C@H](Cc1ccc(O)cc1)NC(=O)[C@H](CCC(=O)O)NC(=O)CCc1ccc(-c2cccs2)cc1]
Formula (85)
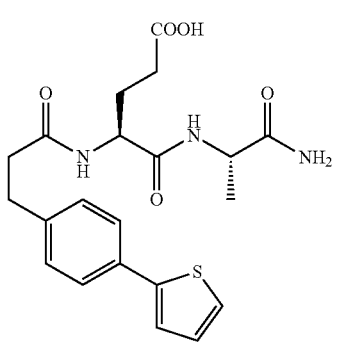 [SMILES: C[C@H](NC(=O)[C@H](CCC(=O)O)NC(=O)CCc1ccc(-c2cccs2)cc1)C(N)=O]
Formula (86)
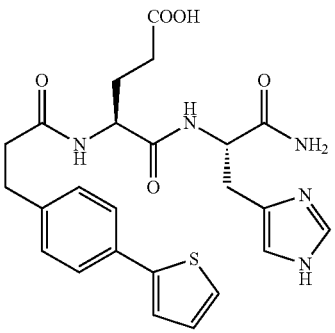 [SMILES: NC(=O)[C@H](Cc1c[nH]cn1)NC(=O)[C@H](CCC(=O)O)NC(=O)CCc1ccc(-c2cccs2)cc1]
Formula (87)
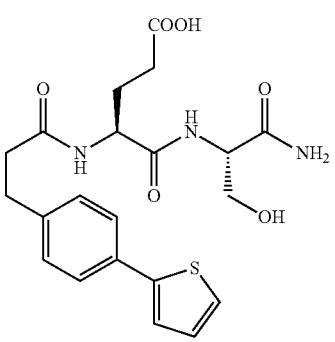 [SMILES: NC(=O)[C@H](CO)NC(=O)[C@H](CCC(=O)O)NC(=O)CCc1ccc(-c2cccs2)cc1]
Formula (88)
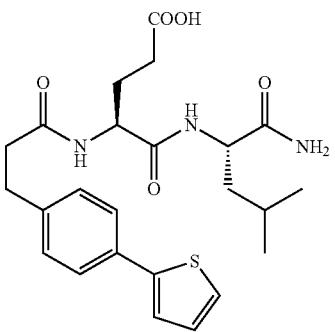 [SMILES: CC(C)C[C@H](NC(=O)[C@H](CCC(=O)O)NC(=O)CCc1ccc(-c2cccs2)cc1)C(N)=O]
Formula (89)
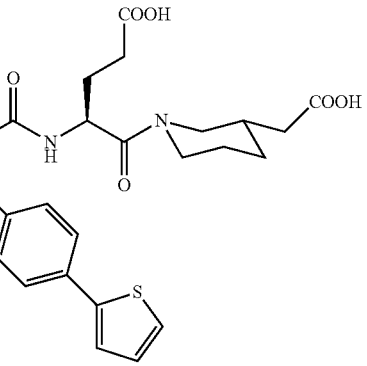

Formula (90)
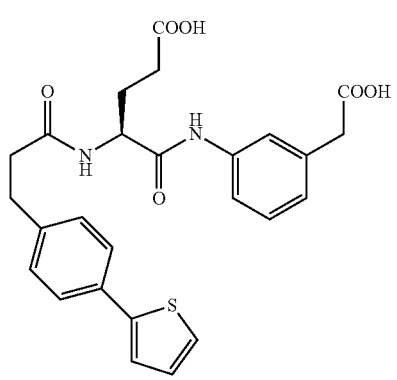
Formula (91)
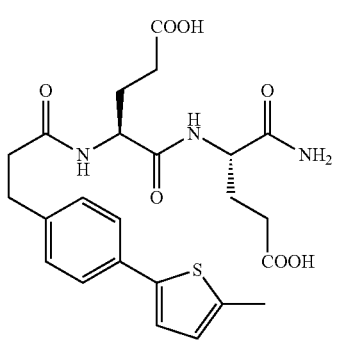 [SMILES: Cc1ccc(-c2ccc(CCC(=O)N[C@@H](CCC(=O)O)C(=O)N[C@@H](CCC(=O)O)C(N)=O)cc2)s1]
Formula (92)
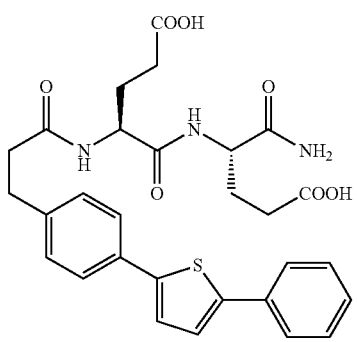 [SMILES: NC(=O)[C@H](CCC(=O)O)NC(=O)[C@H](CCC(=O)O)NC(=O)CCc1ccc(-c2ccc(-c3ccccc3)s2)cc1]
Formula (93)
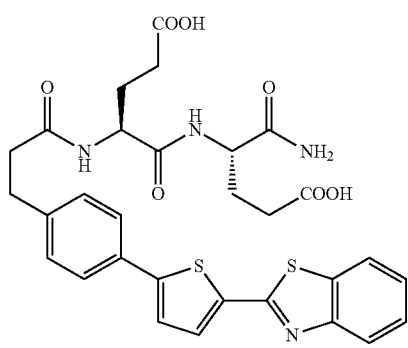 [SMILES: NC(=O)[C@H](CCC(=O)O)NC(=O)[C@H](CCC(=O)O)NC(=O)CCc1ccc(-c2ccc(-c3nc4ccccc4s3)s2)cc1]
Formula (94)
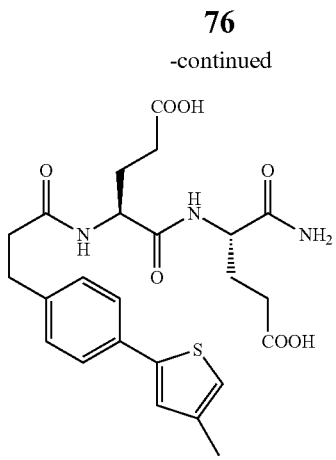
Formula (95)
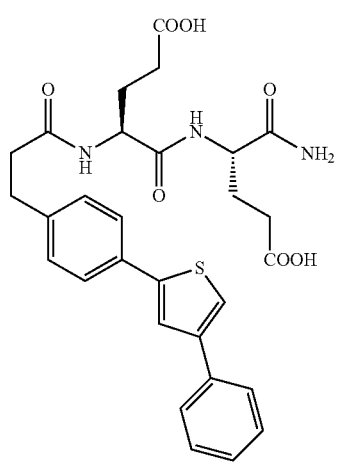 [SMILES: NC(=O)[C@H](CCC(=O)O)NC(=O)[C@H](CCC(=O)O)NC(=O)CCc1ccc(-c2cc(-c3ccccc3)cs2)cc1]
Formula (96)
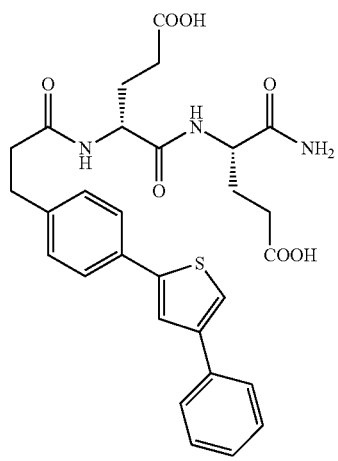

Formula (97)
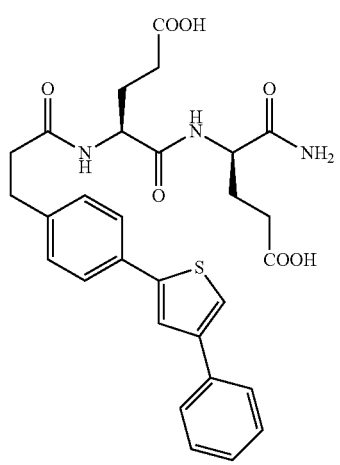
Formula (98)
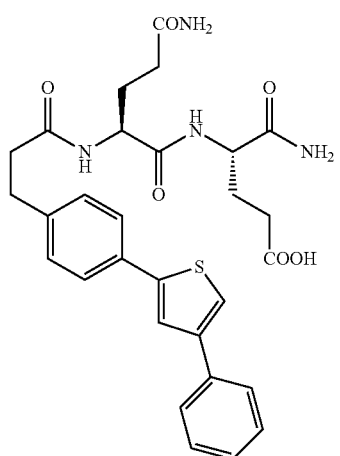
Formula (99)
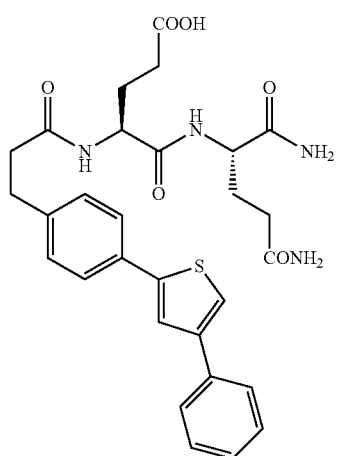
Formula (100)
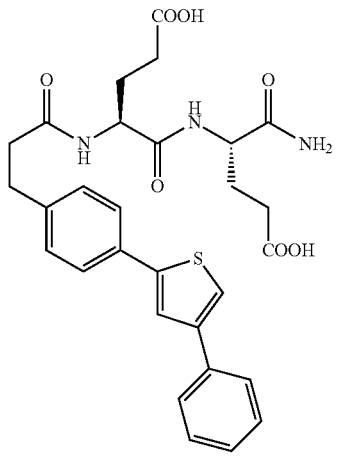 [SMILES: NC(=O)[C@H](CCC(=O)O)NC(=O)[C@H](CCC(=O)O)NC(=O)CCc1ccc(-c2cc(-c3ccccc3)cs2)cc1]
Formula (101)
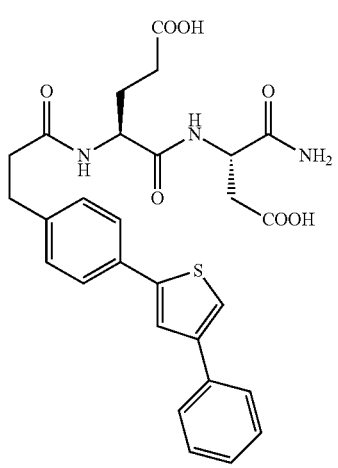 [SMILES: NC(=O)[C@H](CC(=O)O)NC(=O)[C@H](CCC(=O)O)NC(=O)CCc1ccc(-c2cc(-c3ccccc3)cs2)cc1]
Formula (102)
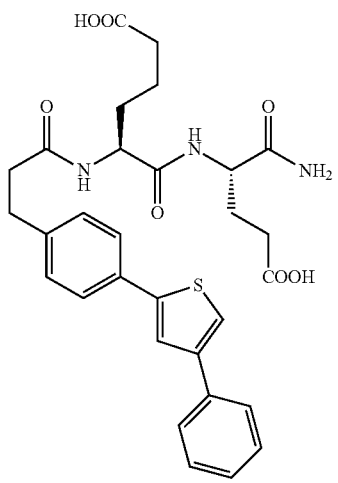 [SMILES: NC(=O)[C@H](CCC(=O)O)NC(=O)[C@H](CCCC(=O)O)NC(=O)CCc1ccc(-c2cc(-c3ccccc3)cs2)cc1]

Formula (103)
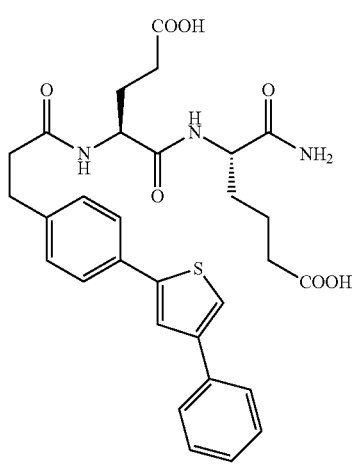 [SMILES: NC(=O)[C@H](CCCC(=O)O)NC(=O)[C@H](CCC(=O)O)NC(=O)CCc1ccc(-c2cc(-c3ccccc3)cs2)cc1]

Formula (104)
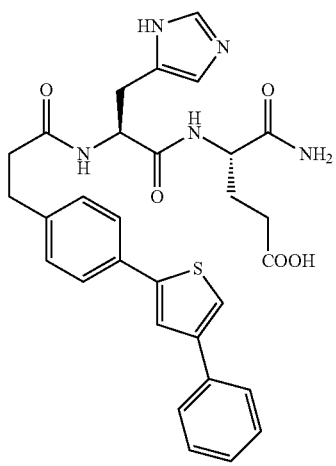 [SMILES: NC(=O)[C@H](CCC(=O)O)NC(=O)[C@H](Cc1cnc[nH]1)NC(=O)CCc1ccc(-c2cc(-c3ccccc3)cs2)cc1]

Formula (105)
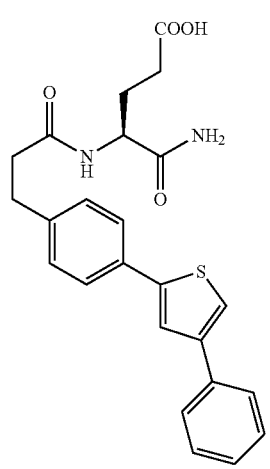 [SMILES: NC(=O)[C@H](CCC(=O)O)NC(=O)CCc1ccc(-c2cc(-c3ccccc3)cs2)cc1]

Formula (106)
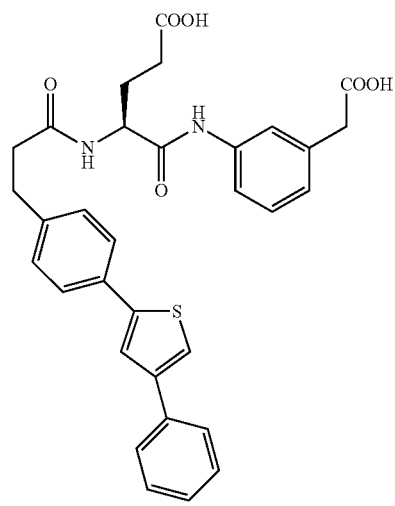

Formula (107)
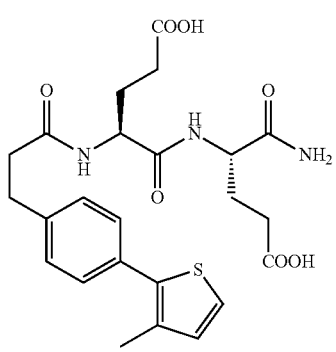 [SMILES: Cc1ccsc1-c1ccc(CCC(=O)N[C@@H](CCC(=O)O)C(=O)N[C@@H](CCC(=O)O)C(N)=O)cc1]

Formula (95bis)
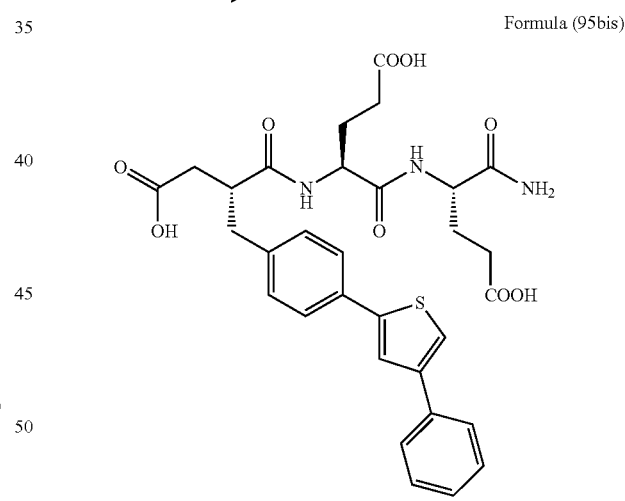

The inhibition constants of these compounds have been determined and are reported in table I.

It is seen from table I that these compounds have a high inhibitory power toward MMP-12 and MMP-8.

Thus, these compounds can be advantageously used for the production of medicaments for treating pathological conditions in which MMP-12 and MMP-8 are overexpressed.

However, it is especially noted, from table I, that the compounds having formula (1-F) in which the thiophene ring is substituted either in position 2 or in position 3 with a methyl ($R_1''' = CH_3$) or phenyl ($R_1'''' = Ph$) group are among the most powerful and most selective inhibitors of MMP-12.

Consequently, the most preferred compounds of the invention are the compounds having the following formula (1-F1):

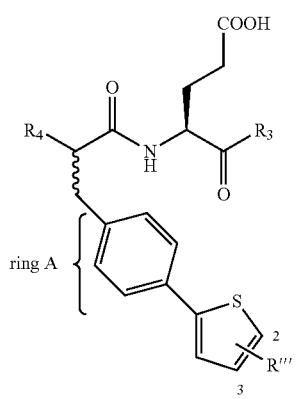

Formula (1-F1)

in which:
- $R_1'''$ is either in position 2 or in position 3 of the thiophene ring and is chosen from a methyl ($R_1'''=CH_3$) or phenyl ($R_1'''=Ph$) group, and
- $R_3$ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH$_2$, and said $R_3$ group being bonded to the carbonyl group of formula (1-F1) via an amino function, and
- $R_4$ is H or a carboxymethyl group —CH$_2$COOH.

The diastereoisomers of these compounds are also a subject of the invention.

Among the compounds of formula (1-F1), the compounds having the following formulae (91), (92), (95), (97), (99), (101), (103), (105), (106) and (95 bis) are preferred:

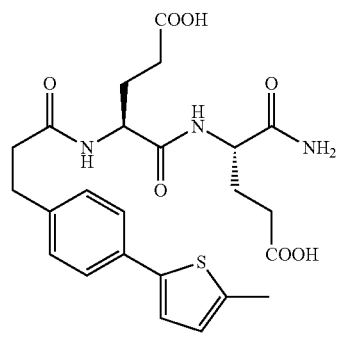

Formula (91)

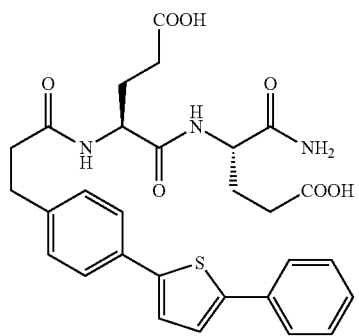

Formula (92)

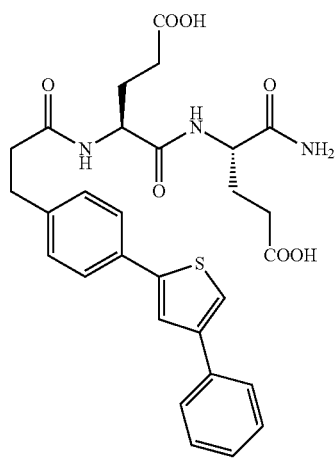

Formula (95)

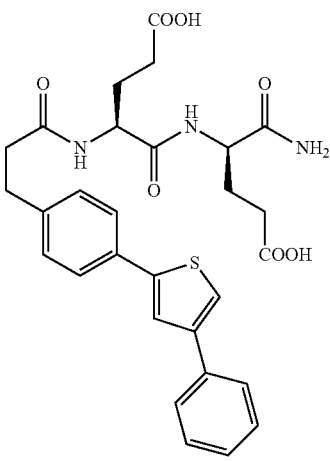

Formula (97)

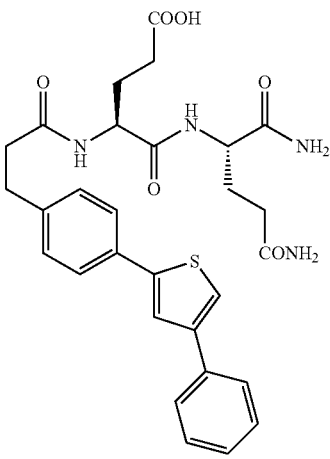

Formula (99)

Formula (101)
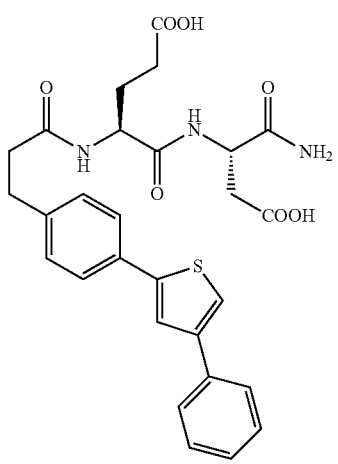
Formula (106)
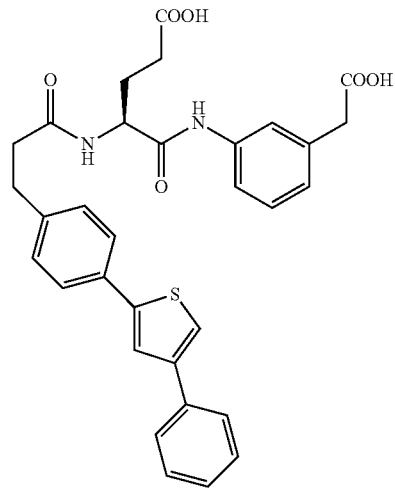
Formula (103)
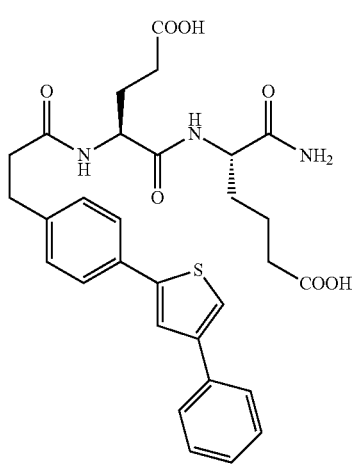
Formula (95bis)
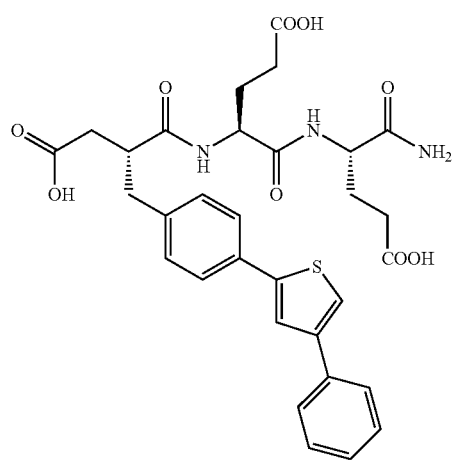 [SMILES: NC(=O)[C@H](CCC(=O)O)NC(=O)[C@H](CCC(=O)O)NC(=O)[C@@H](CC(=O)O)Cc1ccc(-c2cc(-c3ccccc3)cs2)cc1]
However, among these compounds of formula (1-F1), it is seen from table I that the compounds having formula (1-F1) in which $R_1'''$ is in position 3 of the thiophene ring and is a phenyl group ($R_1'''$=Ph) are the most powerful and most selective inhibitors with respect to MMP-12.
These compounds have the following formula (1-F2):
Formula (105)
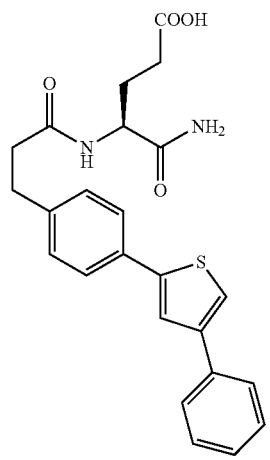
Formula (1-F2)
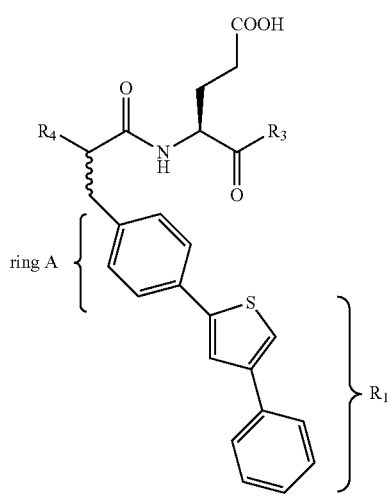

in which:

R₃ is chosen from an amino group; a carboxymethylpiperidine group; a carboxymethyl-3-aminophenyl group; a glutamate residue of L or D configuration, a homoglutamate residue, an aspartate residue, a glutamine residue, an alanine residue, a lysine residue, a tyrosine residue, a histidine residue, a serine residue or a leucine residue, it being possible for the terminal carboxylic functions of said amino acids to be carboxamide functions —C(=O)NH₂, and said R₃ group being bonded to the carbonyl group of formula (1-F2) via an amino function, and R₄ is H or a carboxymethyl group —CH₂COOH.

Thus, the quite particularly preferred compounds of the invention of formula 1-F2 are the compounds having the following formulae (95), (97), (99), (101), (103), (105), (106) and (95 bis):

Formula (95)

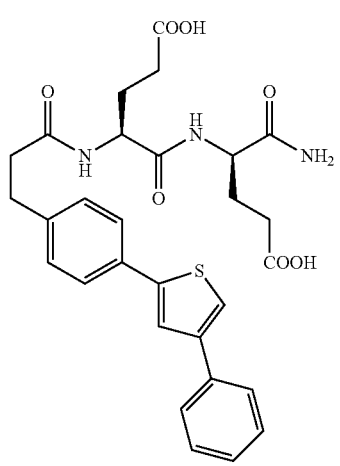

Formula (97)

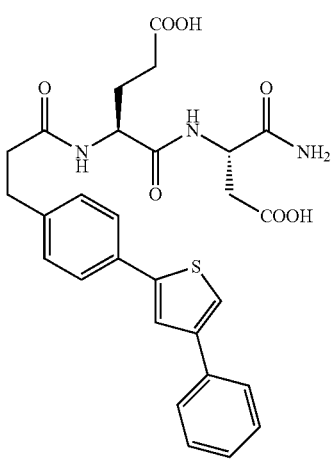

Formula (99)

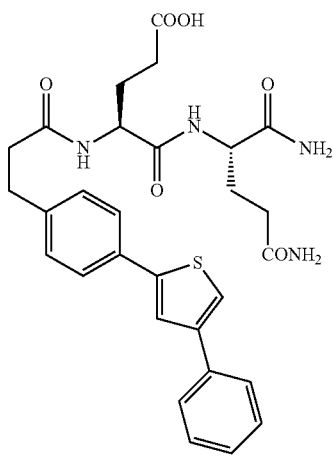

Formula (101)

Formula (103)
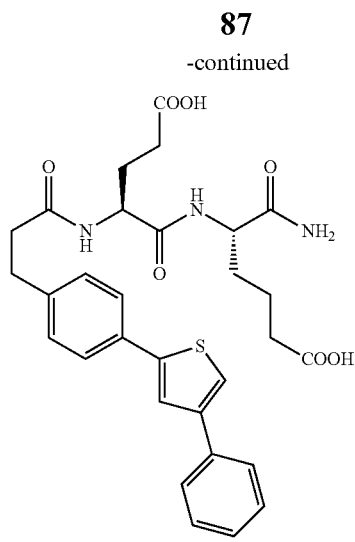
Formula (105)
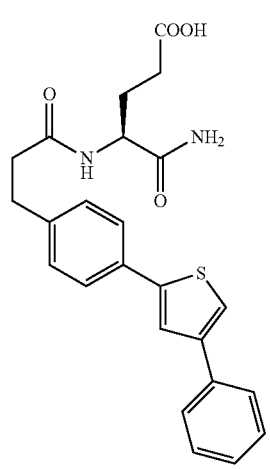
Formula (106)
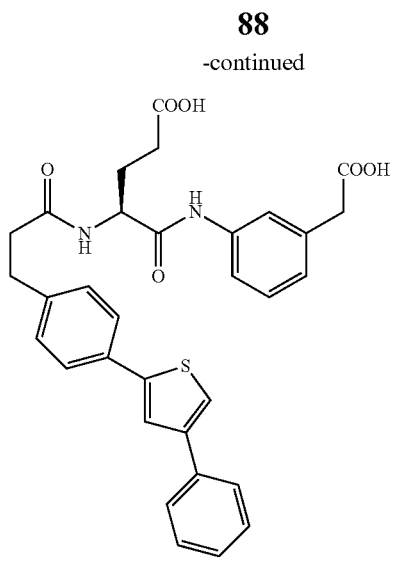
Formula (95bis)
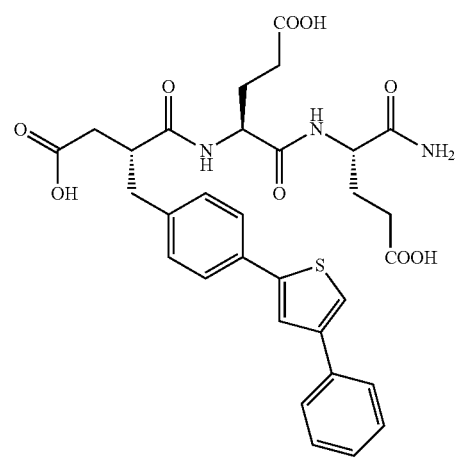
TABLE I
| | Ki (nM) | | | | | | | |
|---|---|---|---|---|---|---|---|---|
| | MMP-2h | MMP-3h | MMP-8h | MMP-9h | MMP-10h | MMP-12h | MMP-13h | MMP-14h |
| RXP470 | 72 | 58 | 77 | 850 | 8.3 | 0.2 | 13 | 80 |
| 3 | 76 | 62 | 181 | 565 | 47 | 8.3 | 40 | >1000 |
| 4 | 90 | 118 | 119 | 120 | 122 | 11.8 | 46 | >1000 |
| 5 | 112 | 240 | 552 | >1000 | 44 | 8.9 | 53 | >1000 |
| 6 | 403 | >1000 | >5000 | >5000 | 489 | 401 | 235 | >10000 |
| 7 | 538 | 897 | >1000 | >5000 | 111 | 268 | 114 | >10000 |
| 8 | 112 | 243 | 556 | >1000 | 35 | 11 | 30 | >1000 |
| 9 | 91 | 381 | 899 | >1000 | 520 | 64 | 35 | >5000 |
| 10 | 86 | 85 | 649 | >1000 | 93 | 59 | 18 | >1000 |
| 11 | >1000 | 302 | >1000 | >10000 | 556 | 254 | 191 | >10000 |
| 12 | 150 | 129 | 452 | >1000 | 51 | 8.2 | 52 | >5000 |
| 13 | >1000 | 575 | 638 | 605 | >5000 | 348 | 91 | 553 |
| 14 | 756 | >10000 | 112 | >1000 | >1000 | 119 | >1000 | >1000 |
| 15 | 762 | >10000 | 114 | >1000 | >5000 | 398 | >1000 | >1000 |
| 16 | 83 | 78 | 383 | >1000 | 114 | 3.4 | 60 | >1000 |
| 17 | 65 | 699 | >1000 | >1000 | >1000 | 53 | 36 | >5000 |
| 18 | 93 | 440 | 832 | >1000 | 196 | 8 | 30 | >1000 |
| 19 | 52 | 750 | >1000 | >1000 | 527 | 54 | 24 | >1000 |
| 20 | 834 | >1000 | >1000 | >1000 | >5000 | 412 | 234 | >10000 |
| 21 | 39.3 | 105 | 261 | >1000 | 256 | 5.4 | 49 | >1000 |
| 22 | >1000 | >10000 | >1000 | >1000 | >10000 | 830 | 436 | >10000 |
| 23 | 78 | 460 | 351 | >1000 | 276 | 11.2 | 80 | >1000 |
| 24 | >5000 | >1000 | >1000 | >1000 | >1000 | >1000 | >5000 | >5000 |
| 25 | >1000 | >5000 | 332 | >5000 | >1000 | 160 | 550 | >1000 |
| 26 | >5000 | >5000 | >5000 | >1000 | >5000 | >1000 | >1000 | >5000 |

TABLE I-continued

| | Ki (nM) | | | | | | | |
|---|---|---|---|---|---|---|---|---|
| | MMP-2h | MMP-3h | MMP-8h | MMP-9h | MMP-10h | MMP-12h | MMP-13h | MMP-14h |
| 27 | >1000 | >1000 | >1000 | >5000 | >5000 | >5000 | 900 | >5000 |
| 28 | >1000 | >5000 | >1000 | >10000 | >1000 | 856 | 309 | >1000 |
| 29 | >1000 | >10000 | >1000 | >1000 | >1000 | 469 | 117 | >5000 |
| 30 | >1000 | >1000 | 818 | 235 | >1000 | 154 | 598 | >1000 |
| 31 | >1000 | >5000 | 839 | >1000 | >1000 | 155 | >1000 | >1000 |
| 32 | >5000 | >1000 | >1000 | >1000 | >5000 | 969 | 641 | >1000 |
| 33 | >1000 | >10000 | >1000 | >1000 | >10000 | 797 | 518 | >1000 |
| 34 | >5000 | >1000 | >1000 | >5000 | >1000 | 887 | >1000 | >1000 |
| 35 | 442 | 281 | 231 | 199 | 679 | 158 | 212 | 438 |
| 36 | >1000 | >1000 | 373 | >1000 | >1000 | 59 | >1000 | >5000 |
| 37 | 657 | >5000 | >1000 | >1000 | >1000 | 369 | 240 | >1000 |
| 38 | 225 | 337 | 52 | 141 | 446 | 12 | 532 | 410 |
| 39 | 151 | 88 | 146 | 618 | 99 | 2.2 | 134 | 547 |
| 40 | 445 | >5000 | 226 | >1000 | >1000 | 18.6 | 689 | >5000 |
| 42 | 448 | >5000 | 285 | >1000 | >1000 | 48 | 884 | >1000 |
| 43 | 319 | >1000 | 657 | >1000 | >5000 | 306 | 259 | >5000 |
| 44 | >1000 | >10000 | 414 | >5000 | >5000 | 119 | >1000 | >5000 |
| 45 | 896 | >5000 | 233 | >1000 | >1000 | 37 | >1000 | >5000 |
| 46 | 632 | >10000 | 270 | >1000 | >1000 | 52 | >1000 | >5000 |
| 47 | >1000 | >10000 | 311 | >1000 | >1000 | 58 | >1000 | >5000 |
| 48 | 847 | >10000 | 339 | >5000 | >1000 | 75 | >1000 | >10000 |
| 49 | 790 | >5000 | 204 | >1000 | >1000 | 41 | >1000 | >1000 |
| 50 | >1000 | >50000 | 364 | >5000 | >5000 | 76 | >1000 | >5000 |
| 51 | >1000 | >10000 | 929 | >1000 | >10000 | 259 | >1000 | >5000 |
| 52 | 546 | >5000 | 63 | >1000 | 433 | 12.7 | >1000 | >1000 |
| 53 | >1000 | >1000 | >1000 | >1000 | >1000 | 190 | >1000 | >1000 |
| 54 | >10000 | >10000 | >1000 | >1000 | >1000 | 176 | >10000 | >10000 |
| 55 | >1000 | 878 | >1000 | 685 | >1000 | 73 | 436 | >5000 |
| 56 | >5000 | >10000 | >1000 | >1000 | >10000 | 91 | >5000 | >10000 |
| 57 | >1000 | >10000 | >1000 | >1000 | >5000 | 57 | >5000 | >10000 |
| 58 | >1000 | >1000 | >5000 | 391 | >1000 | 56 | >1000 | >1000 |
| 59 | >5000 | >10000 | >1000 | >5000 | >1000 | 35 | >5000 | >10000 |
| 60 | >5000 | >10000 | 809 | >5000 | >5000 | 52 | >5000 | >10000 |
| 61 | 53 | 74 | 132 | >1000 | 76 | 1.63 | 20 | >1000 |
| 62 | 45 | 244 | 452 | >1000 | 102 | 5.2 | 20 | >1000 |
| 63 | 110 | >1000 | 621 | >1000 | 447 | 14.3 | 55 | >1000 |
| 64 | 55 | 168 | 287 | >1000 | 35 | 3.3 | 23 | >5000 |
| 65 | 73 | 620 | 793 | >1000 | 119 | 6.6 | 33 | >1000 |
| 66 | 49 | 238 | 532 | >10000 | 130 | 2.2 | 16.4 | >10000 |
| 67 | 68 | 337 | 526 | >1000 | 168 | 10.2 | 36 | >1000 |
| 68 | 31 | 108 | 227 | >1000 | 71 | 3.5 | 16.6 | >1000 |
| 69 | 332 | 258 | 567 | >1000 | 382 | 7.8 | 81 | >5000 |
| 70 | 12 | 231 | 105 | >5000 | 421 | 4.7 | 17 | >1000 |
| 71 | 18.1 | 34 | 99 | 645 | 7.7 | 1.05 | 10.2 | 696 |
| 72 | 386 | 64 | >1000 | >5000 | >1000 | 134 | 180 | >5000 |
| 73 | 541 | 300 | >1000 | >10000 | >1000 | 254 | 97 | >10000 |
| 74 | 39 | 16 | 865 | >1000 | 430 | 10.5 | 13.5 | >1000 |
| 75 | >1000 | 252 | >5000 | >10000 | >1000 | 122 | 232 | >10000 |
| 76 | 854 | 142 | >1000 | >5000 | >10000 | 251 | 427 | >5000 |
| 77 | >1000 | >1000 | >1000 | >50000 | >5000 | 234 | 377 | >10000 |
| 78 | 729 | 116 | >1000 | >5000 | >5000 | 206 | 367 | >1000 |
| 79 | >1000 | 203 | >1000 | >100000 | >1000 | >1000 | 443 | >10000 |
| 80 | 142 | >1000 | 40 | >1000 | 373 | 8.6 | 321 | >1000 |
| 81 | 204 | >10000 | 48 | >1000 | 651 | 18.6 | 801 | >1000 |
| 82 | 234 | >10000 | 73 | >1000 | >1000 | 44 | >1000 | >1000 |
| 83 | 334 | >10000 | 49 | >1000 | 435 | 14.2 | >1000 | >1000 |
| 84 | 140 | >5000 | 41 | 859 | 514 | 20.9 | 584 | >1000 |
| 85 | 348 | >10000 | 62 | >5000 | 835 | 25.6 | >1000 | >1000 |
| 86 | 371 | >10000 | 63 | >1000 | >1000 | 34 | >1000 | >1000 |
| 87 | 147 | >10000 | 47 | >1000 | 742 | 16.4 | >1000 | >1000 |
| 88 | 298 | >10000 | 73 | >1000 | >1000 | 32 | >1000 | >1000 |
| 89 | 484 | >100000 | 94 | >1000 | >5000 | 124 | >1000 | >1000 |
| 90 | 116 | >1000 | 18 | 284 | 143 | 8 | 366 | 430 |
| 91 | 97 | >1000 | 10.3 | 242 | 353 | 1.84 | 564 | >1000 |
| 92 | 279 | 108 | 381 | 874 | 156 | 2.58 | 200 | >1000 |
| 93 | >1000 | >1000 | 307 | >1000 | 38.8 | 17 | 33 | >5000 |
| 94 | 868 | >1000 | 233 | >1000 | >1000 | 22 | >1000 | >10000 |
| 95 | >1000 | >1000 | 410 | >10000 | 872 | 1.92 | 684 | >1000 |
| 96 | >1000 | >10000 | >10000 | >1000 | >1000 | 144 | >1000 | >10000 |
| 97 | >1000 | >5000 | 694 | >5000 | 693 | 3.7 | 714 | >1000 |
| 98 | >5000 | >10000 | >10000 | >5000 | >10000 | 317 | >1000 | >10000 |
| 99 | >1000 | >10000 | >1000 | >5000 | >1000 | 5.4 | 522 | >1000 |
| 100 | 862 | >1000 | 559 | >1000 | >1000 | 15.1 | 559 | >1000 |
| 101 | >1000 | >5000 | 379 | >5000 | 571 | 2.56 | 933 | >1000 |

TABLE I-continued

| | Ki (nM) | | | | | | | |
|---|---|---|---|---|---|---|---|---|
| | MMP-2h | MMP-3h | MMP-8h | MMP-9h | MMP-10h | MMP-12h | MMP-13h | MMP-14h |
| 102 | >1000 | >10000 | >5000 | >5000 | >5000 | 56 | 635 | >10000 |
| 103 | >1000 | >5000 | 656 | >5000 | 845 | 2.9 | 563 | >1000 |
| 104 | >5000 | >10000 | >1000 | >5000 | >5000 | 40 | >1000 | >5000 |
| 105 | 377 | >1000 | 203 | >1000 | >1000 | 3.65 | 603 | >1000 |
| 106 | 339 | 791 | 675 | 396 | 318 | 4.3 | 132 | >1000 |
| 107 | >1000 | >10000 | 766 | >10000 | >1000 | 84 | >1000 | >5000 |

In this table I and also in table II below, "h" corresponds to human. All of the compounds have therefore been evaluated on human MMPs.

Moreover, the pseudopeptides of formulae (3), (14), (40), (61), (80), (95), (97), (99), (101), (103), (105), (106) and (95 bis) have also been evaluated on two other MMPs, MMP-1 h and MMP-7h.

The results obtained are given in table II below, and in table IV hereinafter:

TABLE II

| | Ki (nM) | | | | | | | | | |
|---|---|---|---|---|---|---|---|---|---|---|
| | MMP-1h | MMP-2h | MMP-3h | MMP-7h | MMP-8h | MMP-9h | MMP-10h | MMP-12h | MMP-13h | MMP-14h |
| 3 | >10000 | 76 | 62 | >1000 | 181 | 565 | 47 | 8.3 | 40 | >1000 |
| 14 | >10000 | 756 | >10000 | >10000 | 112 | >1000 | >1000 | 119 | >1000 | >1000 |
| 40 | >100000 | 445 | >5000 | >10000 | 226 | >1000 | >1000 | 18.6 | 689 | >5000 |
| 61 | >5000 | 53 | 74 | 502 | 132 | >1000 | 76 | 1.63 | 20 | >1000 |
| 80 | >100000 | 142 | >1000 | >1000 | 40 | >1000 | 373 | 8.6 | 321 | >1000 |
| 95 | >10000 | >1000 | >1000 | >1000 | 410 | >10000 | 872 | 1.92 | 684 | >1000 |
| 97 | >100000 | >1000 | >5000 | >10000 | 694 | >5000 | 693 | 3.7 | 714 | >1000 |
| 99 | >10000 | >1000 | >10000 | >10000 | >1000 | >5000 | >1000 | 5.4 | 522 | >1000 |
| 101 | >100000 | >1000 | >5000 | >100000 | 379 | >5000 | 571 | 2.56 | 933 | >1000 |
| 103 | >10000 | >1000 | >5000 | >5000 | 656 | >5000 | 845 | 2.9 | 563 | >1000 |
| 105 | >10000 | 377 | >1000 | >10000 | 203 | >1000 | >1000 | 3.65 | 603 | >1000 |
| 106 | >1000 | 339 | 791 | >1000 | 675 | 396 | 318 | 4.3 | 132 | >1000 |

The results reported in table II, and also in table IV, confirm firstly that the compounds of the invention are powerful MMP inhibitors, and in particular MMP-12 inhibitors, with Ki values of about one nanomolar, and secondly that the compounds of formulae (95), (97), (99), (101), (103), (105) and (95 bis) are compounds highly selective for MMP-12, with a selectivity factor F>100 with F=Ki MMP-x/Ki MMP-12.

Thus, the compounds of the invention can be used as a medicament, or as MMP inhibitors or else for the production of a medicament for treating disorders in which one or more MMPs are overexpressed.

More particularly, the compounds of the invention of formulae (61) to (79) can be used for the production of a medicament for treating pathological conditions in which MMP-12 and MMP-13 are overexpressed, and the compounds of formulae (80) to (90) can be used for the production of a medicament for treating pathological conditions in which MMP-12 and MMP-8 are overexpressed.

Even further, the compounds of formulae (95), (97), (99), (101), (103), (105), (106) and (95 bis) can be advantageously used as MMP-12 inhibitors and used for the production of a medicament for treating disorders in which MMP-12 is overexpressed, in particular for treating cancer, inflammatory diseases such as chronic obstructive pulmonary disease (COPD), arthritis, rhumatoid arthritis, atherosclerosis and ruptured aneurysms.

Another subject of the invention relates to compounds of formula (2) below, resulting from labeling of the compounds of formula (1) as defined previously with a label. The compounds of formula (2) correspond to the following formula:

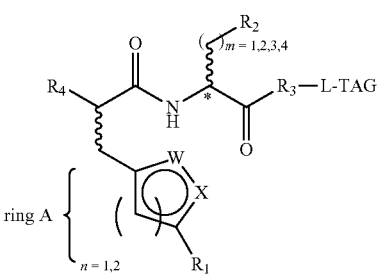

Formula (2)

in which n, m, W, X, $R_1$, $R_2$, $R_3$ and $R_4$ have the same meaning as above, and:

L is a spacer arm chosen from $C_1$-$C_{12}$ alkyl chains and glycol ethers in which the carbon-based chain contains from 2 to 12 carbon atoms, and TAG is a label, the $R_3$ group being bonded to the spacer arm L via a terminal carboxamide function —C(=O)$NH_2$.

The term "label" is intended to mean any entity capable of being detected by appropriate means, the labels used in the context of the invention typically corresponding to the labels used by those skilled in the art in the biology field for labeling molecules of biological interest, in particular in the context of carrying out a diagnosis.

The detectable physical property of the labels of the invention may be a specific reactivity with respect to an electromagnetic source such as a magnetic field, for instance via magnetic resonance imaging, or with respect to light radiation that can be focused, for instance via fluorescence imaging with fluorophores, or else with respect to nuclear radiation, for instance using isotopes.

The fluorophores used in the context of the invention may be aromatic fluorescent compounds of which the ?-? transitions are characterized by high fluorescence quantum yields and molar absorption coefficients, it being possible for said fluorophores to be chosen from rhodamine, fluorescein, pyronine, coumarin, benzophenone, anthrone, fluorenone, pyridine, quinoline, acridine, naphthalene, anthracene, naphthacene, pentacene, xanthene and derivatives thereof.

Various families of labels and various associated detection techniques known to those skilled in the art are described in the handbook Anti-Cancer Agents in *Medicinal Chemistry*, 2008, 8, 497-522. More specifically, reference may be made to the fluorophores cited in *Cytometry Part A* 69A: 863-871 (2006) and to the nanoparticles mentioned in the document *Anal. Bioanal. Chem.*, 384: 620-630 (2006).

According to one even more preferred embodiment, the TAG label may be chosen from:

the fluorophores as defined above, it being possible for the latter to correspond to one of the following formulae:

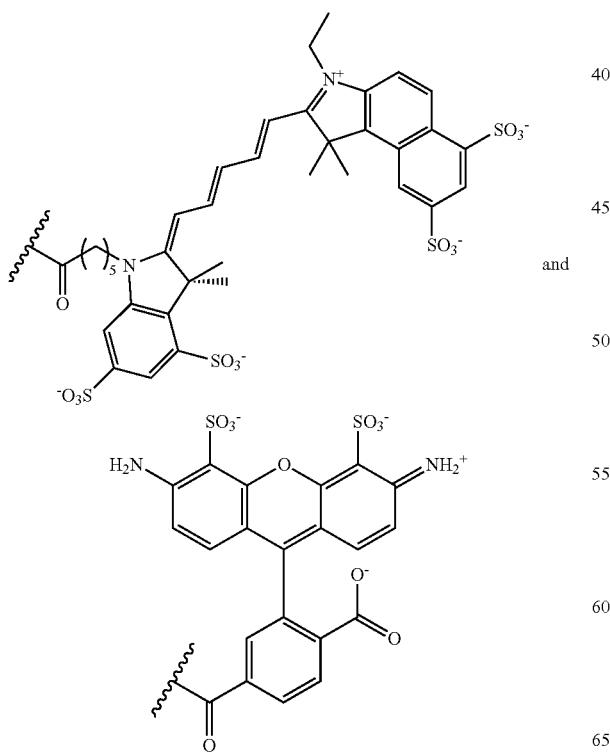

and compounds carrying a fluorine 18 ($^{18}$F) isotope, such as:

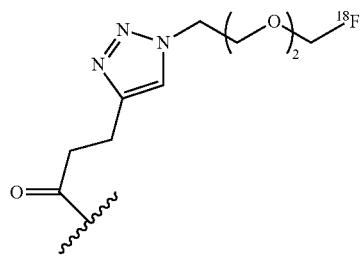

chelating agents carrying a technetium 99 (99 mTc) isotope, it being possible for said chelating agents to optionally comprise from 2 to 6 nitrogen atoms, and preferably 4 nitrogen atoms, and optionally from 1 to 6 carboxylate functions, and preferably 3 carboxylate functions, such as:

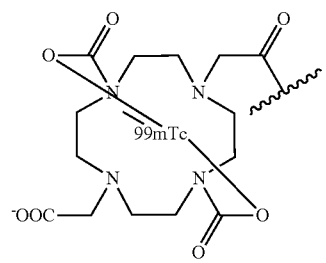

chelating agents carrying a gadolinium Gd(III) atom, it being possible for said chelating agents to optionally comprise from 2 to 6 nitrogen atoms, and preferably 4 nitrogen atoms, and optionally from 1 to 6 carboxylate functions, and preferably 3 carboxylate functions, such as:

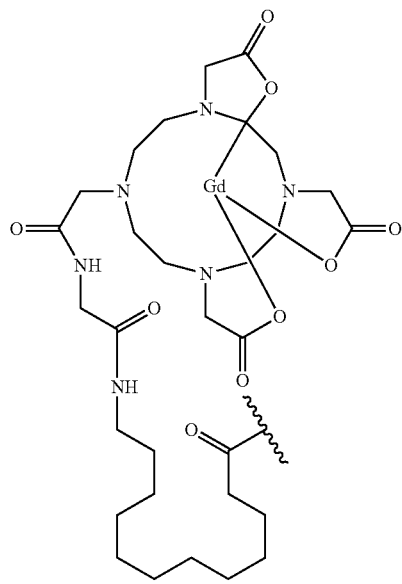

peptide labels such as those defined in international application WO 2010/076654, the content of which is incorporated herein by way of reference, selected from the following sequences:

a) $X_aX_1X_2X_3X_4X_5X_bX_c$ (SEQ ID No.: 1),
in which:

$X_a$, $X_b$ and $X_c$ may be present or absent, $X_a$ or $X_c$, when they are present, comprise at least two natural or unnatural amino acids, $X_b$, when it is present, comprises the peptide sequence RRMQYNRR (SEQ ID NO: 1) in which at least one of the residues is replaced with a natural or unnatural amino acid in which the side chain present in the initial residue that it replaces is absent, $X_1$ consists of any natural or unnatural amino acid comprising an OH group on its side chain, $X_2$ consists of any amino acid with the exception of cysteine, $X_3$ consists of an amino acid chosen from: arginine, glycine and lysine, $X_4$ consists of at least one amino acid chosen from: alanine, glycine, lysine and arginine, $X_5$ consists of any amino acid with the exception of cysteine;

b) the retro-inverso version of a peptide label as defined according to group a).

The nature of the spacer arm L separating the TAG label from the inhibitory part interacting with the MMP active site depends on the initial functionalization of the solid support used. According to one preferred embodiment of the invention, the spacer arm L of the compounds of formula (2) is a $C_1$-$C_2$ alkyl chain or a polyethoxylated chain —($CH_2$—$CH_2$—O)$_n$— in which n is between 1 and 6.

Thus, the compounds of formula (2) can be used as contrast agents for detecting MMPs, and more particularly for detecting MMP-12. The compounds of formula (2) can in particular be used for noninvasive imaging of atheroma plaque (F. A. Jaffer et al., Arterioscler Thromb Vase. Biol. 2009, (10)).

Depending on the nature of the TAG label, various imaging techniques can be envisioned among PET (Positron Emission Tomography), MRI (Magnetic Resonance Imaging) or NIRF (Near-Infrared Fluorescence imaging).

In order to explain the invention more clearly, several embodiments thereof will now be described.

The compounds of the invention were synthesized as described hereinafter.

Materials and Methods:

All the commercially available reagents and solvents were used as received, without additional purification.

The Synphase lanterns (polyamide, lantern series D, Rink amide protected with the Fmoc group, 8 μmol/lantern or polyamide, lantern series D, hydroxymethylphenoxy, 8 μmol/lantern), are sold by Mimotopes (Australia).

The natural amino acids protected with the Fmoc group come from Novabiochem.

The homoglutamate protected with the Fmoc group is sold by Bachem.

The Fmoc-3-aminophenylacetic acid and (S)-Fmoc-(3-carboxymethyl)piperidine are sold by the company NeoMPS.

The 6-chloro-1-hydroxybenzotriazole (ClHOBt) is sold by the company Molekula.

The diisopropylcarbodiimide (DIC), the trifluoroacetic acid (TFA) and the triisopropylsilane (TIS) are sold by the company Aldrich.

The anhydrous N,N-dimethylformamide (DMF) is sold by the company Fluka.

The microwave experiments were performed on an apparatus of Discover type (CEM μWave) in sealed 10 ml reaction tubes or using the open container mode with the SPS kit.

The thin layer chromatography (TLC) plates were aluminum sheets of thin layers coated with a 60F$_{254}$ silica gel, sold by the company Merck.

The precursor malonic blocks were purified by flash chromatography on silica gel Si 60, 40-43 μm.

The $^1$H NMR spectra were recorded on a Bruker instrument at 250 MHz.

The chemical shifts are reported in ppm with the solvent as internal standard (CDCl$_3$: 7.26 ppm; MeOH d$_4$=3.31 ppm; DMSO d$_6$=2.50 ppm).

The data are reported as follows: chemical shift, multiplilcity (s=singlet, d=doublet, t=triplet, q=quartet, br=broad, m multiplet), integration and coupling constants (Hz).

The $^{13}$C NMR spectra were recorded on NMR instruments at 125 MHz with complete proton decoupling.

The chemical shifts are reported in ppm with the solvent as internal standard (CDCl$_3$: 77.16 ppm; MeOH d$_4$=49.00 ppm; DMSO d$_6$=39.52 ppm).

The optical density (OD) measurements were carried out with a Beckman DU640B spectrophotometer.

The electrospray ionization mass spectra (ESMS) were recorded on an ESI-QTRAP mass spectrometry platform (Applied Biosystems-MDS Sciex, University Pierre and Marie Curie (UPMC), Paris, France).

The high resolution mass spectra (HRMS) were recorded using a MALDI-TOF 4800 mass spectrometer (Applied Biosystems, Foster City, USA) in positive reflectron mode in the m/z range of 100-700.

Each spectrum was the result of from 1000 to 2000 shots (20 different positions inside each spot and 50 shots per subspectrum) and an internal calibration was carried out using a 4-HCCA (cyano-4-hydroxycinnamic acid) matrix m/z.

The analytical and preparative RP-HPLC separations were carried out, respectively, on a Thermo separation apparatus and a Gilson apparatus using either an Ascentis Express analytical column (100×4.6 mm, 10μ, 100 Å) or a Kromasil AIT C18 semi-preparative column (250×20 mm, 10μ, 100 Å) with flow rates of 1.8 and 3 mL.min$^{-1}$, respectively.

The detection was carried out at 230 nm.

A solvent system consisting of (A) 0.1% TFA in 90% water-10% acetonitrile, and (B) 0.09% TFA in 90% acetonitrile-10% water, was used. The retention times ($t_R$) obtained in the analytical mode (Ascentis Express column) are reported in minutes.

The amino acid composition of each pseudopeptide was determined under standard conditions: each sample is evaporated under vacuum and hydrolyzed in a sealed tube under 6 N hydrochloric acid vapor in the presence of a phenol crystal, for 17 h at 110° C. using the "PicoTag" system (Waters Associates, Milford, Mass.). The hydrolysate is then dissolved in 100 μl of MilliQ water, and 90 μl of this solution (containing a minimum of 200 μmol of each amino acid) are analyzed and quantified by ninhydrin derivatization on an "aminoTac JLC-500/V amino acids analyzer" apparatus (JEOL, Japan). A standard calibration in the presence of a solution of amino acids of which the concentration is known is carried out before each analysis.

Compounds (3) to (107) were synthesized according to the following general scheme 1:

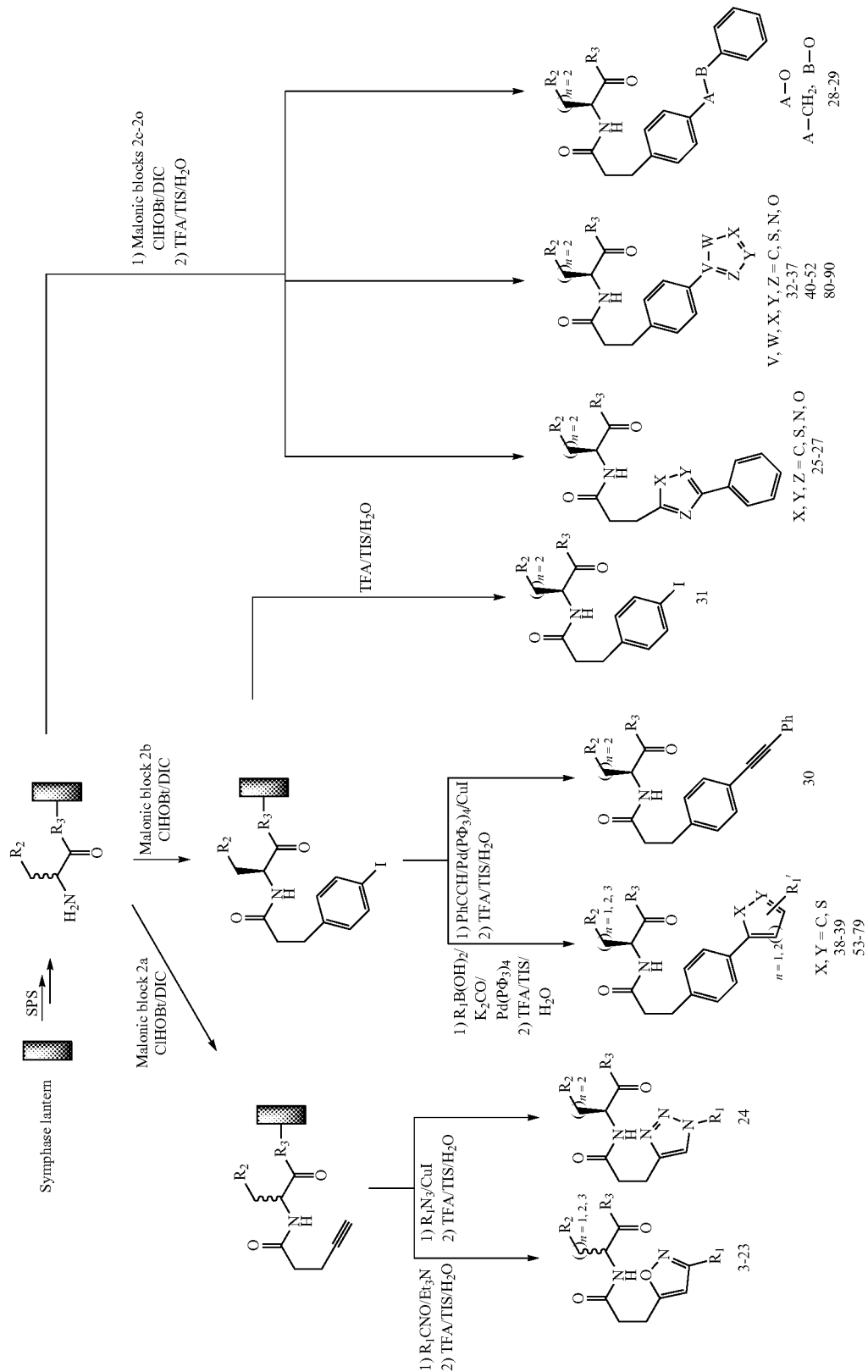

Synthesis of Precursor Malonic Blocks

The precursor malonic blocks are synthesized according to the following scheme 2:

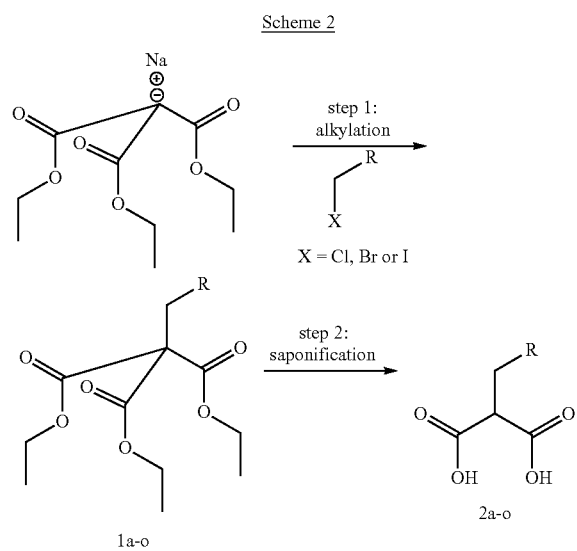

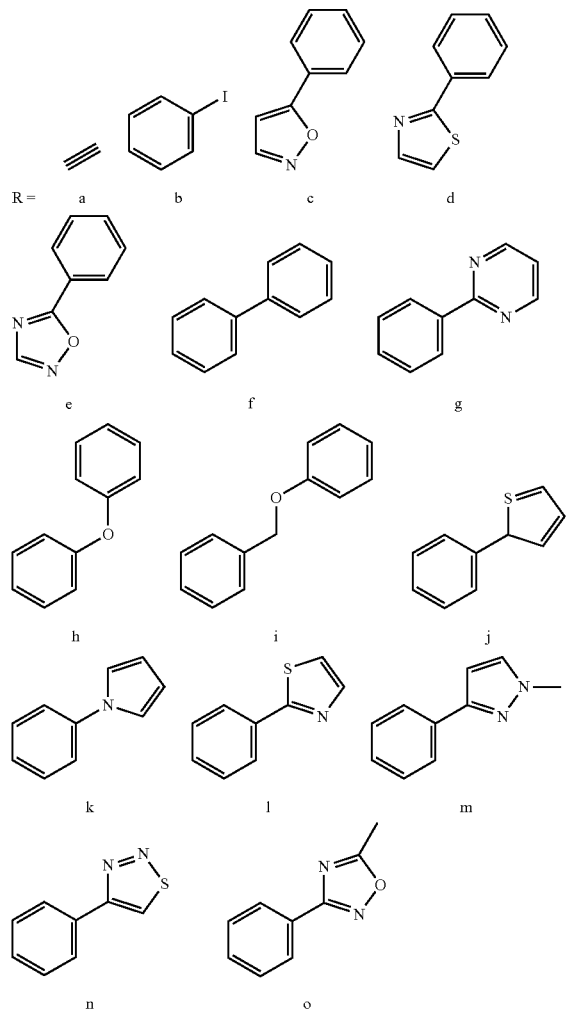

STEP 1

Alkylation Step

In a 10 ml microwave reaction vessel, the sodium derivative of the triethyl ester of methane tricarboxylic acid (3.9 mmol, 1 eq), a derivative of alkyl halide type (4.3 mmol, 1.1 eq) and anhydrous DMF (5 ml) were mixed and stirred at 100° C. under microwave irradiation (300 W) for 5 minutes.

The end of the reaction was verified by thin layer chromatography (TLC) with an eluent mixture (cyclohexane CHX/ethyl acetate EtOAc: 9/1).

The reaction mixture was then evaporated under reduced pressure and the crude solution was suspended in ethyl acetate EtOAc/water $H_2O$ (1/1:10 ml/10 ml).

The aqueous phase was extracted with ethyl acetate EtOAc (2×10 ml). The organic phases were combined and then washed with a saturated solution of sodium chloride NaCl (20 ml) and, finally, dried over anhydrous magnesium sulfate ($MgSO_4$).

The solvent was then concentrated under vacuum and the crude product was purified by flash chromatography (CHX/EtOAc), to give the triesters 1a-o.

Triethyl but-3-yne-1,1,1-tricarboxylate 1a

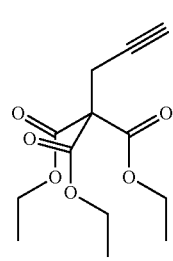

Prepared from propargyl bromide (Fluka 81831, 80% in toluene) according to the general alkylation protocol, to give the title compound in the form of a light yellow oil (yield 88%).

$^1$H NMR (CDCl$_3$): δ 1.29 (t, 9H, J=71-1z); 2.05 (t, 1H, J=2.75 Hz); 3.01 (d, 2H, J=2.751-1z); 4.29 (q, 6H, J=7 Hz).

$^{13}$C NMR (CDCl$_3$): δ 14.00; 23.41; 62.70; 64.68; 70.88; 78.87; 165.90.

Triethyl 2-(4-iodophenyl)ethane-1,1,1-tricarboxylate 1b

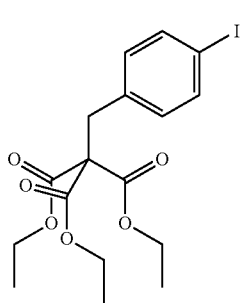

Prepared from 4-iodobenzyl bromide (Aldrich 515604) according to the general alkylation protocol, to give the title compound in the form of a light yellow oil (yield 94%).

¹H NMR (CDCl₃): δ 1.21 (t, 9H, J=6.75 Hz); 3.44 (s, 2H); 4.19 (q, 6H, J=6.75 Hz); 7.05 (d, 2H, J=8 Hz); 7.56 (d, 2H, J=8 Hz).

Triethyl 2-(5-phenylisoxazol-3-yl)ethane-1,1,1-tricarboxylate 1c

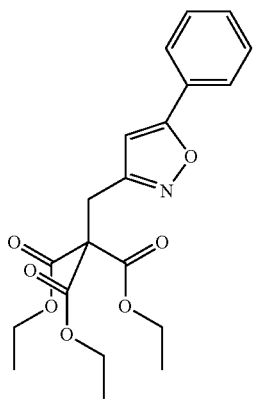

Prepared from 3-chloromethyl-5-phenylisoxazole (Maybridge CC30524) according to the general alkylation protocol, to give the title compound in the form of a light yellow oil (yield 73%).

¹H NMR (CDCl₃): δ 1.27 (t, 9H, J=7.25 Hz); 3.59 (s, 2H); 4.28 (q, 6H, J=7.25 Hz); 6.53 (s, 1H); 7.44 (m, 3H); 7.74 (m, 2H).

Triethyl 2-(2-phenylthiazol-4-yl)ethane-1,1,1-tricarboxylate 1d

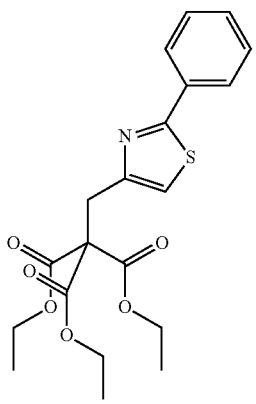

Prepared from 4-(chloromethyl)-2-phenyl-1,3-thiazole (Maybridge CC18324) according to the general alkylation protocol, to give the title compound in the form of a light yellow oil (yield 58%).

¹H NMR (CDCl₃): δ 1.25 (t, 9H, J=7.25 Hz); 3.70 (s, 2H); 4.24 (q, 6H, J=7.25 Hz); 7.11 (s, 1H); 7.43 (m, 3H); 7.9 (m, 2H).

¹³C NMR (CDCl₃): δ 13.95; 14.03; 34.49; 62.31; 62.54; 65.73; 116.16; 126.51; 128.94; 129.91; 133.75; 152.20; 164.07; 166.75; 166.63.

[M+H]⁺=406.1, [M+Na]⁺=428.1.

Triethyl 2-(5-phenyl-1,2,4-oxadiazol-3-yl)ethane-1,1,1-tricarboxylate 1e

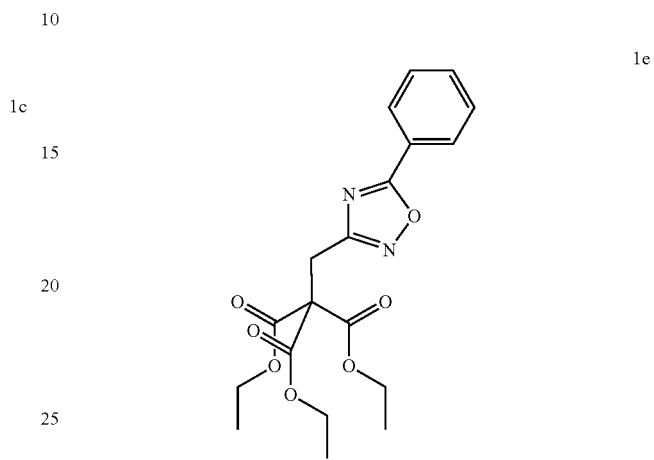

Prepared from 3-chloromethyl-5-phenyl-1,2,4-oxadiazole (Maybridge, SEW02030) according to the general alkylation protocol, to give the title compound in the form of a yellow oil (yield 55%).

¹H NMR (CDCl₃): δ 1.21 (t, 9H, J=7.25 Hz); 3.72 (s, 2H); 4.29 (q, 6H, J=7.25 Hz); 7.5 (m, 3H); 8.02 (d, 2H, J=8 Hz).

¹³C NMR (CDCl₃): δ 13.94; 14.05; 29.59; 62.56; 62.75; 64.35; 124.33; 128.14; 129.13; 132.74; 164.08; 166.06; 167.77; 175.15.

[M+H]⁺=391.3; [M+Na]⁺=413.2.

Triethyl 2-(biphenyl-4-yl)ethane-1,1,1-tricarboxylate 1f

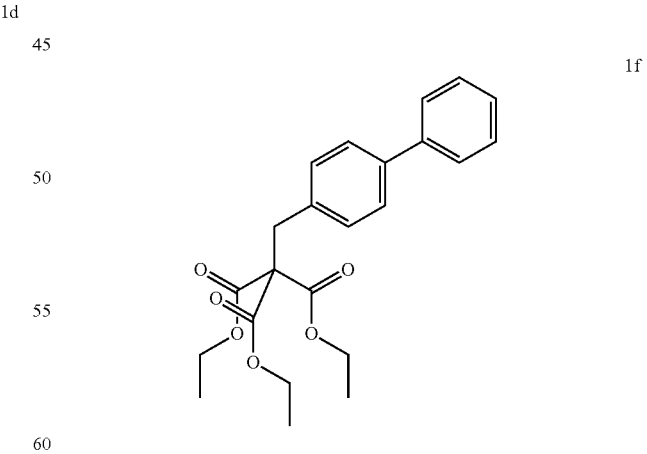

Prepared from 96% 4-(bromomethyl)-4-biphenyl (Acros 368950050) according to the general alkylation protocol, to give the title compound in the form of a pale yellow oil (yield 91%).

¹H NMR (CDCl₃): δ 1.22 (t, 9H, J=7.25 Hz); 3.56 (s, 2H); 4.28 (q, 6H, J=7.25 Hz); 7.29-7.58 (m, 9H).

$^{13}$C NMR (CDCl$_3$): δ 13.99; 27.05; 38.46; 62.32; 66.89; 126.80; 127.15; 127.31; 128.86; 131.10; 134.80; 140.00; 141.00; 166.66.

Triethyl 2-(4-(pyrimidin-2-yl)phenyl)ethane-1,1,1-tricarboxylate 1g

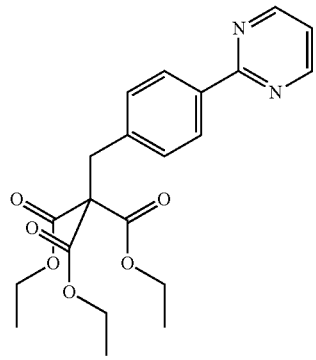

Prepared from 2-[4-(chloromethyl)phenyl]pyrimidine (Maybridge, CC56224) according to the general alkylation protocol, to give the title compound in the form of a pale yellow oil (yield≥95%).

$^1$H NMR (CDCl$_3$): δ 1.21 (t, 9H, J=7.25 Hz); 3.59 (s, 2H); 4.19 (q, 6H, J=7.25 Hz); 7.17 (s, 1H, J=4.75 Hz); 7.40 (d, 2H, J=8.25 Hz); 8.32 (d, 2H, J=8.25 Hz); 8.78 (d, 2H, J=4.75 Hz).

Triethyl 2-(4-phenoxyphenyl)ethane-1,1,1-tricarboxylate 1h

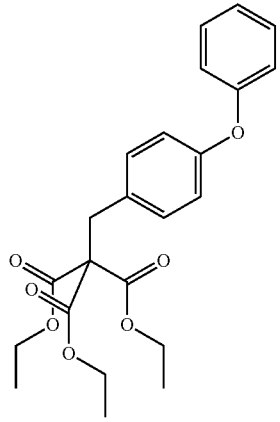

Prepared from 1-(bromomethyl)-4-phenoxybenzene (Maybridge CC53708) according to the general alkylation protocol, to give the title compound in the form of a pale yellow oil (yield=36%).

$^1$H NMR (CDCl$_3$): δ 1.23 (t, 9H, J=7.25 Hz); 3.49 (s, 2H); 4.20 (q, 6H, J=7.25 Hz); 6.88 (d, 2H, J=8.5 Hz); 6.97 (d, 2H, J=8.5 Hz); 7.08 (t, 1H, J=7.25 Hz); 7.29 (m, 4H).

$^{13}$C NMR (CDCl$_3$): δ 13.99; 38.07; 62.27; 66.89; 118.36; 119.01; 123.34; 129.83; 130.40; 132.09; 156.44; 157.25; 166.62.

Triethyl 2-(4-(phenoxymethyl)phenyl)ethane-1,1,1-tricarboxylate 1i

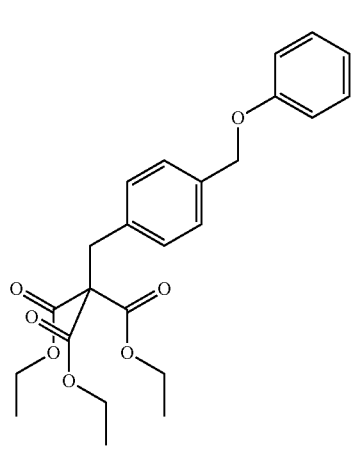

Prepared from 1-(bromomethyl)-4-(phenoxymethyl)benzene (Maybridge CC63708) according to the general alkylation protocol, to give the title compound in the form of a light yellow oil (yield≥95%).

$^1$H NMR (CDCl$_3$): δ 1.21 (t, 9H, J=5.75 Hz); 3.51 (s, 2H); 4.18 (q, 6H, J=5.75 Hz); 5.00 (s, 2H); 6.93 (m, 3H); 7.26 (m, 6H).

Triethyl 2-(4-(thiophen-2-yl)phenyl)ethane-1,1,1-tricarboxylate 1j

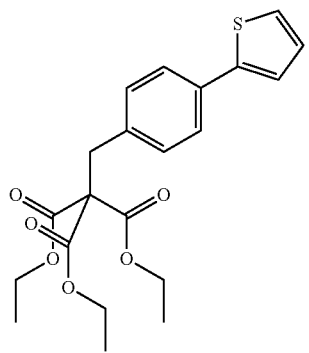

Prepared from 2[4-(bromomethyl)phenyl]thiophene (Maybridge, CC12008) according to the general alkylation protocol, to give the title compound in the form of a yellow oil (yield≥95%).

¹H NMR (CDCl₃): δ 1.22 (t, 9H, J=7 Hz); 3.51 (s, 2H); 4.31 (q. 6H, J=7 Hz); 7.05 (m, 1H); 7.27 (m, 4H); 7.50 (d, 2H, J=8.25 Hz).

Triethyl 2-(4-(1H-pyrrol-1-yl)phenyl)ethane-1,1,1-tricarboxylate 1k

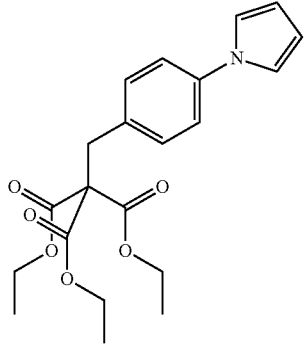

Prepared from 1-[4-(bromomethyl)phenyl]-1H-pyrrole (Maybridge, CC25508) according to the general alkylation protocol, to give the title compound in the form of a yellow oil (yield≥95%).

¹H NMR (CDCl₃): δ 1.21 (t, 9H, J=7.25 Hz); 3.52 (s, 2H); 4.20 (q, 6H, J=7.25 Hz); 6.31 (m, 2H); 7.04 (m, 2H); 7.29 (m, 4H).

Triethyl 2-(4-(thiazol-2-yl)phenyl)ethane-1,1,1-tricarboxylate 1l

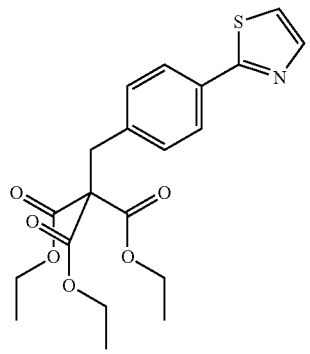

Prepared from 2[4-(chloromethyl)phenyl]-1,3-thiazole (Maybridge, CC40224) according to the general alkylation protocol, to give the title compound in the form of a yellow oil (yield≥95%).

¹H NMR (CDCl₃): δ 1.20 (t, 9H, J=7.25 Hz); 3.54 (s, 2H); 4.19 (q, 6H, J=7.25 Hz); 7.33 (m. 4H); 7.83 (m, 2H).

Triethyl 2-(4-(1-methyl-1H-pyrazol-3-yl)phenyl)ethane-1,1,1-tricarboxylate 1m

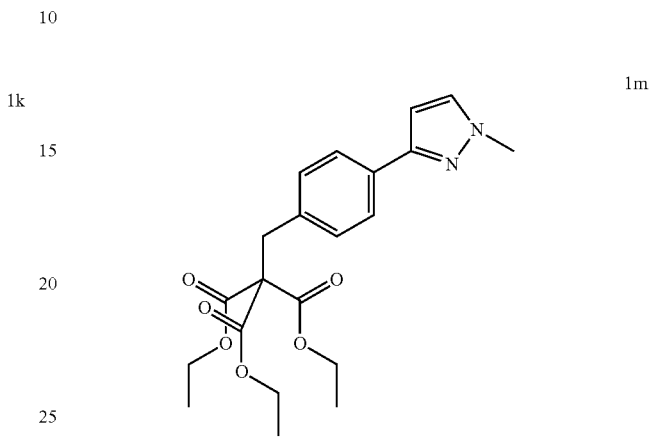

Prepared from 3-[4-(chloromethyl)phenyl]-1-methyl-1H-pyrazole (Maybridge, CC23824) according to the general alkylation protocol, to give the title compound in the form of a yellow oil (yield≥95%).

¹H NMR (CDCl₃): δ 1.20 (t, 9H, J=7.25 Hz); 3.51 (s, 2H); 3.93 (s, 31-1); 4.19 (q, 6H, J=7.25 Hz); 6.49 (d, 1H, J=2.25 Hz); 7.28 (d, 2H, J=8 Hz); 7.65 (d, 2H, J=8 Hz); 7.99 (s, 1H).

Triethyl 2-(4-(1,2,3-thiadiazol-4-yl)phenyl)ethane-1,1,1-tricarboxylate 1n

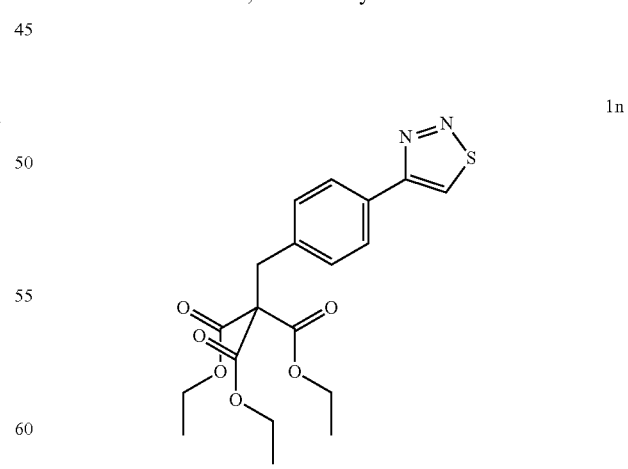

Prepared from 4[4-(bromomethyl)phenyl]-1,2,3-thiadiazole (Maybridge, CC16408) according to the general alkylation protocol, to give the title compound in the form of a yellow oil (yield≥95%).

$^1$H NMR (CDCl$_3$): δ 1.22 (t, 9H, J=7 Hz); 3.58 (s, 2H); 4.21 (q, 6H, J=7 Hz); 7.42 (d, 2H, J=8.25 Hz); 7.92 (d, 2H, J=8.25 Hz); 8.61 (s, 1H).

Triethyl 2-(4-(5-methyl-1,2,4-oxadiazol-3-yl)phenyl)ethane-1,1,1-tricarboxylate 1o

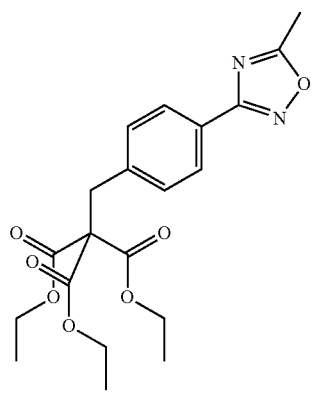

1o

Prepared from 3-[4-(bromomethyl)phenyl]-5-methyl-1,2,4-oxadiazole (Maybridge, CC34808) according to the general alkylation protocol, to give the title compound in the form of a yellow oil (yield≥95%).

$^1$H NMR (CDCl$_3$): δ 1.22 (t, 9H, J=7 Hz); 2.64 (s, 3H); 3.58 (s, 21-I); 4.20 (q, 6H, J=7 Hz); 7.39 (d, 2H, J=8.25 Hz); 7.93 (d, 2H, J=8.25 Hz).

STEP 2

Saponification Step

The triesters 1a-o (3.93 mmol) were solubilized in absolute ethanol (10 ml) and potassium hydroxide (23.58 mmol, 6 eq) was added.

The mixture in solution was stirred at ambient temperature for 1 h and then evaporated under reduced pressure.

The crude product was taken up in 1M hydrochloric acid HCl/EtOAc (1/1:10 ml/10 ml).

The aqueous phase was saturated with NaCl and extracted with EtOAc (2×10 ml).

The organic phases were combined, washed with a saturated NaCl solution (20 ml) and dried over anhydrous MgSO$_4$.

After evaporation, the crude solid was triturated from DCM (1 ml) and then filtered, to give the malonic derivatives 2a-o.

2-(Prop-2-ynyl)malonic acid 2a

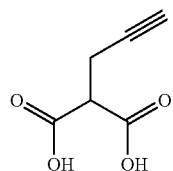

2a

Prepared from the triester 1a according to the saponification protocol, to give the title compound in the form of a white solid (yield 86%).

$^1$H NMR (MeOH d$_4$): δ 2.33 (t, 1H, J=2.75 Hz); 2.69 (dt, 2H, J=2.75 Hz, J=5.25 Hz); 3.51 (t, 1H, J=5.25 Hz).

2-(4-Iodobenzyl)malonic acid 2b

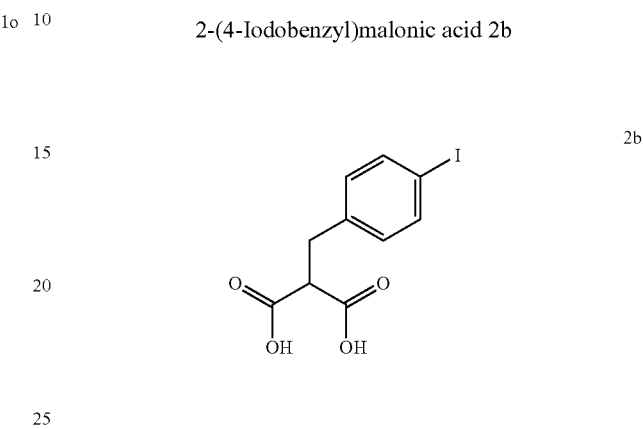

Prepared from the triester 1b according to the saponification protocol, to give the title compound in the form of a white solid (yield 78%).

$^1$H NMR (MeOH d$_4$): δ 3.10 (d, 2H, J=7.75 Hz); 3.61 (t, 1H, J=7.75 Hz), 7.04 (d, 2H, J=8 Hz); 7.61 (d, 2H, J=8 Hz).

$^{13}$C NMR (MeOH d$_4$): δ 35.20; 54.72; 92.45; 132.11; 138.60; 139.58; 172.33.

High resolution mass m/z for C$_{10}$H$_9$INaO$_4$ (M+Na$^+$)$^+$, calculated 342.9443; measured 342.9430.

2-((5-Phenylisoxazol-3-yl)methyl)malonic acid 2c

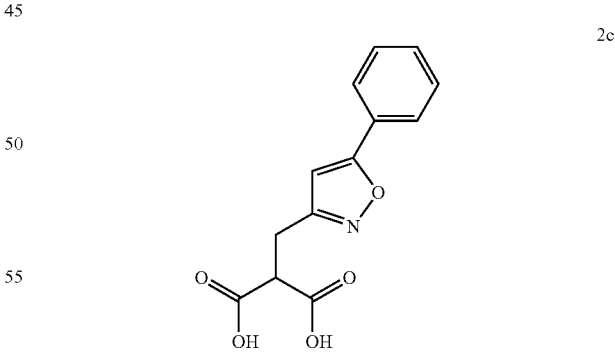

Prepared from the triester 1c according to the saponification protocol, to give the title compound in the form of a white solid (yield 53%).

$^1$H NMR (MeOH d$_4$): 3.26 (d, 2H, J=7.5 Hz); 3.86 (t, 1H, J=7.5 Hz); 6.71 (s, 1H); 7.49 (m, 3H); 7.81 (m, 2H).

$^{13}$C NMR (MeOH d$_4$): δ 26.51; 51.66; 100.83; 126.73; 128.58; 130.19; 131.44; 163.40; 171.28; 171.97.

High resolution mass m/z for $C_{13}H_{12}NO_5$ (M+H$^+$)$^+$, calculated 262.0715; measured 262.0714.

2((2-Phenylthiazol-4-yl)methyl)malonic acid 2d

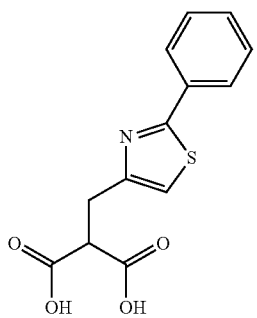

Prepared from the triester 1d according to the saponification protocol, to give the title compound in the form of a white solid (yield 35%).

$^1$H NMR (MeOH d$_4$): δ 3.37 (d, 2H, J=7.75 Hz); 3.93 (t, 1H, J=7.75 Hz); 7.32 (s, 1H); 7.49 (m, 3H); 7.94 (m, 2H).

$^{13}$C NMR (MeOH d$_4$): δ 31.17; 52.76; 116.79; 127.47; 127.62; 130.20; 131.51; 131.66; 134.03; 154.62; 172.25.

High resolution mass m/z for $C_{13}H_{12}NO_4S$ (M+H$^+$)$^+$, calculated 278.0496; measured 278.0488.

2-((5-Phenyl-1,2,4-oxadiazol-3-yl)methyl)malonic acid 2e

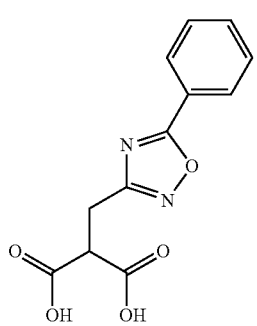

Prepared from the triester 1e according to the saponification protocol, to give the title compound in the form of a white solid (yield 30%).

$^1$H NMR (MeOH d$_4$): δ 3.35 (d, 2H, J=7.5 Hz); 3.99 (t, 1H, J=7.5 Hz); 7.55-7.66 (m, 3H); 8.12 (m, 2H).

$^{13}$C NMR (MeOH d$_4$): δ 26.54; 125.21; 128.99; 129.03; 130.41; 134.19; 170.21; 171.62; 177.05.

High resolution mass m/z for $C_{12}H_{11}N_2O_5$ (M+H$^+$)$^+$, calculated 263.0668; measured 263.0661.

2-(Biphenyl-4-ylmethyl)malonic acid 2f

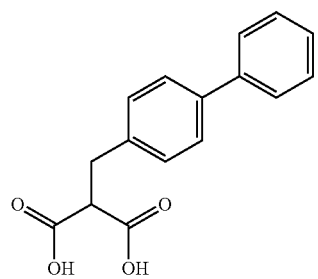

Prepared from the triester 1f according to the saponification protocol, to give the title compound in the form of a white solid (yield 66%).

$^1$H NMR (MeOH d$_4$): δ 3.20 (d, 2H, J=8 Hz); 3.67 (t, 1H, J=8 Hz); 7.30-7.59 (m, 9H).

$^{13}$C NMR (MeOH d$_4$): δ 35.50; 55.02; 127.85; 128.02; 128.20; 129.82; 130.38; 138.87; 140.81; 142.16; 172.50.

High resolution mass m/z for $C_{16}H_{14}NaO_4$ (M+Na$^+$)$^+$, calculated 293.0790; measured 293.0797.

2-(4-(Pyrimidin-2-yl)benzyl)malonic acid 2g

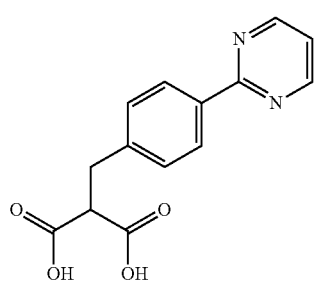

Prepared from the triester 1g according to the saponification protocol, to give the title compound in the form of a white solid (yield 59%).

$^1$H NMR (MeOH d$_4$): δ 3.22 (d, 2H, J=7.75 Hz); 3.69 (t, 1H, J=7.75 Hz); 7.33 (m, 3H); 8.28 (d, 2H, J=8.25 Hz); 8.79 (d, 2H, J=4.75 Hz).

$^{13}$C NMR (MeOH d$_4$): δ 35.60; 54.70; 120.62; 129.30; 130.22; 137.09; 142.97; 158.68; 165.60; 172.40.

High resolution mass m/z for $C_{14}H_{13}N_2O_4$ (M+H$^+$)$^+$, calculated 273.0875; measured 273.0881.

2-(4-Phenoxybenzyl)malonic acid 2h

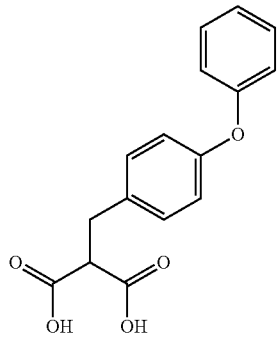

Prepared from the triester 1h according to the saponification protocol, to give the title compound in the form of a white solid (yield 78%).

NMR (MeOH d$_4$): δ 3.14 (d, 2H, J=7.75 Hz); 3.62 (t, 1H, J=7.75 Hz); 6.74 (d, 2H, J=8.5 Hz); 6.95 (d, 2H, J=8 Hz); 7.08 (t, 1H, J=7.25 Hz); 7.23 (d, 2H, J=8.5 Hz); 7.33 (m, 2H).

$^{13}$C NMR (MeOH d$_4$): δ 35.05; 55.01; 119.65; 119.70; 124.23; 130.82; 131.32; 134.37; 134.70; 157.32; 158.80; 172.47.

High resolution mass m/z for $C_{16}H_{14}NaO_5$ (M+Na$^+$)$^+$, calculated 309.0739; measured 309.0726.

2-(4-(Phenoxymethyl)benzyl)malonic acid 2i

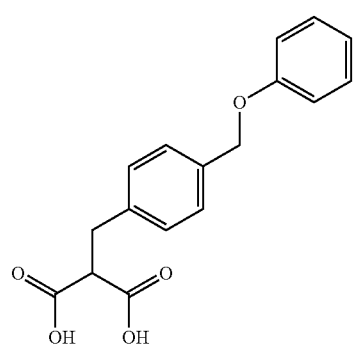

Prepared from the triester 1i according to the saponification protocol, to give the title compound in the form of a white solid (yield 73%).

$^1$H NMR (MeOH d$_4$): δ 3.16 (m, 2H); 3.63 (t, 1H, J=8 Hz); 5.03 (s 3H); 6.93 (m, 3H); 7.20-7.37 (m, 6H).

$^{13}$C NMR (MeOH d4): δ 35.48; 70.60; 115.84; 121.87; 128.77; 129.99; 130.44; 137.06; 139.39; 160.18; 172.51.

High resolution mass m/z for $C_{17}H_{16}NaO_5$ (M+Na$^+$)$^+$, calculated 323.0895; measured 323.0903.

2-(4-(Thiophen-2-yl)benzyl)malonic acid 2j

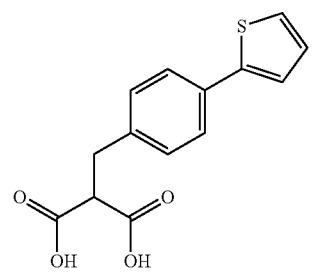

Prepared from the triester 1j according to the saponification protocol, to give the title compound in the form of a white solid (yield 68%).

$^1$H NMR (MeOH d$_4$): δ 3.16 (d, 2H, J=7.75 Hz); 3.65 (t, 1H, J=7.75 Hz); 7.06 (m, 1H); 7.26 (d, 2H, J=8.25 Hz); 7.33 (m, 2H); 7.54 (d, 2H, J=8.25 Hz).

$^{13}$C NMR (MeOH d$_4$): 34.06; 53.47; 122.55; 124.14; 125.34; 127.61; 129.06; 129.09; 132.76; 137.70; 143.80; 170.97.

High resolution mass m/z for $C_{14}H_{13}O_4S$ (M+H$^+$)$^+$, calculated 277.0535; measured 277.0538.

2-(4-(1H-pyrrol-1-yl)benzyl)malonic acid 2k

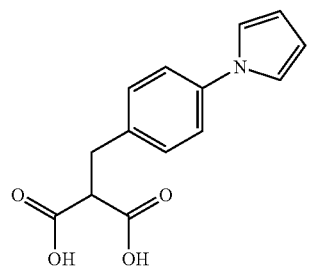

Prepared from the triester 1k according to the saponification protocol, to give the title compound in the form of a white solid (yield 84%).

$^1$H NMR (MeOH d$_4$): δ 3.17 (d, 2H, J=8 Hz); 3.65 (t, 1H, J=8 Hz); 6.25 (m, 2H); 7.14 (m, 2H); 7.35 (m, 4H).

$^{13}$C NMR (MeOH d$_4$): 33.76; 53.56; 109.80; 109.84; 118.51; 119.53; 119.55; 129.70; 129.74; 135.53; 139.32; 170.94.

High resolution mass m/z for $C_{14}H_{14}NO_4$ (M+H$^+$)$^+$, calculated 260.0923; measured 260.0908.

2-(4-(Thiazol-2-yl)benzyl)malonic acid 2l

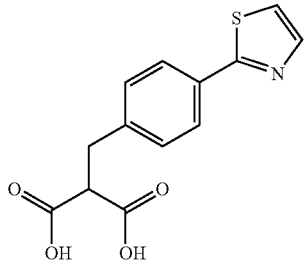

Prepared from the triester 1l according to the saponification protocol, to give the title compound in the form of a white solid (yield 84%).

$^1$H NMR (MeOH d$_4$): δ 3.19 (d, 2H, J=7.5 Hz); 3.68 (t, 1H, J=7.5 Hz); 7.35 (d, 2H, J=8.25 Hz); 7.54 (d, 1H, J=3.25 Hz); 7.82 (m, 3H).

$^{13}$C NMR (MeOH d$_4$): 34.17; 53.25; 119.20; 126.33; 129.35; 131.46; 141.08; 142.81; 168.66; 170.83.

High resolution mass m/z for $C_{13}H_{12}NO_4S$ (M+H$^+$)$^+$, calculated 278.0487; measured 278.0483.

2-(4-(1-Methyl-1H-pyrazol-3-yl)benzyl)malonic acid 2m

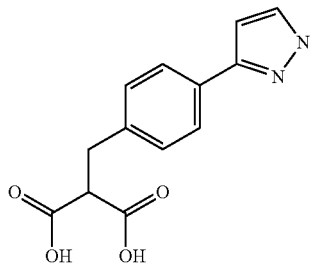

Prepared from the triester 1m according to the saponification protocol, to give the title compound in the form of a white solid (yield 94%).

$^1$H NMR (MeOH d$_4$): δ 3.16 (d, 2H, J=7.75 Hz); 3.64 (t, 1H, J=7.75 Hz); 3.88 (s, 3H); 6.55 (d, 1H, J=2.25 Hz); 7.26 (d, 2H, J=8 Hz); 7.54 (d, 1H, J=2.25 Hz); 7.65 (d, 2H, J=8 Hz).

$^{13}$C NMR (MeOH d$_4$): δ 34.17; 37.37; 53.53; 102.41; 125.26; 128.77; 128.80; 131.51; 132.07; 137.93; 151.37; 171.02.

High resolution mass m/z for $C_{14}H_{15}N_2O_4$ (M+H$^+$)$^+$, calculated 275.1032; measured 275.1020.

2-(4-(1,2,3-Thiadiazol-4-yl)benzyl)malonic acid 2n

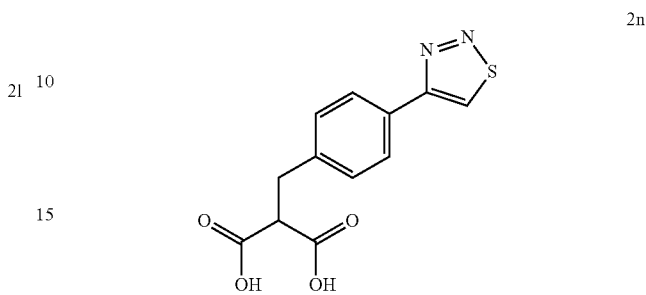

Prepared from the triester 1n according to the saponification protocol, to give the title compound in the form of a white solid (yield 70%).

$^1$H NMR (MeOH d$_4$): δ 3.23 (d, 2H, J=7.75 Hz); 3.71 (t, 1H, J=7.75 Hz); 7.40 (d, 2H, J=8.25 Hz); 7.99 (d, 21-1, J=8.25 Hz); 9.14 (s, 1H).

$^{13}$C NMR (MeOH d$_4$): δ 34.18; 53.39; 126.99; 129.23; 129.33; 131.04; 139.85; 162.43; 170.92.

High resolution mass m/z for $C_{12}H_{11}N_2O_4S$ (M+H$^+$)$^+$, calculated 279.0440; measured 279.0434.

2-(4-(5-Methyl-1,2,4-oxadiazol-3-yl)benzyl)malonic acid 2o

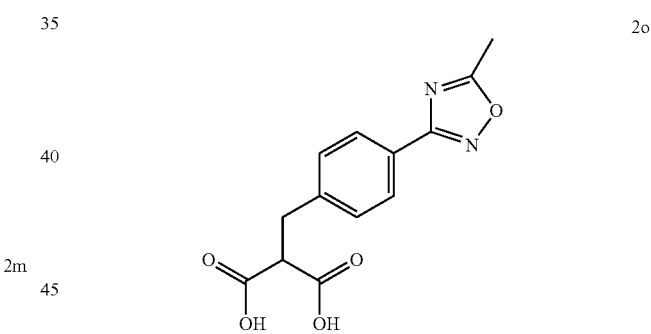

Prepared from the triester 1o according to the saponification protocol, to give the title compound in the form of a white solid (yield 89%).

$^1$H NMR (MeOH d$_4$): δ 2.64 (s, 3H); 3.22 (d, 2H, J=7.75 Hz); 3.69 (t, 1H, J=7.75 Hz); 7.40 (d, 2H, J=8 Hz); 7.94 (d, 2H, J=8.25 Hz).

$^{13}$C NMR (MeOH d$_4$): δ 10.62; 34.26; 53.22; 124.92; 126.90; 129.16; 142.07; 167.82; 170.79; 177.28.

High resolution mass m/z for $C_{13}H_{13}N_2O_5$ (M+H$^+$)$^+$, calculated 277.0824; measured 277.0831.

Synthesis of the pseudopeptides 25-27, 28-29, 31, 32-37, 40-52 and 80-90

Synthesis of the pseudopeptides 25-27, 28-29, 31, 32-37, 40-50 and 80-88, on Synphase lantern having a linker of "Rink amide" type A standard Fmoc strategy was used to construct the peptide sequence. The lanterns are preswollen in DCM for 15 minutes. The Fmoc protective group is deprotected under microwave irradiation (3×3 min, 60° C., 25 W) in the presence of piperidine at 20% in DMF (dimethylformamide). After washing of the lanterns (DMF/2×5 min then DCM/2×5 min) and preactivation of the amino acids at ambient temperature for 5 minutes (10 eq of Fmoc-AA-OH, 10 eq of Cl—HOBt and 10 eq of DIC in anhydrous DMF), the lanterns are immersed in the coupling solution and the reaction is carried out under microwave irradiation (10 min, 60° C., 25 W). This coupling is carried out a second time. This cycle of deprotection of the Fmoc group and incorporation of an amino acid is repeated a second time in order to synthesize the pseudodipeptides. Finally, the precursor malonic blocks (2b-2o) are incorporated in the following way: preactivation of the malonic block in the presence of DIC (5 eq) and of Cl—HOBt (5 eq) in anhydrous DMF for 5 minutes at ambient temperature, then immersion of the lanterns in the coupling solution. The reaction is then carried out under microwave irradiation (10 min, 60° C., 25 W). Finally, the lanterns are washed (DMF/2×5 min then DCM/2×5 min).

Synthesis of the pseudopeptides 51-52 and 89-90 on Synphase lantern incorporating a linker of "hydroxymethylphenoxy" type The Fmoc-3-aminophenylacetic (10 eq) or (S)-Fmoc-(3-carboxymethyl)piperidine (10 eq) unnatural amino acids are preactivated in the presence of DIC (5 eq) in a solution of anhydrous DCM/anhydrous DMF (9/1) for 10 minutes at ambient temperature. The lanterns, swollen in parallel in DCM, are then immersed in the coupling solution. DMAP (0.5 eq) is added and the reaction mixture is gently stirred for one hour at ambient temperature. The lanterns are then washed (DMF/2×5 min then DCM/2×5 min) and the natural amino acids and also the precursor malonic blocks are incorporated as described above.

1,3-dipolar cycloaddition reaction and access to the pseudopeptides 3-23 and 24

After construction of the peptide sequence and incorporation of the malonic block 2a as described previously, a 1,3-dipolar cycloaddition reaction is carried out on a solid support.

Access to the pseudopeptides 3-23:

The isoxazole unit is generated according to the method developed in the laboratory and described by Makaritis A. et al (Makaritis A. et al 2003 Chem. Eur. J. (9)). The precursor oxime (10 eq) is dissolved in anhydrous DCM and two drops of pyridine are added. NCS (10 eq) is then added at ambient temperature and, after stirring for 10 min, the reaction mixture is heated for one hour at 45° C. After cooling, the lanterns are immersed in the reaction mixture and triethylamine is added (20 eq). After gentle stirring for 12 hours at ambient temperature, this operation is then repeated with a freshly prepared reaction mixture. Finally, the lanterns are washed (DMF/2×5 min and DCM/2×5 min).

Access to the pseudopeptide 24:

The lanterns are immersed in a reaction mixture containing phenyl azide (10 eq), a solution of copper(I) iodide in THF (2 eq theoretical from a solution of which the concentration is estimated at 0.18 M) and triethylamine (50 eq). The cycloaddition reaction is then carried out under microwave irradiation in a sealed tube (80° C., 10 min, 300 W). Finally, the lanterns are washed (DMF/2×5 min and DCM/2×5 min).

Suzuki reaction or Sonogashira reaction on a solid support, access to the pseudopeptides 38-39, 53-79, 91-107 and 30

After construction of the peptide sequence and incorporation of the malonic block 2b as previously described, a coupling reaction with palladium on a solid support is carried out as follows.

Suzuki Reaction:

The lanterns are immersed in a reaction mixture containing a precursor of boronic acid or pinacolic ester type (10 eq, 0.2 M in pre-degassed DMF), potassium carbonate (10 eq, 0.16 M in MilliQ water) and Pd(PPh$_3$)$_4$ (1 eq, 0.08 M in pre-degassed DMF). The coupling reaction is then carried out under microwave irradiation in a sealed tube (80° C., 5 min, 300 W). Finally, the lanterns are washed (DMF/2×5 min and DCM/2×5 min).

Sonogashira Reaction:

The lanterns are immersed in a reaction mixture containing phenylacetylene (10 eq, 0.2 M in pre-degassed DMF), Pd(PPh$_3$)$_4$ (1 eq, 0.08 M in pre-degassed DMF) and copper iodide (1 eq) in a solution of DMF/DIEA (1/1). The coupling reaction is then carried out under microwave irradiation in a sealed tube (80° C., 30 min, 300 W). Finally, the lanterns are washed (DMF/2×5 min and DCM/2×5 min).

Cleavage from the Solid Support, Purification, Characterization, Packaging and Storage of the Pseudopeptides Each pseudopeptide synthesized as described above is then cleaved from its support as follows. The lantern is immersed in a cleavage solution (TFA/TIS/H$_2$O: 95/2.5/2.5). After stirring for 1 hour at ambient temperature, the lantern is transferred into a new cleavage solution (TFA/DCM: 1/1) and stirred for thirty minutes at ambient temperature. The two cleavage solutions are then combined, and evaporated under reduced pressure, and the reaction crude is taken up in a solution A/B:1/1 with A: 0.1% of TFA in 90% of MilliQ water/10% of acetonitrile and B: 0.09% of TFA in 90% of acetonitrile/10% of MilliQ water. Each pseudopeptide is then purified by reverse-phase HPLC on a Kromasil AIT C18 semi-preparative column (250×20 mm, flow rate= 3 ml.min$^{-1}$, UV detection at 230 nm) using a linear gradient as follows: from 0 to 40 min: from 0 to 100% of B, with A: 0.1% of TFA in 90% of MilliQ water/10% of acetonitrile, and B: 0.09% of TFA in 90% of acetonitrile/10% of MilliQ water. After freeze-drying, each pseudopeptide is taken up in a solution of absolute ethanol/MilliQ water: 1/1. The solution is neutralized (pH=7-8) with a 1M NaHCO$_3$ solution. The concentration of each solution is determined by analysis of the amino acid composition. All the solutions containing the pseudopeptides are stored in a refrigerator at +4° C. The analytical data for each pseudopeptide are summarized in table III hereinafter.

TABLE III

| | Formula | Name | Analytical data |
|---|---|---|---|
| 3 | | (S)-5-amino-4-((S)-4-carboxy-2-(3-(3-(3'-chlorobiphenyl-4-yl)isoxazol-5-yl)propanamido)butanamido)-5-oxopentanoic acid | Ascentis Express: $t_R$ = 5.40 min $\epsilon_{272}$ = 31915 $M^{-1} \cdot cm^{-1}$ $^1$H NMR (DMSO d$_6$): δ 1.75 (m, 2H); 1.89 (m, 2H); 2.23 (m, 4H); 2.62 (m, 2H); 3.03 (m, 2H); 4.21 (m, 2H); 6.86 (s, 1H); 7.11 (s, 1H); 7.32 (s, 1H); 7.51 (m, 2H); 7.72 (d, 1H, J = 7.25 Hz); 7.84 (m, 3H); 7.94 (d, 2H, J = 8.25 Hz); 8.00 (d, 1H, J = 7.75 Hz); 8.28 (d, 1H, J = 7.25 Hz); High resolution mass m/z for $C_{28}H_{30}ClN_4O_8$ (M + H$^+$)$^+$: calculated 585.1752; measured 585.1733. |
| 4 | | (S)-5-amino-4-(3-(3-(3'-chlorobiphenyl-4-yl)isoxazol-5-yl)propanamido)-5-oxopentanoic acid | Ascentis Express: $t_R$ = 5.69 min $\epsilon_{272}$ = 18230 $M^{-1} \cdot cm^{-1}$ High resolution mass m/z for $C_{23}H_{23}ClN_3O_5$ (M + H$^+$)$^+$: calculated 456.1326; measured 456.1330. |
| 5 | | (R)-5-amino-4-((S)-4-carboxy-2-(3-(3-(3'-chlorobiphenyl-4-yl)isoxazol-5-yl)propanamido)butanamido)-5-oxopentanoic acid | Ascentis Express: $t_R$ = 5.46 min $\epsilon_{272}$ = 29100 $M^{-1} \cdot cm^{-1}$ High resolution mass m/z for $C_{28}H_{30}ClN_4O_8$ (M + H$^+$)$^+$: calculated 585.1752; measured 585.1746. |

TABLE III-continued

| | Formula | Name | Analytical data |
|---|---|---|---|
| 6 | 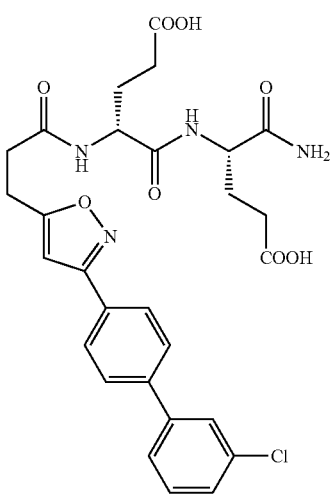 | (S)-5-amino-4-((R)-4-carboxy-2-(3-(3-(3'-chlorobiphenyl-4-yl)isoxazol-5-yl)propanamido)butanamido)-5-oxopentanoic acid | Ascentis Express: $t_R$ = 5.47 min $\epsilon_{272}$ = 29240 $M^{-1} \cdot cm^{-1}$ High resolution mass m/z for $C_{28}H_{30}ClN_4O_8$ $(M + H^+)^+$: calculated 585.1752; measured 585.1746. |
| 7 | 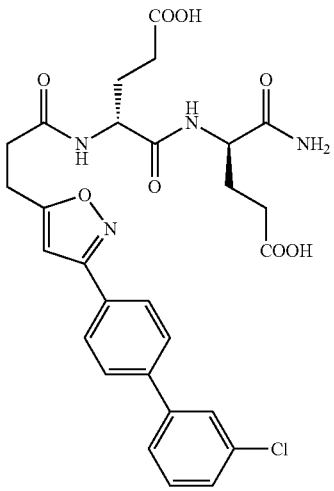 | (R)-5-amino-4-((R)-4-carboxy-2-(3-(3-(3'-chlorobiphenyl-4-yl)isoxazol-5-yl)propanamido)butanamido)-5-oxopentanoic acid | Ascentis Express: $t_R$ = 5.49 min $\epsilon_{272}$ = 29834 $M^{-1} \cdot cm^{-1}$ High resolution mass m/z for $C_{28}H_{30}ClN_4O_8$ $(M + H^+)^+$: calculated 585.1752; measured 585.1741. |
| 8 | 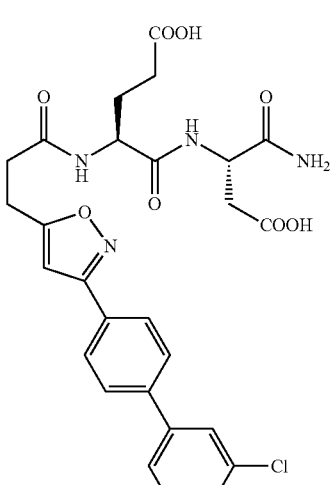 | (S)-5-((S)-1-amino-3-carboxy-1-oxopropan-2-ylamino)-4-(3-(3-(3'-chlorobiphenyl-4-yl)isoxazol-5-yl)propanamido)-5-oxopentanoic acid | Ascentis Express: $t_R$ = 5.47 min $\epsilon_{272}$ = 32941 $M^{-1} \cdot cm^{-1}$ High resolution mass m/z for $C_{27}H_{28}ClN_4O_8$ $(M + H^+)^+$: calculated 571.195; measured 571.1594. |

TABLE III-continued

| | Formula | Name | Analytical data |
|---|---|---|---|
| 9 | | (S)-5-amino-4-((S)-3-carboxy-2-(3-(3-(3'-chlorobiphenyl-4-yl)isoxazol-5-yl)propanamido)propanamido)-5-oxopentanoic acid | Ascentis Express: $t_R$ = 5.49 min $\epsilon_{272}$ = 30769 M$^{-1}$·cm$^{-1}$ High resolution mass m/z for $C_{27}H_{28}ClN_4O_8$ (M + H$^+$)$^+$: calculated 571.1595; measured 571.1598. |
| 10 | | (S)-4-amino-3-((S)-3-carboxy-2-(3-(3-(3'-chlorobiphenyl-4-yl)isoxazol-5-yl)propanamido)propanamido)-4-oxobutanoic acid | Ascentis Express: $t_R$ = 5.51 min $\epsilon_{272}$ = 31507 M$^{-1}$·cm$^{-1}$ High resolution mass m/z for $C_{26}H_{26}ClN_4O_8$ (M + H$^+$)$^+$: calculated 557.1438; measured 557.1453. |
| 11 | | (S)-6-((S)-1-amino-4-carboxy-1-oxobutan-2-ylamino)-5-(3-(3-(3'-chlorobiphenyl-4-yl)isoxazol-5-yl)propanamido)-6-oxohexanoic acid | Ascentis Express: $t_R$ = 5.53 min $\epsilon_{272}$ = 30827 M$^{-1}$·cm$^{-1}$ High resolution mass m/z for $C_{29}H_{32}ClN_4O_{88}$ (M + H$^+$)$^+$: calculated 599.1909; measured 599.1897. |

TABLE III-continued

| | Formula | Name | Analytical data |
|---|---|---|---|
| 12 | | (S)-6-amino-5-((S)-4-carboxy-2-(3-(3-(3'-chlorobiphenyl-4-yl)isoxazol-5-yl)propanamido)butanamido)-6-oxohexanoic acid | Ascentis Express:<br>$t_R$ = 5.51 min<br>$\epsilon_{272}$ = 31655 M$^{-1}$·cm$^{-1}$<br>High resolution mass m/z for $C_{29}H_{32}ClN_4O_{88}$ (M + H$^+$)$^+$: calculated 599.1909; measured 599.1905. |
| 13 | | (S)-6-amino-5-((S)-5-carboxy-2-(3-(3-(3'-chlorobiphenyl-4-yl)isoxazol-5-yl)propanamido)pentanamido)-6-oxohexanoïque | Ascentis Express:<br>$t_R$ = 5.57 min<br>$\epsilon_{272}$ = 31915 M$^{-1}$·cm$^{-1}$<br>High resolution mass m/z for $C_{30}H_{34}ClN_4O_8$ (M + H$^+$)$^+$: calculated 613.2065; measured 613.2077. |
| 14 | | (S)-5-amino-4-((S)-4-carboxy-2-(3-(3-phenylisoxazol-5-yl)propanamido)butanamido)-5-oxopentanoic acid | Ascentis Express:<br>$t_R$ = 2.89 min<br>$\epsilon_{241}$ = 11950 M$^{-1}$·cm$^{-1}$<br>High resolution mass m/z for $C_{22}H_{27}N_4O_{88}$ (M + H$^+$)$^+$ calculated 475.1828; measured 475.1823. |

TABLE III-continued

| Formula | Name | Analytical data |
|---|---|---|
| 15 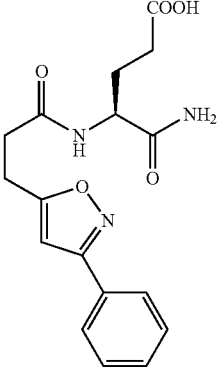 | (S)-5-amino-5-oxo-4-(3-(3-phenylisoxazol-5-yl)propanamido)pentanoic acid | Ascentis Express: $t_R$ = 3.26 min $\epsilon_{241}$ = 5996 $M^{-1} \cdot cm^{-1}$ High resolution mass m/z for $C_{17}H_{20}N_3O_5$ $(M + H^+)^+$: calculated 346.1403; measured 346.1395. |
| 16 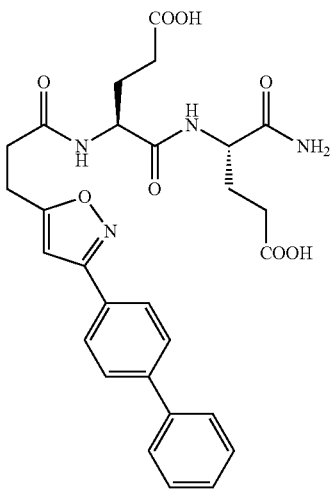 | (S)-5-amino-4-((S)-2-(3-(3-(biphenyl-4-yl)isoxazol-5-yl)propanamido)-4-carboxybutanamido)-5-oxopentanoic acid | Ascentis Express: $t_R$ = 4.82 min $\epsilon_{273}$ = 35600 $M^{-1} \cdot cm^{-1}$ High resolution mass m/z for $C_{28}H_{31}N_4O_8$ $(M + H^+)^+$: calculated 551.2142; measured 551.2135. |
| 17 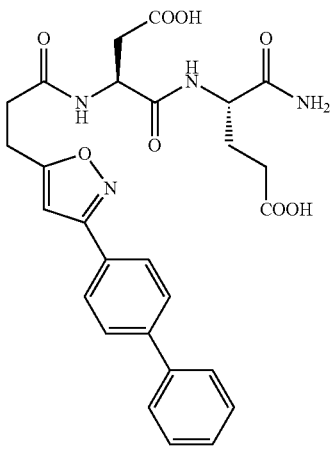 | (S)-5-amino-4-((S)-2-(3-(3-(biphenyl-4-yl)isoxazl-5-yl)propanamido)-3-carboxypropanamido)-5-oxopentanoic acid | Ascentis Express: $t_R$ = 4.84 min $\epsilon_{273}$ = 28375 $M^{-1} \cdot cm^{-1}$ High resolution mass m/z for $C_{27}H_{29}N_4O_8$ $(M + H^+)^+$: calculated 537.1985; measured 537.1996. |

TABLE III-continued

| | Formula | Name | Analytical data |
|---|---|---|---|
| 18 | 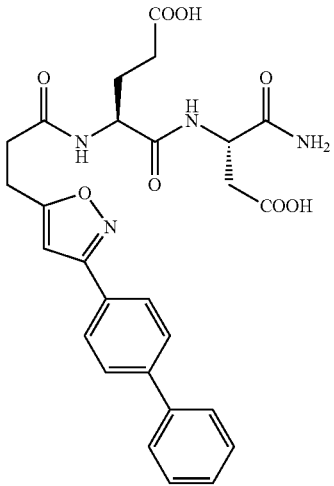 | (S)-5-((S)-1-amino-3-carboxy-1-oxopropan-2-ylamino)-4-(3-(3-(biphenyl-4-yl)isoxazol-5-yl)propanamido)-5-oxopentanoic acid | Ascentis Express:<br>$t_R$ = 4.85 min<br>$\epsilon_{273}$ = 25370 $M^{-1} \cdot cm^{-1}$<br>High resolution mass m/z<br>for $C_{27}H_{29}N_4O_8$<br>$(M + H^+)^+$: calculated<br>537.1985; measured<br>537.1995. |
| 19 | 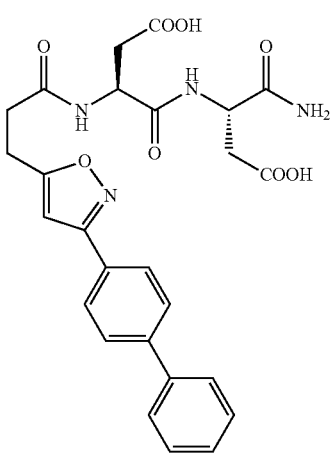 | (S)-4-amino-3-((S)-2-(3-(3-(biphenyl-4-yl)isoxazol-5-yl)propanamido)-3-carboxypropanamido)-4-oxobutanoic acid | Ascentis Express:<br>$t_R$ = 4.85 min<br>$\epsilon_{273}$ = 28120 $M^{-1} \cdot cm^{-1}$<br>High resolution mass m/z<br>for $C_{26}H_{27}N_4O_8$<br>$(M + H^+)^+$: calculated<br>523.1828; measured<br>523.1810. |
| 20 | 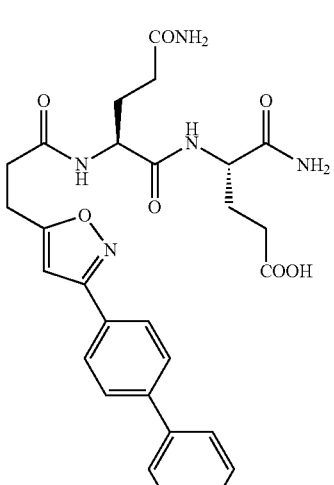 | (S)-5-amino-4-((S)-5-amino-2-(3-(3-(biphenyl-4-yl)isoxazol-5-yl)propanamido)-5-oxopentanamido)-5-oxopentanoic acid | Ascentis Express:<br>$t_R$ = 4.75 min<br>$\epsilon_{273}$ = 35825 $M^{-1} \cdot cm^{-1}$<br>High resolution mass m/z<br>for $C_{28}H_{32}N_5O_7$<br>$(M + H^+)^+$: calculated<br>550.2302, measured<br>550.2319. |

TABLE III-continued

| | Formula | Name | Analytical data |
|---|---|---|---|
| 21 | 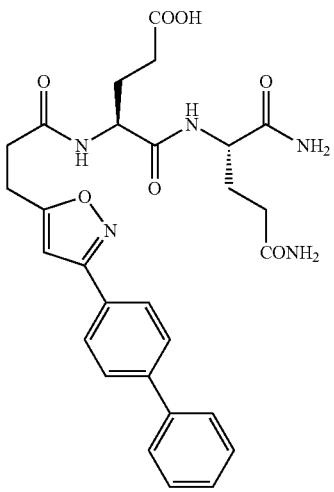 | (S)-4-(3-(3-(biphenyl-4-yl)isoxazol-5-yl)propanamido)-5-((S)-1,5-diamino-1,5-dioxopentan-2-ylamino)-5-oxopentanoic acid | Ascentis Express:<br>$t_R$ = 4.77 min<br>$\epsilon_{273}$ = 34482 $M^{-1} \cdot cm^{-1}$<br>High resolution mass m/z for $C_{28}H_{32}N_5O_7$<br>$(M + H^+)^+$: calculated 550.2302; measured 550.2299. |
| 22 | 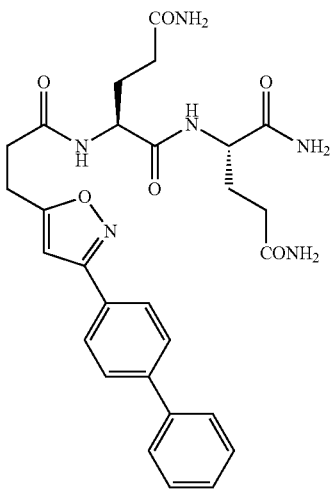 | (S)-2-(3-(3-(biphenyl-4-yl)isoxazol-5-yl)propanamido)-$N^1$-((S)-1,5-diamino-1,5-dioxopentan-2-yl)pentanediamide | Ascentis Express:<br>$t_R$ = 4.39 min<br>$\epsilon_{273}$ = 23214 $M^{-1} \cdot cm^{-1}$<br>High resolution mass m/z for $C_{28}H_{33}N_6O_6$<br>$(M + H^+)^+$: calculated 549.2462; measured 549.2454. |
| 23 | 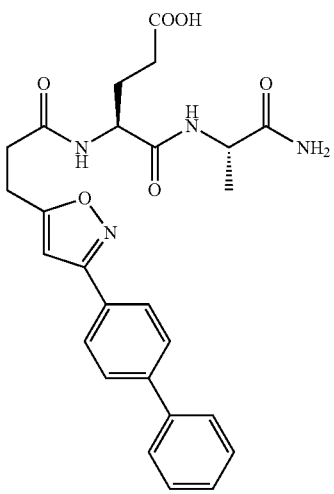 | (S)-5-((S)-1-amino-1-oxopropan-2-ylamino)-4-(3-(3-(biphenyl-4-yl)isoxazol-5-yl)propanamido)-5-oxopentanoic acid | Ascentis Express:<br>$t_R$ = 5.00 min<br>$\epsilon_{273}$ = 34078 $M^{-1} \cdot cm^{-1}$<br>High resolution mass m/z for $C_{26}H_{29}N_4O_6$<br>$(M + H^+)^+$: calculated 493.2087; measured 493.2093. |

TABLE III-continued

| | Formula | Name | Analytical data |
|---|---|---|---|
| 24 | | (S)-5-amino-4-((S)-4-carboxy-2-(3-(1-phenyl-1H-1,2,3-triazol-4-yl)propanamido)butanamido)-5-oxopentanoic acid | Ascentis Express:<br>$t_R$ = 2.23 min<br>$\epsilon_{248}$ = 4827 $M^{-1} \cdot cm^{-1}$<br>High resolution mass m/z for $C_{21}H_{27}N_6O_7$<br>$(M + H^+)^+$: calculated 475.1941; measured 475.1953. |
| 25 | | (S)-5-amino-4-((S)-4-carboxy-2-(3-(5-phenylisoxazol-3-yl)propanamido)butanamido)-5-oxopentanoic acid | Ascentis Express:<br>$t_R$ = 3.27 min<br>$\epsilon_{263}$ = 23750 $M^{-1} \cdot cm^{-1}$<br>High resolution mass m/z for $C_{22}H_{27}N_4O_8$<br>$(M + H^+)^+$: calculated 475.1829; measured 475.1843. |
| 26 | | (S)-5-amino-4-((S)-4-carboxy-2-(3-(5-phenyl-1,2,4-oxadiazol-3-yl)propanamido)butanamido)-5-oxopentanoic acid | Ascentis Express:<br>$t_R$ = 3.32 min<br>$\epsilon_{253}$ = 17391 $M^{-1} \cdot cm^{-1}$<br>High resolution mass m/z for $C_{21}H_{26}N_5O_8$<br>$(M + H^+)^+$: calculated 476.1782; measured 476.1794. |
| 27 | | (S)-5-amino-4-((S)-4-carboxy-2-(3-(2-phenylthiazol-4-yl)propanamido)butanamido)-5-oxopentanoic acid | Ascentis Express:<br>$t_R$ = 3.32 min<br>$\epsilon_{294}$ = 13992 $M^{-1} \cdot cm^{-1}$<br>High resolution mass m/z for $C_{22}H_{27}N_4O_7S$<br>$(M + H^+)^+$: calculated 491.1601; measured 491.1613. |

TABLE III-continued

| | Formula | Name | Analytical data |
|---|---|---|---|
| 28 | | (S)-5-amino-4-((S)-4-carboxy-2-(3-(4-phenoxyphenyl)propanamido)butanamido)-5-oxopentanoic acid | Ascentis Express:<br>$t_R$ = 4.73 min<br>$\epsilon_{272}$ = 1593 $M^{-1} \cdot cm^{-1}$<br>High resolution mass m/z for $C_{25}H_{30}N_3O_8$<br>$(M + H^+)^+$: calculated 500.2033; measured 500.2024. |
| 29 | | (S)-5-amino-4-((S)-4-carboxy-2-(3-(4-(phenoxymethyl)phenyl)propanamido)butanamido)-5-oxopentanoic acid | Ascentis Express:<br>$t_R$ = 3.87 min<br>$\epsilon_{274}$ = 3584 $M^{-1} \cdot cm^{-1}$<br>High resolution mass m/z for $C_{26}H_{31}N_3NaO_8$<br>$(M + Na^+)^+$: calculated 536.2009; measured 536.2000. |
| 30 | | (S)-5-amino-4-((S)-4-carboxy-2-(3-(4-(phenylethynyl)phenyl)propanamido)butanamido)-5-oxopentanoic acid | Ascentis Express:<br>$t_R$ = 4.93 min<br>$\epsilon_{284}$ = 42452 $M^{-1} \cdot cm^{-1}$<br>$\epsilon_{302}$ = 37736 $M^{-1} \cdot cm^{-1}$<br>High resolution mass m/z for $C_{27}H_{30}N_3O_7$<br>$(M + H^+)^+$: calculated 508.2084; measured 508.2076. |
| 31 | | (S)-5-amino-4-((S)-4-carboxy-2-(3-(4-iodophenyl)propanamido)butanamido)-5-oxopentanoic acid | Ascentis Express:<br>$t_R$ = 3.69 min<br>$\epsilon_{259}$ = 370 $M^{-1} \cdot cm^{-1}$<br>High resolution mass m/z for $C_{19}H_{25}IN_3O_7$<br>$(M + H^+)^+$: calculated 534.0737; measured 534.0734. |

TABLE III-continued

| | Formula | Name | Analytical data |
|---|---|---|---|
| 32 | | (S)-5-amino-4-((S)-4-carboxy-2-(3-(4-(pyrimidin-2-yl)phenyl)propanamido)butanamido)-5-oxopentanoic acid | Ascentis Express:<br>$t_R$ = 2.40 min<br>$\epsilon_{266}$ = 20275 M$^{-1}$·cm$^{-1}$<br>High resolution mass m/z for $C_{23}H_{28}N_5O_7$<br>$(M + H^+)^+$: calculated 486.1989; measured 486.1982. |
| 33 | | (S)-5-amino-4-((S)-4-carboxy-2-(3-(4-(1-methyl-1H-pyrazol-3-yl)phenyl)propanamido)butanamido)-5-oxopentanoic acid | Ascentis Express:<br>$t_R$ 2.60 min<br>$\epsilon_{257}$ = 24934 M$^{-1}$·cm$^{-1}$<br>High resolution mass m/z for $C_{23}H_{30}N_5O_7$<br>$(M + H^+)^+$: calculated 488.2145; measured 488.2143. |
| 34 | | (S)-5-amino-4-((S)-4-carboxy-2-(3-(4-(5-methyl-1,2,4-oxadiazol-3-yl)phenyl)propanamido)butanamido)-5-oxopentanoic acid | Ascentis Express:<br>$t_R$ = 2.77 min<br>$\epsilon_{246}$ = 15544 M$^{-1}$·cm$^{-1}$<br>High resolution mass m/z for $C_{22}H_{28}N_5O_8$<br>$(M + H^+)^+$: calculated 490.1938; measured 490.1922. |
| 35 | | (S)-4-(3-(4-(1,2,3-thiadiazol-4-yl)phenyl)propanamido)-5-((S)-1-amino-4-carboxy-1-oxobutan-2-ylamino)-5-oxopentanoic acid | Ascentis Express:<br>$t_R$ = 3.27 min<br>$\epsilon_{245}$ = 10729 M$^{-1}$·cm$^{-1}$<br>High resolution mass m/z for $C_{21}H_{26}N_5O_7S$<br>$(M + H^+)^+$: calculated 492.1553; measured 492.1551. |

TABLE III-continued

| | Formula | Name | Analytical data |
|---|---|---|---|
| 36 | | (S)-4-(3-(4-(1H-pyrrol-1-yl)phenyl)propanamido)-5-((S)-1-amino-4-carboxy-1-oxobutan-2-ylamino)-5-oxopentanoic acid | Ascentis Express: $t_R$ = 3.69 min $\epsilon_{253}$ = 14677 $M^{-1} \cdot cm^{-1}$ High resolution mass m/z for $C_{23}H_{28}N_4NaO_7$ $(M + Na^+)^+$: calculated 495.1856; measured 495.1860. |
| 37 | | (S)-5-amino-4-((S)-4-carboxy-2-(3-(4-(thiazol-2-yl)phenyl)propanamido)butanamido)-5-oxopentanoic acid | Ascentis Express: $t_R$ = 2.69 min $\epsilon_{288}$ = 27972 $M^{-1} \cdot cm^{-1}$ High resolution mass m/z for $C_{22}H_{27}N_4O_7S$ $(M + H^+)^+$: calculated 491.1601; measured 491.1585. |
| 38 | | (S)-5-amino-4-((S)-4-carboxy-2-(3-(4-(thiophen-3-yl)phenyl)propanamido)butanamido)-5-oxopentanoic acid | Ascentis Express: $t_R$ = 3.97 min $\epsilon_{262}$ = 14495 $M^{-1} \cdot cm^{-1}$ High resolution mass m/z for $C_{23}H_{28}N_3O_7S$ $(M + H^+)^+$: calculated 490.1648; measured 490.1636. |
| 39 | | (S)-5-amino-4-((S)-2-(3-(4-(benzo[d]thiazol-2-yl)phenyl)propanamido)-4-carboxybutanamido)-5-oxopentanoic acid | Ascentis Express: $t_R$ = 5.15 min $\epsilon_{277}$ = 28729 $M^{-1} \cdot cm^{-1}$ ESI m/z $(M + H^+)^+$ = 540.1 |

TABLE III-continued

| | Formula | Name | Analytical data |
|---|---|---|---|
| 40 | | (S)-5-amino-4-((S)-2-(3-(biphenyl-4-yl)propanamido)-4-carboxybutanamido)-5-oxopentanoic acid | Ascentis Express: $t_R$ = 4.26 min; $\varepsilon_{253}$ = 22540 $M^{-1} \cdot cm^{-1}$; $^1$H NMR (DMSO $d_6$): δ 1.71 (m, 2H); 1.87 (m, 2H); 2.22 (m, 4H); 2.51 (m, 2H); 2.85 (m, 2H); 4.21 (m, 2H); 7.12 (s, 1H); 7.33 (m, 4H); 7.45 (t, 2H, J = 7.25 Hz) 7.56 (d, 2H, J = 7.25 Hz); 7.63 (d, 2H, J = 7.25 Hz) 7.96 (d, 1H, J = 7.75 Hz); 8.13 (d, 1H, J = 7.5 Hz). High resolution mass m/z for $C_{25}H_{30}N_3O_7$ $(M + H^+)^+$: calculated 484.2084; measured 483.2084. |
| 42 | | (S)-4-(3-(biphenyl-4-yl)propanamido)-5-((S)-1,5-diamino-1,5-dioxopentan-2-ylamino)-5-oxopentanoic acid | Ascentis Express: $t_R$ = 4.10 min; $\varepsilon_{253}$ = 25357 $M^{-1} \cdot cm^{-1}$; High resolution mass m/z for $C_{25}H_{31}N_4O_6$ $(M + H^+)^+$: calculated 483.2244; measured 483.2246. |
| 43 | | (S)-2-(3-(biphenyl-4-yl)propanamido)-$N^1$-((S)-1,5-diamino-1,5-dioxopentan-2-yl)pentanediamide | Ascentis Express: $t_R$ = 3.83 min; $\varepsilon_{253}$ = 45205 $M^{-1} \cdot cm^{-1}$; High resolution mass m/z for $C_{25}H_{32}N_5O_5$ $(M + H^+)^+$: calculated 482.2403; measured 482.2397. |
| 44 | | (S)-4-(3-(biphenyl-4-yl)propanamido)-5-((S)-1,6-diamino-1-oxohexan-2-ylamino)-5-oxopentanoic acid | Ascentis Express: $t_R$ = 3.69 min; $\varepsilon_{253}$ = 22540 $M^{-1} \cdot cm^{-1}$; High resolution mass m/z for $C_{26}H_{35}N_4O_5$ $(M + H^+)^+$: calculated 483.2607; measured 483.2598 |

TABLE III-continued

| | Formula | Name | Analytical data |
|---|---|---|---|
| 45 | | (S)-5-((S)-1-amino-3-carboxy-1-oxopropan-2-ylamino)-4-(3-(biphenyl-4-yl)propanamido)-5-oxopentanoic acid | Ascentis Express:<br>$t_R$ = 4.07 min<br>$\epsilon_{253}$ = 22540 $M^{-1} \cdot cm^{-1}$<br>High resolution mass m/z<br>for $C_{24}H_{28}N_3O_7$<br>$(M + H^+)^+$: calculated<br>470.1927; measured<br>470.1928 |
| 46 | | (S)-5-((S)-1-amino-3-(4-hydroxyphenyl)-1-oxopropan-2-ylamino)-4-(3-(biphenyl-4-yl)propanamido)-5-oxopentanoic acid | Ascentis Express:<br>$t_R$ 4.58 min<br>$\epsilon_{253}$ = 22540 $M^{-1} \cdot cm^{-1}$<br>High resolution mass m/z<br>for $C_{29}H_{32}N_3O_6$<br>$(M + H^+)^+$: calculated<br>518.2281; measured<br>518.2281 |
| 47 | | (S)-5-((S)-1-amino-1-oxopropan-2-ylamino)-4-(3-(biphenyl-4-yl)propanamido)-5-oxopentanoic acid | Ascentis Express:<br>$t_R$ = 4.39 min<br>$\epsilon_{253}$ = 22540 $M^{-1} \cdot cm^{-1}$<br>High resolution mass m/z<br>for $C_{23}H_{28}N_3O_5$<br>$(M + H^+)^+$: calculated<br>426.2028; measured<br>426.2025 |
| 48 | | (S)-5-((S)-1-amino-3-(1H-imidazol-4-yl)-1-oxopropan-2-ylamino)-4-(3-(biphenyl-4-yl)propanamido)-5-oxopentanoic acid | Ascentis Express:<br>$t_R$ = 3.64 min<br>$\epsilon_{253}$ = 22540 $M^{-1} \cdot cm^{-1}$<br>High resolution mass m/z<br>for $C_{26}H_{30}N_5O_5$<br>$(M + H^+)^+$: calculated<br>492.2247; measured<br>492.2259 |

TABLE III-continued

| | Formula | Name | Analytical data |
|---|---|---|---|
| 49 | | (S)-5-((S)-1-amino-3-hydroxy-1-oxopropan-2-ylamino)-4-(3-(biphenyl-4-yl)propanamido)-5-oxopentanoic acid | Ascentis Express:<br>$t_R$ = 4.02 min<br>$\epsilon_{253}$ = 22540 M$^{-1}$ · cm$^{-1}$<br>High resolution mass m/z for $C_{23}H_{28}N_3O_6$<br>$(M + H^+)^+$: calculated 442.1978; measured 442.1975 |
| 50 | | (S)-5-((S)-1-amino-4-methyl-1-oxopentan-2-ylamino)-4-(3-(biphenyl-4-yl)propanamido)-5-oxopentanoic acid | Ascentis Express:<br>$t_R$ = 5.75 min<br>$\epsilon_{253}$ = 22540 M$^{-1}$ · cm$^{-1}$<br>High resolution mass m/z for $C_{26}H_{34}N_3O_5$<br>$(M + H^+)^+$: calculated 468.2498; measured 468.2491 |
| 51 | | (S)-4-(3-(biphenyl-4-yl)propanamido)-5-((S)-3-(carboxymethyl)piperidin-1-yl)-5-oxopentanoic acid | Ascentis Express:<br>$t_R$ = 5.16 min<br>$\epsilon_{253}$ = 35271 M$^{-1}$ · cm$^{-1}$<br>High resolution mass m/z for $C_{27}H_{33}N_2O_6$<br>$(M + H^+)^+$: calculated 481.2339; measured 481.2338 |
| 52 | | (S)-4-(3-(biphenyl-4-yl)propanamido)-5-(3-(carboxymethyl)phenylamino)-5-oxopentanoic acid | Ascentis Express:<br>$t_R$ = 5.51 min<br>$\epsilon_{250}$ = 18309 M$^{-1}$ · cm$^{-1}$<br>High resolution mass m/z for $C_{28}H_{28}N_2NaO_6$<br>$(M + Na^+)^+$: calculated 511.1845; measured 511.1855 |

TABLE III-continued

| | Formula | Name | Analytical data |
|---|---|---|---|
| 53 | | (S)-5-amino-4-((S)-2-(3-(3'-aminobiphenyl-4-yl)propanamido)-4-carboxybutanamido)-5-oxopentanoic acid | Ascentis Express:<br>$t_R$ = 1.93 min<br>$\epsilon_{260}$ = 9580 $M^{-1} \cdot cm^{-1}$<br>High resolution mass m/z for $C_{25}H_{30}N_4NaO_7$<br>$(M + Na^+)^+$: calculated 521.2012; measured 521.2019 |
| 54 | | (S)-5-amino-4-((S)-4-carboxy-2-(3-(3'-hydroxybiphenyl-4-yl)propanamido)butanamido)-5-oxopentanoic acid | Ascentis Express:<br>$t_R$ = 3.24 min<br>$\epsilon_{254}$ = 13970 $M^{-1} \cdot cm^{-1}$<br>High resolution mass m/z for $C_{25}H_{30}N_3O_8$<br>$(M + H^+)^+$: calculated 500.2033; measured 500.2031 |
| 55 | | (S)-5-amino-4-((S)-4-carboxy-2-(3-(3'-nitrobiphenyl-4-yl)propanamido)butanamido)-5-oxopentanoic acid | Ascentis Express:<br>$t_R$ = 4.20 min<br>$\epsilon_{254}$ = 20158 $M^{-1} \cdot cm^{-1}$<br>High resolution mass m/z for $C_{25}H_{29}N_4O_9$<br>$(M + H^+)^+$: calculated 529.1935; measured 529.1954 |
| 56 | | 4'-(3-((S)-1-((S)-1-amino-4-carboxy-1-oxobutan-2-ylamino)-4-carboxy-1-oxobutan-2-ylamino)-3-oxopropyl)biphenyl-3-carboxylic acid | Ascentis Express:<br>$t_R$ = 3.29 min<br>$\epsilon_{257}$ = 6082 $M^{-1} \cdot cm^{-1}$<br>High resolution mass m/z for $C_{26}H_{30}N_3O_9$<br>$(M + H^+)^+$: calculated 528.1982; measured 528.1991 |

TABLE III-continued

| | Formula | Name | Analytical data |
|---|---|---|---|
| 57 | | (S)-5-amino-4-((S)-4-carboxy-2-(3-(3'-chlorobiphenyl-4-yl)propanamido)butanamido)-5-oxopentanoic acid | Ascentis Express: $t_R$ = 4.84 min; $\epsilon_{260}$ = 18195 M$^{-1}$·cm$^{-1}$; High resolution mass m/z for $C_{25}H_{29}ClN_3O_7$ (M + Na$^+$)$^+$: calculated 540.1513; measured 540.1482 |
| 58 | | (S)-5-amino-4-((S)-4-carboxy-2-(3-(3',5'-dichlorobiphenyl-4-yl)propanamido)butanamido)-5-oxopentanoic acid | Ascentis Express: $t_R$ = 5.48 min; $\epsilon_{260}$ = 21808 M$^{-1}$·cm$^{-1}$; High resolution mass m/z for $C_{25}H_{28}Cl_2N_3O_7$ (M + H$^+$)$^+$: calculated 552.1304; measured 552.1320 |
| 59 | | (S)-5-amino-4-((S)-4-carboxy-2-(3-(3'-methoxybiphenyl-4-yl)propanamido)butanamido)-5-oxopentanoic acid | Ascentis Express: $t_R$ 4.37 min; $\epsilon_{254}$ = 12000 M$^{-1}$·cm$^{-1}$; High resolution mass m/z for $C_{26}H_{32}N_3O_8$ (M + H$^+$)$^+$: calculated 514.2189; measured 514.2177 |
| 60 | | (S)-5-amino-4-((S)-4-carboxy-2-(3-(3'-(hydroxymethyl)biphenyl-4-yl)propanamido)butanamido)-5-oxopentanoic acid | Ascentis Express: $t_R$ = 3.21 min; $\epsilon_{254}$ = 21560 M$^{-1}$·cm$^{-1}$; High resolution mass m/z for $C_{26}H_{32}N_3O_8$ (M + H$^+$)$^+$: calculated 514.2189; measured 514.2164 |

TABLE III-continued

| | Formula | Name | Analytical data |
|---|---|---|---|
| 61 | | (S)-5-amino-4-((S)-4-carboxy-2-(3-(4'-phenylbiphenyl-4-yl)propanamido)butanamido)-5-oxopentanoic acid | Ascentis Express: $t_R$ = 5.70 min $\epsilon_{280}$ = 44827 $M^{-1} \cdot cm^{-1}$ $^1$H NMR (DMSO d$_6$): δ 1.74 (m, 2H); 1.90 (m, 2H); 2.21 (m, 4H); 2.51 (m, 2H); 2.83 (m, 2H); 4.19 (m, 2H); 7.11 (s, 1H); 7.31 (m, 3H); 7.38 (d, 1H, J = 7.25 Hz); 7.48 (t, 2H, J = 7.25 Hz); 7.64 (d, 2H, J = 8 Hz); 7.72 (m, 6H); 7.95 (d, 1H, J = 7.75 Hz); 8.14 (d, 1H, J = 7.5 Hz). High resolution mass m/z for C$_{31}$H$_{33}$N$_3$NaO$_7$ (M + Na$^+$)$^+$: calculated 582.2216; measured 582.2210 |
| 62 | | (S)-5-((S)-1,5-diamino-1,5-dioxopentan-2-ylamino)-4-(3-(4'-phenylbiphenyl-4-yl)propanamido)-5-oxopentanoic acid | Ascentis Express: $t_R$ = 5.40 min $\epsilon_{280}$ = 44827 $M^{-1} \cdot cm^{-1}$ High resolution mass m/z for C$_{31}$H$_{34}$N$_4$NaO$_6$ (M + Na$^+$)$^+$: calculated 581.2376; measured 581.2388 |
| 63 | | (S)-5-((S)-1,6-diamino-1-oxohexan-2-ylamino)-4-(3-(4'-phenylbiphenyl-4-yl)propanamido)-5-oxopentanoic acid | Ascentis Express: $t_R$ = 5.17 min $\epsilon_{254}$ = 44827 $M^{-1} \cdot cm^{-1}$ High resolution mass m/z for C$_{32}$H$_{39}$N$_4$O$_5$ (M + H$^+$)$^+$: calculated 559.2920; measured 559.5921 |

TABLE III-continued

| | Formula | Name | Analytical data |
|---|---|---|---|
| 64 | | (S)-5-((S)-1-amino-3-carboxy-1-oxopropan-2-ylamino)-4-(3-(4'-phenylbiphenyl-4-yl)propanamido)-5-oxopentanoic acid | Ascentis Express:<br>$t_R$ = 5.72 min<br>$\epsilon_{280}$ = 44827 $M^{-1} \cdot cm^{-1}$<br>High resolution mass m/z<br>for $C_{30}H_{31}N_3NaO_7$<br>$(M + Na^+)^+$: calculated 568.2060; measured 568.2058 |
| 65 | | (S)-5-((S)-1-amino-3-(4-hydroxyphenyl)-1-oxopropan-2-ylamino)-4-(3-(4'-phenylbiphenyl-4-yl)propanamido)-5-oxopentanoic acid | Ascentis Express:<br>$t_R$ = 6.07 min<br>$\epsilon_{280}$ = 44827 $M^{-1} \cdot cm^{-1}$<br>High resolution mass m/z<br>for $C_{35}H_{35}N_3NaO_6$<br>$(M + Na^+)^+$: calculated 616.2423; measured 616.2426 |
| 66 | | (S)-5-((S)-1-amino-1-oxopropan-2-ylamino)-4-(3-(4'-phenylbiphenyl-4-yl)propanamido)-5-oxopentanoic acid | Ascentis Express:<br>$t_R$ = 5.99 min<br>$\epsilon_{280}$ = 44827 $M^{-1} \cdot cm^{-1}$<br>High resolution mass m/z<br>for $C_{29}H_{31}N_3NaO_5$<br>$(M + Na^+)^+$: calculated 524.2161; measured 524.2156 |
| 67 | | (S)-5-((S)-1-amino-3-(1H-imidazol-4-yl)-1-oxopropan-2-ylamino)-4-(3-(4'-phenylbiphenyl-4-yl)propanamido)-5-oxopentanoic acid | Ascentis Express:<br>$t_R$ = 5.21 min<br>$\epsilon_{254}$ = 44827 $M^{-1} \cdot cm^{-1}$<br>High resolution mass m/z<br>for $C_{32}H_{34}N_5O_5$<br>$(M + H^+)^+$: calculated 568.2560; measured 568.2579 |

TABLE III-continued

| | Formula | Name | Analytical data |
|---|---|---|---|
| 68 | 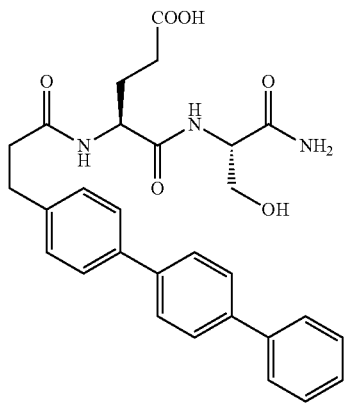 | (S)-5-((S)-1-amino-3-hydroxy-1-oxopropan-2-ylamino)-4-(3-(4'-phenylbiphenyl-4-yl)propanamido)-5-oxopentanoic acid | Ascentis Express:<br>$t_R$ = 5.61 min<br>$\epsilon_{280}$ = 44827 $M^{-1} \cdot cm^{-1}$<br>High resolution mass m/z for $C_{29}H_{31}N_3NaO_6$ $(M + Na^+)^+$: calculated 540.2111; measured 540.2100 |
| 69 | 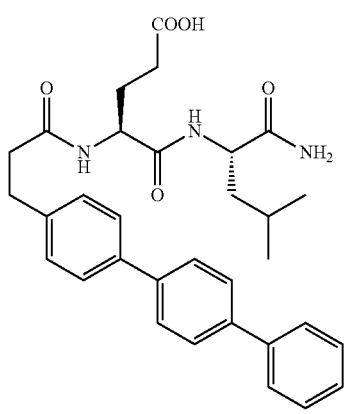 | (S)-5-((S)-1-amino-4-methyl-1-oxopentan-2-ylamino)-4-(3-(4'-phenylbiphenyl-4-yl)propanamido)-5-oxopentanoic acid | Ascentis Express:<br>$t_R$ = 6.69 min<br>$\epsilon_{280}$ = 44827 $M^{-1} \cdot cm^{-1}$<br>High resolution mass m/z for $C_{32}H_{37}N_3NaO_5$ $(M + Na^+)^+$: calculated 566.2631; measured 566.2610 |
| 70 | 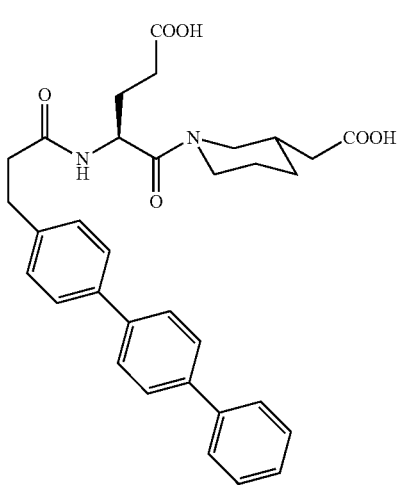 | (S)-5-((S)-3-(carboxymethyl)piperidin-1-yl)-4-(3-(4'-phenylbiphenyl-4-yl)propanamido)-5-oxopentanoic acid | Ascentis Express:<br>$t_R$ = 6.63 min<br>$\epsilon_{280}$ = 56364 $M^{-1} \cdot cm^{-1}$<br>High resolution mass m/z for $C_{33}H_{36}N_2NaO_6$ $(M + Na^+)^+$: calculated 579.2471; measured 579.2453 |

TABLE III-continued

| | Formula | Name | Analytical data |
|---|---|---|---|
| 71 | | (S)-5-(3-(carboxymethyl)phenylamino)-4-(3-(4'-phenylbiphenyl-4-yl)propanamido)-5-oxopentanoic acid | Ascentis Express:<br>$t_R$ = 6.85 min<br>$\epsilon_{280}$ = 53398 M$^{-1}$·cm$^{-1}$<br>High resolution mass m/z for $C_{33}H_{36}N_2NaO_6$ (M + Na$^+$)$^+$: calculated 587.2158; measured 587.2138 |
| 72 | | (S)-5-amino-4-((S)-5-amino-2-(3-(4'-phenylbiphenyl-4-yl)propanamido)-5-oxopentanamido)-5-oxopentanoic acid | Ascentis Express:<br>$t_R$ = 5.51 min<br>$\epsilon_{280}$ = 44827 M$^{-1}$·cm$^{-1}$<br>High resolution mass m/z for $C_{31}H_{34}N_4NaO_6$ (M + Na$^+$)$^+$: calculated 581.2376; measured 581.2386 |
| 73 | | (S)-5-amino-4-((S)-6-amino-2-(3-(4'-phenylbiphenyl-4-yl)propanamido)hexanamido)-5-oxopentanoic acid | Ascentis Express:<br>$t_R$ = 5.14 min<br>$\epsilon_{254}$ = 44827 M$^{-1}$·cm$^{-1}$<br>High resolution mass m/z for $C_{32}H_{39}N_4O_5$ (M + H$^+$)$^+$: calculated 559.2920; measured 559.2944 |

TABLE III-continued

| | Formula | Name | Analytical data |
|---|---|---|---|
| 74 | | (S)-5-amino-4-((S)-3-carboxy-2-(3-(4'-phenylbiphenyl-4-yl)propanamido)propanamido)-5-oxopentanoic acid | Ascentis Express: $t_R$ = 5.73 min $\epsilon_{280}$ = 44827 $M^{-1} \cdot cm^{-1}$ High resolution mass m/z for $C_{30}H_{31}N_3NaO_7$ $(M + Na^+)^+$: calculated 568.2060; measured 568.2068 |
| 75 | | (S)-5-amino-4-((S)-3-(4-hydroxyphenyl)-2-(3-(4'-phenylbiphenyl-4-yl)propanamido)propanamido)-5-oxopentanoic acid | Ascentis Express: $t_R$ = 6.17 min $\epsilon_{280}$ = 44827 $M^{-1} \cdot cm^{-1}$ High resolution mass m/z for $C_{35}H_{35}N_3NaO_6$ $(M + Na^+)^+$: calculated 616.2423; measured 616.2435 |
| 76 | | (S)-5-amino-4-((S)-2-(3-(4'-phenylbiphenyl-4-yl)propanamido)propanamido)-5-oxopentanoic acid | Ascentis Express: $t_R$ = 5.96 min $\epsilon_{280}$ = 44827 $M^{-1} \cdot cm^{-1}$ High resolution mass m/z for $C_{29}H_{31}N_3NaO_5$ $(M + Na^+)^+$: calculated 524.2161; measured 524.2178 |
| 77 | | (S)-4-((S)-3-(1H-imidazol-4-yl)-2-(3-(4'-phenylbiphenyl-4-yl)propanamido)propanamido)-5-amino-5-oxopentanoic acid | Ascentis Express: $t_R$ = 5.25 min $\epsilon_{254}$ = 44827 $M^{-1} \cdot cm^{-1}$ High resolution mass m/z for $C_{32}H_{34}N_5O_5$ $(M + H^+)^+$: calculated 568.2560; measured 568.2554 |

TABLE III-continued

| | Formula | Name | Analytical data |
|---|---|---|---|
| 78 | | (S)-5-amino-4-((S)-3-hydroxy-2-(3-(4'-phenylbiphenyl-4-yl)propanamido)propanamido)-5-oxopentanoic acid | Ascentis Express: $t_R$ = 5.81 min $\epsilon_{280}$ = 44827 $M^{-1} \cdot cm^{-1}$ High resolution mass m/z for $C_{29}H_{31}N_3NaO_6$ $(M + Na^+)^+$: calculated 540.2111; measured 540.2080 |
| 79 | | (S)-5-amino-4-((S)-4-methyl-2-(3-(4'-phenylbiphenyl-4-yl)propanamido)pentanamido)-5-oxopentanoic acid | Ascentis Express: $t_R$ = 6.74 min $\epsilon_{280}$ 44827 $M^{-1} \cdot cm^{-1}$ High resolution mass m/z for $C_{32}H_{37}N_3NaO_5$ $(M + Na^+)^+$: calculated 566.2631; measured 566.2617 |
| 80 | | (S)-5-amino-4-((S)-4-carboxy-2-(3-(4-(thiophen-2-yl)phenyl)propanamido)butanamido)-5-oxopentanoic acid | Ascentis Express: $t_R$ = 4.10 min $\epsilon_{285}$ = 22000 $M^{-1} \cdot cm^{-1}$ $^1$H NMR (DMSO $d_6$): δ 1.75 (m, 2H); 1.91 (m, 2H); 2.22 (m 4H); 2.51 (m, 2H); 2.82 (m, 2H); 4.20 (m, 2H); 7.11 (m, 2H); 7.25 (d, 2H, J = 8 Hz); 7.32 (s, 1H); 7.46 (d, 1H, J = 3.5 Hz); 7.51 (d, 1H, J = 5.25 Hz); 7.56 (d, 2H, J = 8 Hz); 7.95 (d, 1H, J = 8 Hz); 8.14 (d, 1H, J = 7.5 Hz). High resolution mass m/z for $C_{23}H_{27}N_3NaO_7S$ $(M + Na^+)^+$: calculated 512.1467; measured 512.1458 |
| 81 | | (S)-5-((S)-1,5-diamino-1,5-dioxopentan-2-ylamino)-5-oxo-4-(3-(4-(thiophen-2-yl)phenyl)propanamido)pentanoic acid | Ascentis Express: $t_R$ 3.85 min $\epsilon_{285}$ 20000 $M^{-1} \cdot cm^{-1}$ High resolution mass m/z for $C_{23}H_{29}N_4O_6S$ $(M + H^+)^+$: calculated 489.1808; measured 489.1795 |

TABLE III-continued

| | Formula | Name | Analytical data |
|---|---|---|---|
| 82 | | (S)-5-((S)-1,6-diamino-1-oxohexan-2-ylamino)-5-oxo-4-(3-(4-(thiophen-2-yl)phenyl)propanamido)pentanoic acid | Ascentis Express:<br>$t_R$ = 4.10 min<br>$\epsilon_{285}$ = 18487 $M^{-1} \cdot cm^{-1}$<br>High resolution mass m/z<br>for $C_{24}H_{33}N_4O_5S$<br>$(M + H^+)^+$: calculated<br>489.2172; measured<br>489.2190 |
| 83 | | (S)-5-((S)-1-amino-3-carboxy-1-oxopropan-2-ylamino)-5-oxo-4-(3-(4-(thiophen-2-yl)phenyl)propanamido)pentanoic acid | Ascentis Express:<br>$t_R$ = 4.55 min<br>$\epsilon_{285}$ = 18156 $M^{-1} \cdot cm^{-1}$<br>High resolution mass m/z<br>for $C_{22}H_{25}N_3NaO_7S$<br>$(M + Na^+)^+$: calculated<br>489.1311; measured<br>498.1314 |
| 84 | | (S)-5-((S)-1-amino-3-(4-hydroxyphenyl)-1-oxopropan-2-ylamino)-5-oxo-4-(3-(4-(thiophen-2-yl)phenyl)propanamido)pentanoic acid | Ascentis Express:<br>$t_R$ = 4.52 min<br>$\epsilon_{285}$ = 22000 $M^{-1} \cdot cm^{-1}$<br>High resolution mass m/z<br>for $C_{27}H_{29}N_3NaO_6S$<br>$(M + Na^+)^+$: calculated<br>546.1674; measured<br>546.1661 |
| 85 | | (S)-5-((S)-1-amino-1-oxopropan-2-ylamino)-5-oxo-4-(3-(4-(thiophen-2-yl)phenyl)propanamido)pentanoic acid | Ascentis Express:<br>$t_R$ = 4.18 min<br>$\epsilon_{285}$ = 18627 $M^{-1} \cdot cm^{-1}$<br>High resolution mass m/z<br>for $C_{21}H_{26}N_3O_5S$<br>$(M + H^+)^+$: calculated<br>432.1593; measured<br>432.1580 |

TABLE III-continued

| | Formula | Name | Analytical data |
|---|---|---|---|
| 86 | | (S)-5-((S)-1-amino-3-(1H-imidazol-4-yl)-1-oxopropan-2-ylamino)-5-oxo-4-(3-(4-(thiophen-2-yl)phenyl)propanamido)pentanoic acid | Ascentis Express:<br>$t_R$ = 3.69 min<br>$\epsilon_{285}$ = 19433 M$^{-1}$·cm$^{-1}$<br>High resolution mass m/z for $C_{24}H_{28}N_5O_5S$<br>$(M + H^+)^+$: calculated 498.1811; measured 498.1807 |
| 87 | | (S)-5-((S)-1-amino-3-hydroxy-1-oxopropan-2-ylamino)-5-oxo-4-(3-(4-(thiophen-2-yl)phenyl)propanamido)pentanoic acid | Ascentis Express:<br>$t_R$ = 3.94 min<br>$\epsilon_{285}$ = 15886 M$^{-1}$·cm$^{-1}$<br>High resolution mass m/z for $C_{21}H_{26}N_3O_6S$<br>$(M + H^+)^+$: calculated 448.1542; measured 448.1542 |
| 88 | | (S)-5-((S)-1-amino-4-methyl-1-oxopentan-2-ylamino)-5-oxo-4-(3-(4-(thiophen-2-yl)phenyl)propanamido)pentanoic acid | Ascentis Express:<br>$t_R$ = 5.13 min<br>$\epsilon_{285}$ = 20833 M$^{-1}$·cm$^{-1}$<br>High resolution mass m/z for $C_{24}H_{31}N_3NaO_5S$<br>$(M + Na^+)^+$: calculated 496.1882; measured 496.1878 |
| 89 | | (S)-5-((S)-3-(carboxymethyl)piperidin-1-yl)-5-oxo-4-(3-(4-(thiophen-2-yl)phenyl)propanamido)pentanoic acid | Ascentis Express:<br>$t_R$ = 4.97 min<br>$\epsilon_{288}$ = 28274 M$^{-1}$·cm$^{-1}$<br>High resolution mass m/z for $C_{25}H_{31}N_2O_6S$<br>$(M + H^+)^+$: calculated 487.1903; measured 487.1894 |

TABLE III-continued

| | Formula | Name | Analytical data |
|---|---|---|---|
| 90 | | (S)-5-(3-(carboxymethyl)phenylamino)-5-oxo-4-(3-(4-(thiophen-2-yl)phenyl)propanamido)pentanoic acid | Ascentis Express:<br>$t_R$ = 5.30 min<br>$\epsilon_{246}$ = 16666 $M^{-1} \cdot cm^{-1}$<br>$\epsilon_{282}$ = 25000 $M^{-1} \cdot cm^{-1}$<br>High resolution mass m/z for $C_{26}H_{26}N_2NaO_6S$ $(M + Na^+)^+$: calculated 517.1409; measured 517.1390 |
| 91 | | (S)-5-amino-4-((S)-4-carboxy-2-(3-(4-(5-methylthiophen-2-yl)phenyl)propanamido)butanamido)-5-oxopentanoic acid | Ascentis Express:<br>$t_R$ = 4.61 min<br>$\epsilon_{292}$ = 21893 $M^{-1} \cdot cm^{-1}$<br>High resolution mass m/z for $C_{24}H_{29}N_3NaO_7S$ $(M + Na^+)^+$: calculated 526.1624; measured 526.1620 |
| 92 | | (S)-5-amino-4-((S)-4-carboxy-2-(3-(4-(5-phenylthiophen-2-yl)phenyl)propanamido)butanamido)-5-oxopentanoic acid | Ascentis Express:<br>$t_R$ = 5.72 min<br>$\epsilon_{338}$ = 30000 $M^{-1} \cdot cm^{-1}$<br>$^1$H NMR (DMSO $d_6$): δ 1.76 (m, 2H); 1.91 (m, 2H); 2.22 (m, 4H); 2.51 (m, 2H); 2.82 (m, 2H); 4.21 (m, 2H); 7.11 (s, 1H); 7.30 (m, 4H); 7.44 (t, 2H, J = 7.25 Hz); 7.49 (d, 1H, J = 4 Hz); 7.54 (d, 1H, J = 3.75 Hz); 7.60 (d, 2H, J = 8 Hz); 7.70 (d, 2H, J = 7.5 Hz); 7.96 (d, 1H, J = 7.75 Hz); 8.16 (d, 1H, J = 7.25 Hz).<br>High resolution mass m/z for $C_{29}H_{31}N_3NaO_7S$ $(M + Na^+)^+$: calculated 588.1780; measured 588.1776 |
| 93 | | (S)-5-amino-4-((S)-2-(3-(4-(5-(benzo[d]thiazol-2-yl)thiophen-2-yl)phenyl)propanamido)-4-carboxybutanamido)-5-oxopentanoic acid | Ascentis Express:<br>$t_R$ = 4.97 min<br>$\epsilon_{320}$ = 46154 $M^{-1} \cdot cm^{-1}$<br>High resolution mass m/z for $C_{30}H_{31}N_4O_7S_2$ $(M + H^+)^+$: calculated 623.1634; measured 623.1616 |

TABLE III-continued

| | Formula | Name | Analytical data |
|---|---|---|---|
| 94 | | (S)-5-amino-4-((S)-4-carboxy-2-(3-(4-(4-methylthiophen-2-yl)phenyl)propanamido)butanamido)-5-oxopentanoic acid | Ascentis Express: $t_R$ = 4.58 min $\varepsilon_{290}$ = 16369 $M^{-1} \cdot cm^{-1}$ High resolution mass m/z for $C_{24}H_{30}N_3O_7S$ $(M + H^+)^+$: calculated 504.1804; measured 504.1782 |
| 95 | | (S)-5-amino-4-((S)-4-carboxy-2-(3-(4-(4-phenylthiophen-2-yl)phenyl)propanamido)butanamido)-5-oxopentanoic acid | Acentis Express: $t_R$= 5.61 min $\varepsilon_{259}$ = 34583 $M^{-1} \cdot cm^{-1}$ $^1$H NMR (DMSO d$_6$): δ 1.76 (m, 2H); 1.91 (m, 2H); 2.22 (m, 4H); 2.51 (m, 2H); 2.84 (m, 2H); 4.21 (m, 2H) 7.11 (s, 1H); 7.30 (m, 4H), 7.44 (t, 2H, J = 7 Hz); 7.65 (d, 2H, J = 8.25 Hz); 7.79 (d, 2H, J = 7.25 Hz); 7.85 (s, 1H); 7.96 (m, 2H); 8.16 (d, 1H, J = 7.5 Hz). High resolution mass m/z for $C_{29}H_{32}N_3O_7S$ $(M + H^+)^+$: calculated 566.1961; measured 566.1953 |
| 96 | | (S)-5-amino-4-((R)-4-carboxy-2-(3-(4-(4-phenylthiophen-2-yl)phenyl)propanamido)butanamido)-5-oxopentanoic acid | Ascentis Express: $t_R$ = 5.64 min $\varepsilon_{259}$ = 36111 $M^{-1} \cdot cm^{-1}$ High resolution mass m/z for $C_{29}H_{31}N_3NaO_7S$ $(M + Na^+)^+$: calculated 588.1780; measured 588.1770 |

TABLE III-continued

| | Formula | Name | Analytical data |
|---|---|---|---|
| 97 | 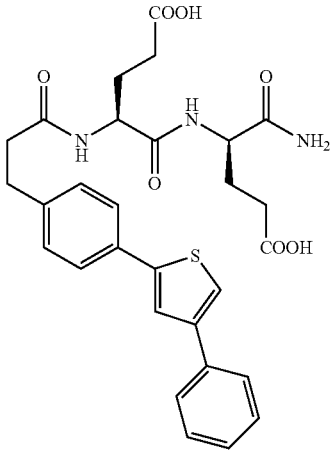 | (R)-5-amino-4-((S)-4-carboxy-2-(3-(4-(4-phenylthiophen-2-yl)phenyl)propanamido)butanamido)-5-oxopentanoic acid | Ascentis Express:<br>$t_R$ = 5.63 min<br>$\epsilon_{259}$ = 31176 $M^{-1} \cdot cm^{-1}$<br>High resolution mass m/z<br>for $C_{29}H_{31}N_3NaO_7S$<br>$(M + Na^+)^+$: calculated<br>588.1780; measured<br>588.1802 |
| 98 | 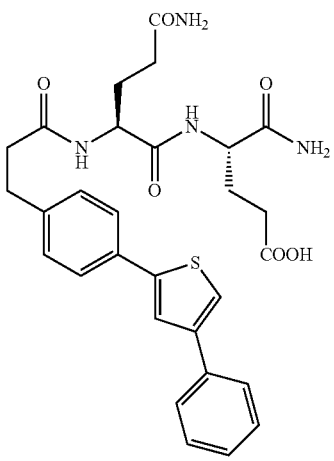 | (S)-4-amino-5-((S)-5-amino-5-oxo-2-(3-(4-(4-phenylthiophen-2-yl)phenyl)propanamido)pentanamido)-5-oxopentanoic acid | Ascentis Express:<br>$t_R$ = 5.35 min<br>$\epsilon_{259}$ = 32857 $M^{-1} \cdot cm^{-1}$<br>High resolution mass m/z<br>for $C_{29}H_{32}N_4NaO_6S$<br>$(M + Na^+)^+$: calculated<br>587.1940; measured<br>587.1938 |
| 99 | 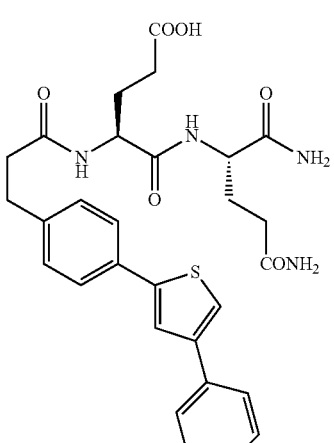 | (S)-5-((S)-1,5-diamino-1,5-dioxopentan-2-ylamino)-5-oxo-4-(3-(4-(4-phenylthiophen-2-yl)phenyl)propanamido)pentanoic acid | Ascentis Express:<br>$t_R$ = 5.38 min<br>$\epsilon_{259}$ = 28729 $M^{-1} \cdot cm^{-1}$<br>High resolution mass m/z<br>for $C_{29}H_{32}N_4NaO_6S$<br>$(M + Na^+)^+$: calculated<br>587.1940; measured<br>587.1964 |

TABLE III-continued

| | Formula | Name | Analytical data |
|---|---|---|---|
| 100 | | (S)-5-amino-4-((S)-3-carboxy-2-(3-(4-(4-phenylthiophen-2-yl)phenyl)propanamido)propanamido)-5-oxopentanoic acid | Ascentis Express:<br>$t_R$ = 5.64 min<br>$\epsilon_{259}$ = 35652 $M^{-1} \cdot cm^{-1}$<br>High resolution mass m/z for $C_{28}H_{29}N_3NaO_7S$ $(M + Na^+)^+$: calculated 574.1624; measured 574.1617 |
| 101 | | (S)-5-((S)-1-amino-3-carboxy-1-oxopropan-2-ylamino)-5-oxo-4-(3-(4-(4-phenylthiophen-2-yl)phenyl)propanamido)pentanoic acid | Ascentis Express:<br>$t_R$ = 5.63 min<br>$\epsilon_{259}$ = 30797 $M^{-1} \cdot cm^{-1}$<br>High resolution mass m/z for $C_{28}H_{29}N_3NaO_7S$ $(M + Na^+)^+$: calculated 574.1624; measured 574.1645 |
| 102 | | (S)-6-((S)-1-amino-4-carboxy-1-oxobutan-2-ylamino)-6-oxo-5-(3-(4-(4-phenylthiophen-2-yl)phenyl)propanamido)hexanoic acid | Ascentis Express:<br>$t_R$ = 5.69 min<br>$\epsilon_{259}$ = 45833 $M^{-1} \cdot cm^{-1}$<br>High resolution mass m/z for $C_{30}H_{33}N_3NaO_7S$ $(M + Na^+)^+$: calculated 602.1937; measured 602.1938 |

TABLE III-continued

| | Formula | Name | Analytical data |
|---|---|---|---|
| 103 | 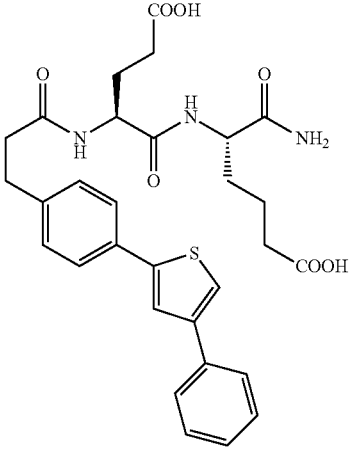 | (S)-6-amino-5-((S)-4-carboxy-2-(3-(4-(4-phenylthiophen-2-yl)phenyl)propanamido)butanamido)-6-oxohexanoic acid | Ascentis Express:<br>$t_R$ = 5.67 min<br>$\epsilon_{259}$ = 32482 $M^{-1} \cdot cm^{-1}$<br>High resolution mass m/z<br>for $C_{30}H_{33}N_3NaO_7S$<br>$(M + Na^+)^+$: calculated<br>602.1937; measured<br>602.1938 |
| 104 | 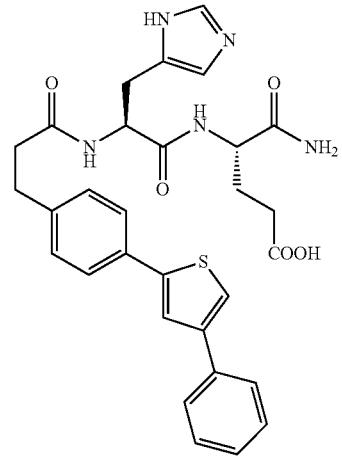 | (S)-4-((S)-3-(1H-imidazol-5-yl)-2-(3-(4-(4-phenylthiophen-2-yl)phenyl)propanamido)propanamido)-5-amino-5-oxopentanoic acid | Ascentis Express:<br>$t_R$ = 5.17 min<br>$\epsilon_{259}$ = 32335 $M^{-1} \cdot cm^{-1}$<br>High resolution mass m/z<br>for $C_{30}H_{32}N_5O_5S$<br>$(M + H^+)^+$: calculated<br>574.2124; measured<br>574.2108 |
| 105 | 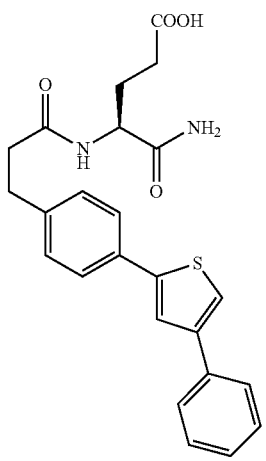 | (S)-5-amino-5-oxo-4-(3-(4-(4-phenylthiophen-2-yl)phenyl)propanamido)pentanoic acid | Ascentis Express:<br>$t_R$ = 5.93 min<br>$\epsilon_{259}$ = 36526 $M^{-1} \cdot cm^{-1}$<br>High resolution mass m/z<br>for $C_{24}H_{24}N_2NaO_4S$<br>$(M + Na^+)^+$: calculated<br>459.1354; measured<br>459.1346 |

TABLE III-continued

| | Formula | Name | Analytical data |
|---|---|---|---|
| 106 | [structure] | (S)-5-(3-(carboxymethyl)phenylamino)-5-oxo-4-(3-(4-(4-phenylthiophen-2-yl)phenyl)propanamido)pentanoic acid | Ascentis Express: $t_R$ = 6.68 min $\epsilon_{259}$ = 4790 $M^{-1} \cdot cm^{-1}$ High resolution mass m/z for $C_{32}H_{30}N_2NaO_6S$ $(M + Na^+)^+$: calculated 593.1722; measured 593.1748 |
| 107 | [structure] | (S)-5-amino-4-((S)-4-carboxy-2-(3-(4-(3-methylthiophen-2-yl)phenyl)propanamido)butanamido)-5-oxopentanoic acid | Ascentis Express: $t_R$ = 4.53 min $\epsilon_{271}$ = 1472 $M^{-1} \cdot cm^{-1}$ High resolution mass m/z for $C_{24}H_{29}N_3NaO_7S$ $(M + Na^+)^+$: calculated 526.1624; measured 526.1627 |
| 95 bis | [structure] | (S)-5-amino-4-((S)-4-carboxy-2-((R)-3-carboxy-2-(4-(4-phenylthiophen-2-yl)benzyl)propanamido)butanamido)-5-oxopentanoic acid | Ascentis Express: $t_R$ = 5.55 min $\epsilon_{272}$ = 18230 $M^{-1} \cdot cm^{-1}$ High resolution mass m/z for $C_{31}H_{34}N_3O_9S$, $(M + H^+)^+$: calculated 624.2010; measured 624.1999. |

Synthesis of the compound (95 bis) carrying a carboxymethyl group —CH$_2$COOH at R$_4$ (Formula 95bis)

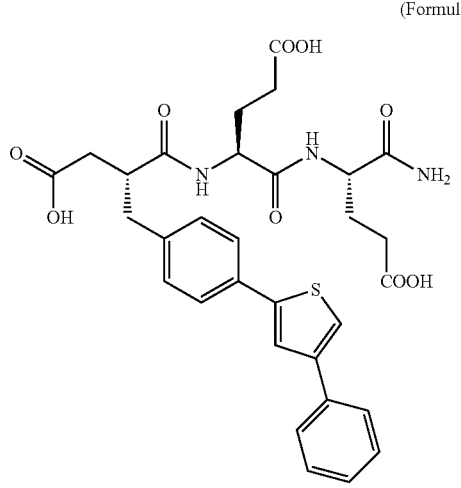

The compound (95 bis) carrying a carboxymethyl group at R$_4$ is synthesized according to the same protocol as the compounds (3) to (107) described above, only the nature of the malonic block incorporated on the solid support having been modified. Indeed, it is in this case a question of incorporating a bifunctionalized malonic block, the latter being obtained in four steps according to the following general synthesis scheme:

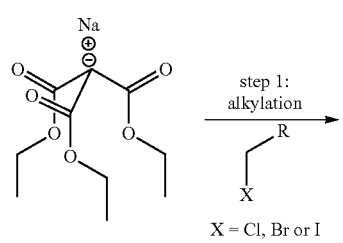

X = Cl, Br or I

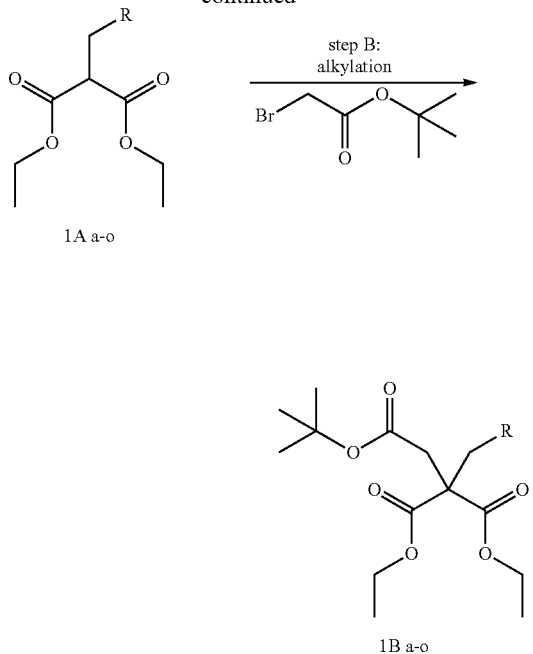

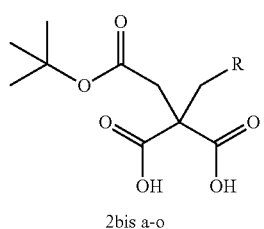

1a-o

R having the same meaning as previously.

The alkylation step 1 is carried out according to the procedure described previously for the synthesis of the monofunctionalized malonic blocks.

Step A: Partial Saponification Step

The triester 1 (3.93 mmol) was solubilized in tetrahydrofuran (10 ml), and sodium ethanolate (4.71 mmol, 1.2 eq) was added dropwise at ambient temperature. The completion of the reaction was verified by thin layer chromatography (TLC) with an eluent mixture (cyclohexane CHX/ethyl acetate EtOAc: 9/1).

The reaction mixture was then poured into a solution of ethyl acetate EtOAc/1M HCl water (1/1:10 ml/10 ml). The aqueous phase was extracted with ethyl acetate EtOAc (2×10 ml). The organic phases were combined and then washed with a saturated solution of sodium chloride NaCl (20 ml) and, finally, dried over anhydrous magnesium sulfate (MgSO$_4$). The solvent was then concentrated under vacuum and the crude product was purified by flash chromatography (CHX/EtOAc), to give the diesters 1A.

Diethyl 2-(4-iodobenzyl)malonate 1Ab

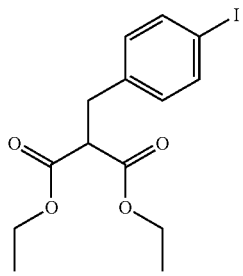

Prepared from the triester 1b according to the partial saponification protocol, to give the title compound in the form of a colorless oil (yield 82%).

$^1$H NMR (CDCl$_3$): δ 1.21 (t, 6H, J=6.75 Hz); 3.15 (d, 2H, J=8 Hz); 3.59 (t, 1H, J=8 Hz) 4.16 (q, 4H, J=6.75 Hz); 6.96 (d, 2H, J=8.25 Hz); 7.59 (d, 2H, J=8.25 Hz).

$^{13}$C NMR (CDCl$_3$): δ 14.16; 34.25; 53.69; 61.76; 92.25; 131.07; 137.68; 137.70; 168.76.

Step B: Alkylation Step

The diester 1B (3.93 mmol) was solubilized in anhydrous tetrahydrofuran (10 ml) under an inert atmosphere. The reaction mixture was then cooled to 0° C. and sodium hydride (4.32 mmol, 1.1 eq) was added. After stirring for 10 minutes at 0° C., tert-butyl 2-bromoactetate (5.89 mmol, 1.5 eq) was added and the reaction mixture was stirred at ambient temperature. The completion of the reaction was verified by thin layer chromatography (TLC) with an eluent mixture (cyclohexane CHX/ethyl acetate EtOAc: 9/1). The reaction mixture was taken up and then poured into water/EtOAc (1/1: ml/10 ml). The aqueous phase was extracted with ethyl acetate EtOAc (2×10 ml). The organic phases were combined, washed with a saturated NaCl solution (20 ml) and dried over anhydrous MgSO$_4$. After evaporation, the crude solid was triturated from DCM (1 ml) and then filtered, to give the derivatives 1B.

1-tert-butyl 2,2-diethyl-3-(4-iodophenyl)propane-1,2,2-tricarboxylate 1Bb

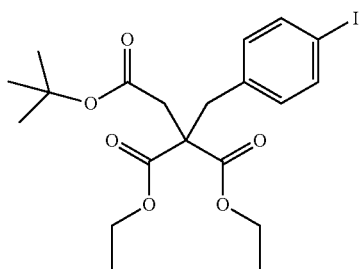

Prepared from the diester 1Ab according to the alkylation protocol (step B), to give the title compound in the form of a colorless oil (yield 95%).

$^1$H NMR (CDCl$_3$): δ 1.21 (t, 6H, J=6.75 Hz); 1.46 (s, 9H), 2.75 (s, 2H); 3.31 (s, 2H) 4.19 (q, 4H, J=6.75 Hz); 6.85 (d, 2H, J=8.25 Hz); 7.58 (d, 2H, J=8.25 Hz).

$^{13}$C NMR (CDCl$_3$): δ 13.97; 27.98; 37.62; 37.81; 56.42; 61.70; 81.39; 92.70; 132.09; 135.60; 137.41; 169.63; 169.76.

2-(2-(tert-butoxy)-2-oxoethyl)-2-(4-iodobenzyl)malonic acid 2b bis

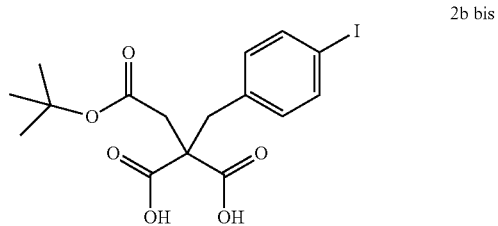 [SMILES: CC(C)(C)OC(=O)CC(Cc1ccc(I)cc1)(C(=O)O)C(=O)O]

Prepared from the compound 1Bb according to the saponification protocol (step 2), to give the title compound in the form of an off-white solid (yield 65%).

$^1$H NMR (MeOH d$_4$): δ 1.38 (s, 9H), 2.94 (s, 2H); 3.12 (s, 2H). 6.85 (d, 2H, J=8 Hz); 7.56 (d, 2H, J=8 Hz).

High resolution mass m/z for C$_{16}$H$_{20}$INO$_6$ (M+H$^+$)$^+$, calculated 435.0299; measured 435.0310.

The saponification step 2 is carried out according to the procedure described previously for the synthesis of the monofunctionalized malonic blocks.

The bifunctionalized malonic blocks thus synthesized are then incorporated on a solid support, and the pseudopeptides obtained are modified via 1,3-dipolar cycloaddition reactions or couplings with palladium (Suzuki or Sonogashira reaction) as previously described.

The analytical data regarding the compound (95 bis) appear in table III above.

The compound (95 bis) was then evaluated on human MMPs, and compared with the compound (95). The results appear in the following table IV:

TABLE IV

|  | MMP-1h | MMP-2h | MMP-3h | MMP-7h | MMP-8h | MMP-9h | MMP-10h | MMP-12h | MMP-13h | MMP-14h |
|---|---|---|---|---|---|---|---|---|---|---|
| Ki (nM) Compound (95) | >10000 | >1000 | >1000 | >1000 | 410 | >10000 | 872 | 1.92 | 684 | >2500 |

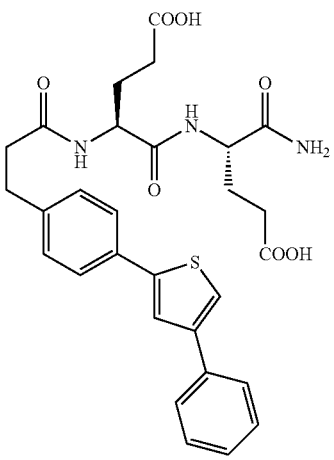

| | | | | | | | | | | |
|---|---|---|---|---|---|---|---|---|---|---|
| Selectivity factor/MMP12 | 5208 | 520 | 520 | 520 | 213 | 5200 | 454 | 1 | 356 | 1300 |
| Ki (nM) Compound (95bis) | >1000 | 401 | 579 | >1000 | 520 | >1000 | 80 | 0.3 | 198 | 118 |

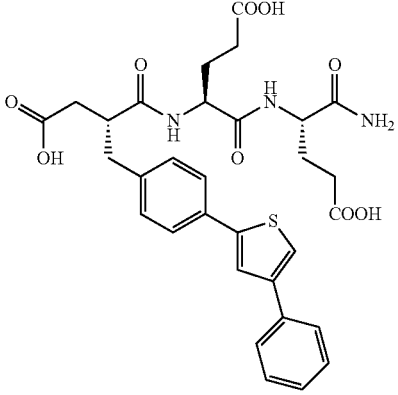

| | | | | | | | | | | |
|---|---|---|---|---|---|---|---|---|---|---|
| Selectivity factor/MMP12 | 3333 | 1340 | 1930 | 3333 | 1730 | 3333 | 270 | 1 | 660 | 395 |

It is observed that, when $R_4$ is a carboxymethyl group —$CH_2COOH$, the affinity of the resulting compound (formula 95 bis) with respect to MMP-12, compared with the compound of formula 95, is improved by a factor of 6 (from 1.92 nM to 0.3 nM). As regards the selectivity factors for the other members of the MMP family, they were either maintained, or improved. Only the selectivity with respect to MMP-14 is slightly reduced compared with the compound (95).

Evaluation of the Pseudopeptides on the MMPs:

The inhibition tests and the evaluation of the inhibition constants (Ki) on the various MMPs were carried out as described by Devel et al. (Devel et al. 2006 J. Biol. Chem. (7))

The results obtained are reported in tables I, II and IV.

Evaluation of the Stability in the Blood and of the Plasma Concentration of the Compounds of Formula (1), in Mice:

Experiments on the compounds of formulae (40) and (91) made it possible to evaluate the stability of these compounds in the blood, and also their plasma concentration in mice after an infusion over a period of 30 minutes.

Stability Test:

After 24 hours in mouse blood, and after LC-MS (Liquid Chromatography-Mass Spectrometry) analysis and confirmation of the identity by fragmentation by MS/MS mass spectrometry, 50 fmol (solution at 5 nM for an initial solution at 10 nM at t=0) of the compound (40) are detected in intact form. No by-product resulting from the compound (40) was detected. The loss of 50% of the starting material can be attributed to a phenomenon of nonspecific association of the compound with the wall of the eppendorf. It should be noted that this 50% loss of the compound was also observed after 24 hours for a solution at 10 nM in PBS buffer or in a solution at 1 μM of PBS (Bovine Serum Albumin).

Determination of the Plasma Concentration:

After infusion in five mice of a solution of the compound (91) at 10 mg/kg (i.e. 0.2 mg/50 l, i.e. at 8 mM in a PBS buffer solution) over a period of 30 minutes, and sampling of blood after 5 minutes, the blood is extracted and an average plasma concentration for the compound (91) of 1 μM was determined by means of an inhibition test on MMP-8. The strict identity of the compound (91) was, moreover, confirmed by LC-MS analysis and MS/MS fragmentation.

Synthesis of the Compounds of Formula (2) Carrying a TAG Label

The labeled compounds of formula (2) can be synthesized according to the following scheme 3:

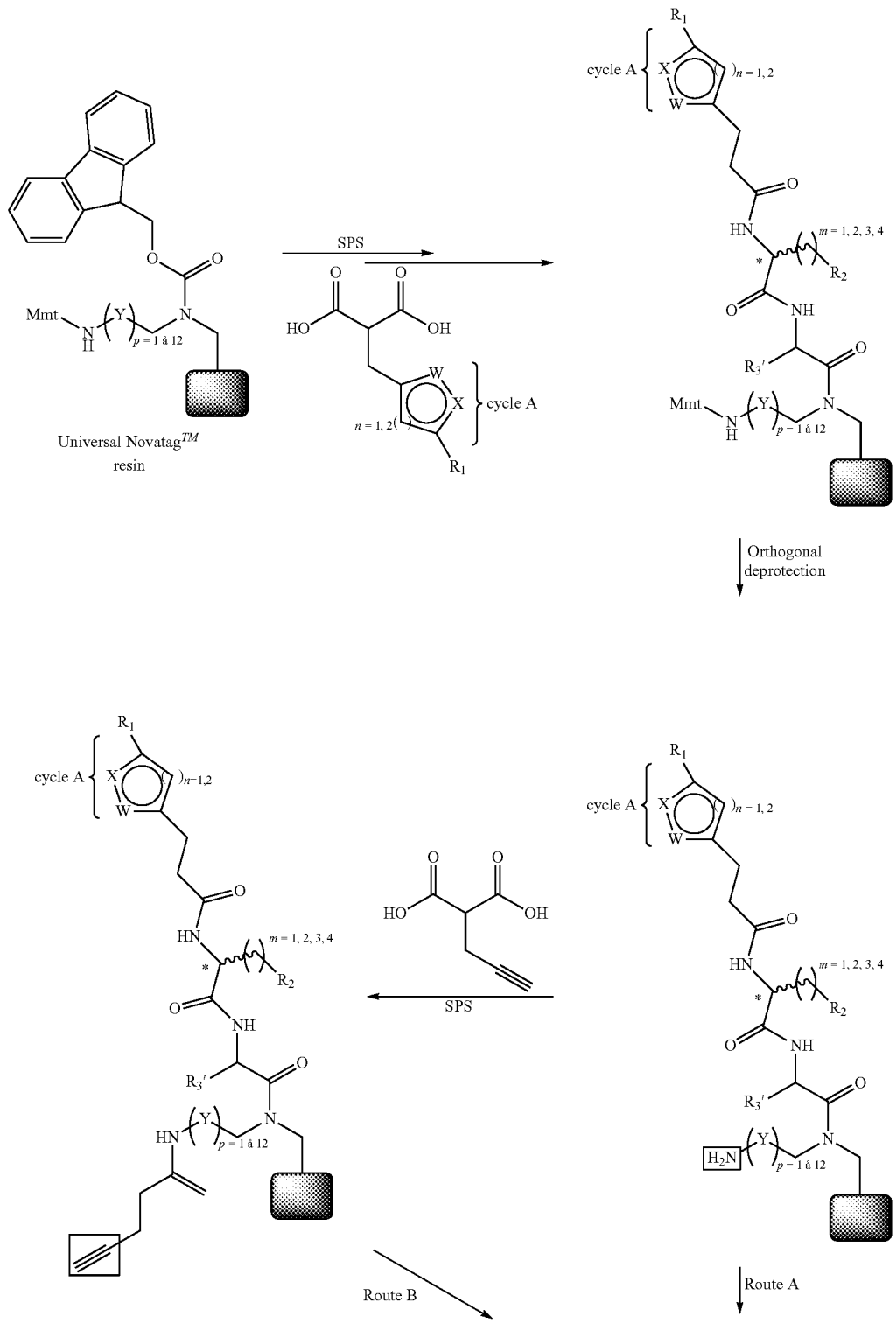

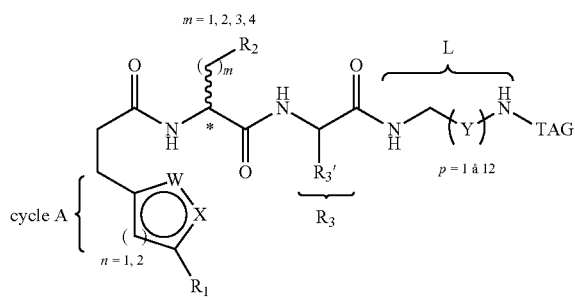

The compounds of general formula (1) can be labeled in the C-terminal position according to the various synthesis routes represented above in scheme 3. After construction of the peptide sequence on a solid support, the malonic block is incorporated, and then the ring A is formed by 1,3-dipolar cycloaddition or functionalized by coupling with palladium, as previously described (Suziki reaction or Sonogashira reaction). An orthogonal deprotection without cleavage of the solid support can then be carried out. The amine thus freed can: a) either react with an activated ester (route A), or b) be pre-modified and converted into a new chemical function allowing the introduction of the TAG according to a different route (route B).

The various synthesis routes and imaging techniques used according to the nature of the TAG label are summarized in table V below:

TABLE V

| Structure of the TAG | Synthesis route | Imaging technique | References |
|---|---|---|---|
| (triazole-PEG-$^{18}F$ structure) | Route B | PET | (11) |
| ($^{99m}Tc$ macrocycle structure) | Route A | SPECT | (12) |

TABLE V-continued
| Structure of the TAG | Synthesis route | Imaging technique | References |
|---|---|---|---|
| 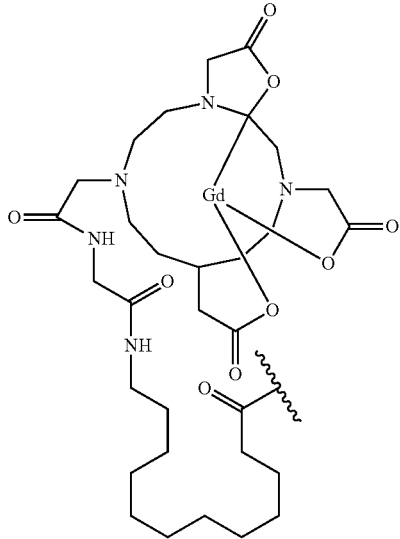 | Route A | MRI | (13) |
| 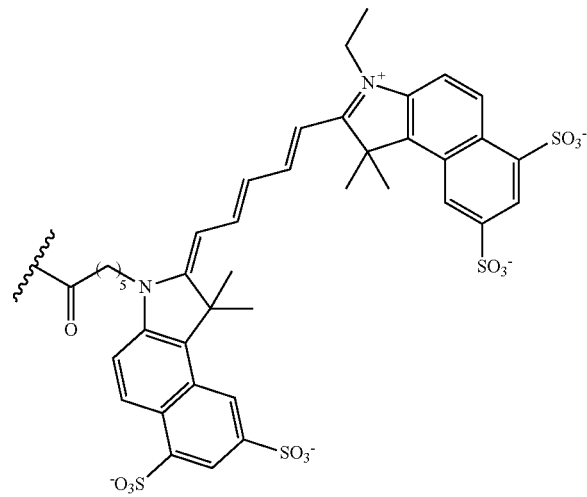 | Route A | NIRF | (14) |
| 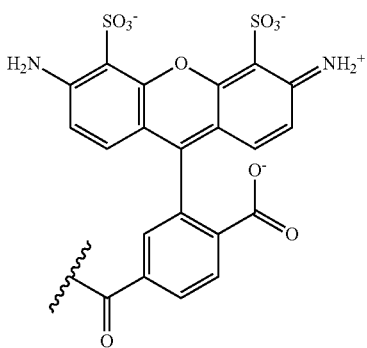 | Route A | NIRF | (14) |
| Peptide label $X_aX_1X_2X_3X_4X_5X_bX_c$ or the retro-inverso form thereof | Route A | SPECT | WO 2010/076654 |

A compound of formula (2) carrying a fluorescent TAG label of Alexa Fluor® type (formula (108)) was synthesized according to scheme 3 above.

Formula (108)

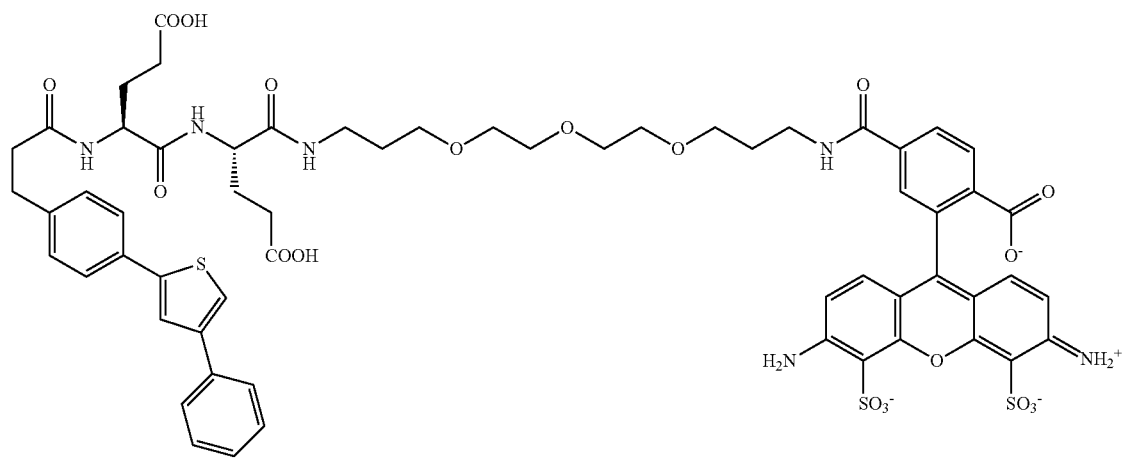

After construction of the peptide sequence, introduction of the malonic block 2b onto a solid support and coupling with palladium under the conditions described above, the primary amine is deprotected in the presence of a solution of HOBt in DCM/TFE:1/1 (0.6 M, 2×30 min). The resin is then washed twice with DMF (for 5 minutes) and twice with DCM (for 5 minutes). A solution of Alexa Fluor® 488 carboxylic acid activated in succinimidyl ester form (1.1 eq, Invitrogen, ref: A20100) in anhydrous DMF is added, and the reaction mixture is then stirred over night at ambient temperature in the dark. The resin is then washed twice with DMF (for 5 minutes) and twice with DCM (for 5 minutes). The pseudopeptide is thus cleaved from its support and then purified as previously described. The analytical data regarding the compound of formula (108) are summarized in table VI below.

TABLE VI

| 108 | [structure] | 2-(6-amino-3-iminio-4,5-disulfonato-3H-xanthen-9-yl)-4-(((5S,8S)-5,8-bis(2-carboxyethyl)-3,6,9-trioxo-1-(4-(4-phenyl-thiophen-2-yl)phenyl)-14,17,20-trioxa-4,7,10-triazatricosan-23-yl)carbamoyl)benzoate | Ascentis Express: $t_R = 5.93$ min $\epsilon_{500}= 808510$ $M^{-1} \cdot cm^{-1}$ Mass m/z for $C_{60}H_{62}N_6O_{20}S_3^{2-}$ $(M + H^+)^+ =$ 1285.4 |
|---|---|---|---|

The compound (108) was then evaluated on human MMPs, and compared with the compound (95). The results appear in the following table VII:

TABLE VII
| | MMP-1h | MMP-2h | MMP-3h | MMP-7h | MMP-8h |
|---|---|---|---|---|---|
| Ki (nM) Compound (95) 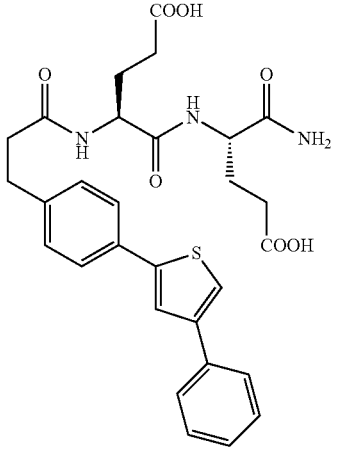 | >10000 | >1000 | >1000 | >1000 | 410 |
| Selectivity factor/MMP12 | 5208 | 520 | 520 | 520 | 213 |
| Ki (nM) Compound (108) 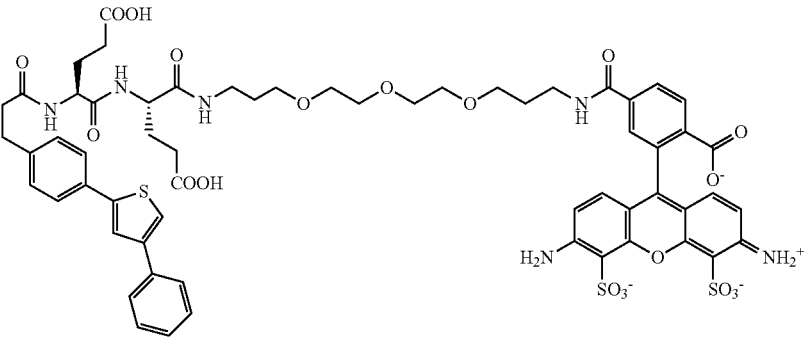 | >10000 | >2500 | >10000 | >10000 | >2500 |

TABLE VII-continued

| | | | | | |
|---|---|---|---|---|---|
| Selectivity factor/MMP12 | 670 | 170 | 670 | 670 | 170 |

| | MMP-9h | MMP-10h | MMP-12h | MMP-13h | MMP-14h |
|---|---|---|---|---|---|
| Ki (nM) Compound (95) | >10000 | 872 | 1.92 | 684 | >2500 |
| Selectivity factor/MMP12 | 5200 | 454 | 1 | 356 | 1300 |
| Ki (nM) Compound (108) | >5000 | 833 | 15 | >1000 | >10000 |
| Selectivity factor/MMP12 | 333 | 55 | 1 | 66 | 670 |

The introduction of a spacer and of a fluorescent group does not cause very much modification of the affinity of the compound of formula (108) with respect to MMP-12, compared with the compound of formula (95) (Ki=15 nM vs Ki=1.92 nM). Furthermore, the compound of formula (108) proves to be quite selective with respect to MMP-12.

LITERATURE REFERENCES (1) Brinckerhoff C E, Matrisian L M. Matrix metalloproteinases: a tail of a frog that became a prince. Nat Rev Mol Cell Biol. 2002 March; 3(3):207-14.

(2) Page-McCaw A, Ewald A J, Werb Z. Matrix metalloproteinases and the regulation of tissue remodelling. Nat Rev Mol Cell Biol. 2007 March; 8(3):221-33.
(3) Egeblad M, Werb Z. New functions for the matrix metalloproteinases in cancer progression. Nat Rev Cancer. 2002 March; 2(3):161-74.
(4) Fingleton B. Matrix metalloproteinases as valid clinical targets.Fingleton B. Curr Pharm Des. 2007; 13(3):333-46.
(5) Hu J, Van den Steen P E, Sang Q X, Opdenakker G. Matrix metalloproteinase inhibitors as therapy for inflammatory and vascular diseases. Nat Rev Drug Discov. 2007 June; 6(6):480-98.
(6) Overall C M, López-Otin C. Strategies for MMP inhibition in cancer: innovations for the post-trial era. Nat Rev Cancer. 2002 September; 2(9):657-72.
(7) Devel L, Rogakos V, David A, Makaritis A, Beau F, Cuniasse P, Yiotakis A, Dive V. Development of selective inhibitors and substrate of matrix metalloproteinase-12. J Biol. Chem. 2006 Apr. 21; 281(16):11152-60.
(8) Engel C K, Pirard B, Schimanski S, Kirsch R, Habermann J, Klingler O, Schlotte V, Weithmann K U, Wendt K U. Structural basis for the highly selective inhibition of MMP-13. Chem. Biol. 2005 February; 12(2):181-9.
(9) Makaritis A, Georgiadis D, Dive V, Yiotakis A. Diastereoselective solution and multipin-based combinatorial array synthesis of a novel class of potent phosphinic metalloprotease inhibitors. Chemistry. 2003 May 9; 9(9):2079-94.
(10) F. A. Jaffer, P. Libby, R. Weissleder, Optical and multimodality molecular imaging: insights into atherosclerosis, Arterioscler Thromb Vasc Biol. 29 2009 1017-1024.
(11) M. Nahrendorf, E. Keliher, B. Marinelli, P. Waterman, P. F. Feruglio, L. Fexon, M. Pivovarov, F. K. Swirski, M. J. Pittet, C. Vinegoni, R. Weissleder, Hybrid PET-optical imaging using targeted probes, Proc. Natl. Acad. Sci. USA 107 2010 7910-7915.
(12) H. Su, F. G. Spinale, L. W. Dobrucki, J. Song, J. Hua, S. Sweterlitsch, D. P. Dione, P. Cavaliere, C. Chow, B. N. Bourke, X.Y. Hu, M. Azure, P. Yalamanchili, R. Liu, E. H. Cheesman, S. Robinson, D. S. Edwards, A. J. Sinusas, Noninvasive targeted imaging of matrix metalloproteinase activation in a murine model of postinfarction remodeling, Circulation. 112 2005 3157-3167.
(13) B. Jastrzebska, R. Lebel, H. Therriault, J. O. McIntyre, E. Escher, B. Guerin, B. Paquette, W. A. Neugebauer, M. Lepage, New enzyme-activated solubility-switchable contrast agent for magnetic resonance imaging: from synthesis to in vivo imaging, J. Med. Chem. 52 2009 1576-1581.
(14) A. Faust, B. Waschkau, J. Waldeck, C. Holtke, H. J. Breyholz, S. Wagner, K. Kopka, O, Schober, W. Heindel, M. Schafers, C. Bremer, Synthesis and evaluation of a novel hydroxamate based fluorescent photoprobe for imaging of matrix metalloproteinases, Bioconjug. Chem. 20 2009 904-912.

The invention claimed is:

1. A compound of formula (1):

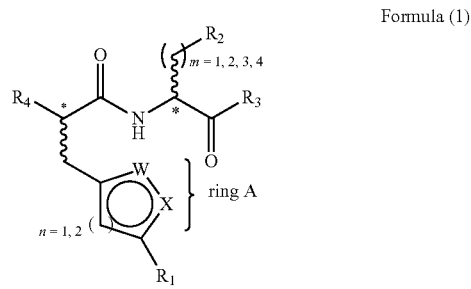

Formula (1)

wherein:

n is 1 or 2, when n is 1, W and X each independently-are O, N or C, when n is 2, W and X are C, $R_1$ is selected from the group consisting of an iodine atom, phenyl, biphenyl, 3'-chlorobiphenyl, phenoxy, phenoxymethyl, phenylethynyl, pyrimidine, 1-methyl-1H-pyrazole, 5-methyl-1,2,4-oxadiazole, 1,2,3-thiadiazole, 1H-pyrrole, thiazole, thiophene, 3a,7a-dihydrobenzo[d]thiazole, 3-aminophenyl, 3-hydroxyphenyl, 3-nitrophenyl, 3-carboxyphenyl, 3'-chlorophenyl, 3,5-dichlorophenyl, 3-methoxyphenyl, 3-hydroxymethylphenyl, and a thiophene ring substituted in at least one position selected from 2, 3, 4, and 5 with a group selected independently for each position from methyl, phenyl, and 3a,7a-dihydrobenzo[d]thiazole, wherein:

m is an integer of 1 to 4, when m is 4, $R_2$ is an amino group, when m is 3, $R_2$ is a carboxylic acid group, when m is 2, $R_2$ is a carboxamide group or a carboxylic acid group, when m is 1, $R_2$ is a carboxylic acid group, a 4-hydroxyphenyl group, a 1H-imidazole group, a hydroxyl group, an isopropyl group, or a methyl group, R₃ is an amino group; a carboxymethylpiperidine group; a carboxymethyl-3-aminophenyl group; or a residue selected from the group consisting of a glutamate residue of L or D configuration, a homoglutamate residue, an aspartate residue, a glutamine residue, an alanine residue, a lysine residue, a tyrosine residue, a histidine residue, a serine residue, and a leucine residue, optionally wherein a terminal carboxylic group of the residue is a carboxamide group —C(=O)NH₂, and R₃ is bonded via an amino group, and R₄ is H or a carboxymethyl group —CH₂COOH, or a diastereoisomer or enantiomer of formula (1).

2. The compound of claim 1, having formula (I-A):

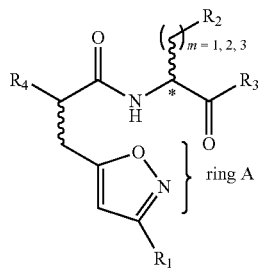

Formula (1-A)

wherein:

R₁ is phenyl, biphenyl or 3'-chlorobiphenyl, m is an integer of 1 to 3, when m is 1 or 3, R₂ is a carboxylic acid group, or a diastereoisomer or enantiomer of formula (1-A).

3. The compound of claim 1, having a formula selected from formulae (3) to (23):

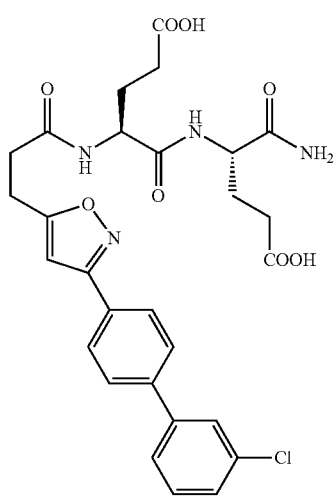

Formula (3)

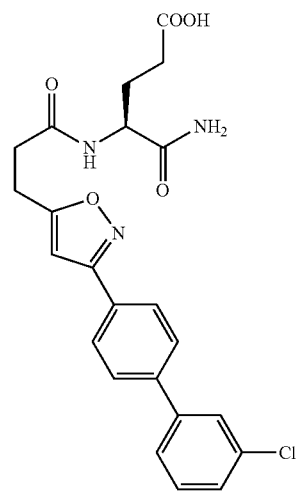

Formula (4)

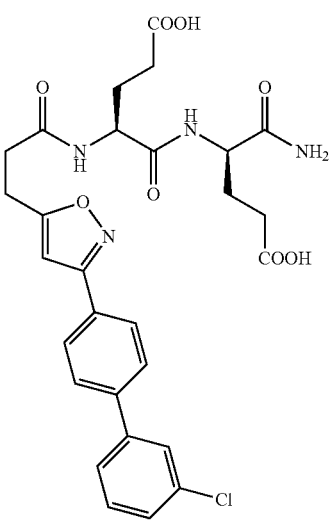

Formula (5)

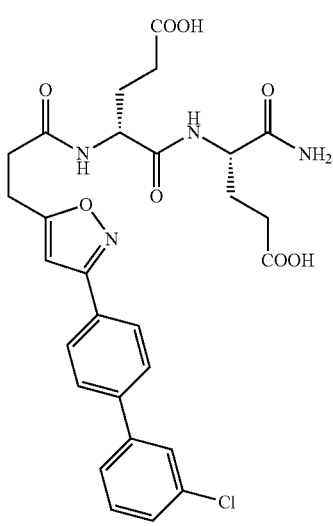

Formula (6)

199
-continued
Formula (7)
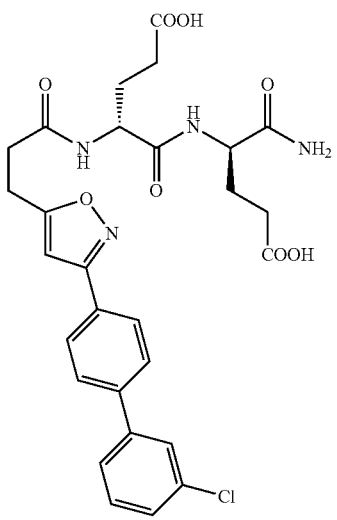
Formula (8)
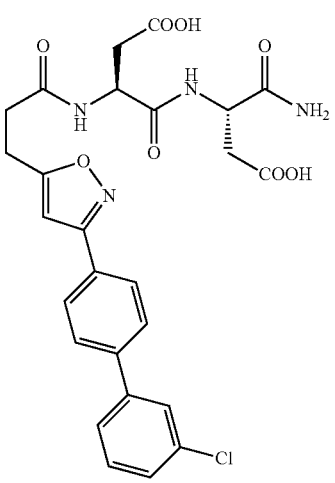
Formula (9)
200
-continued
Formula (10)
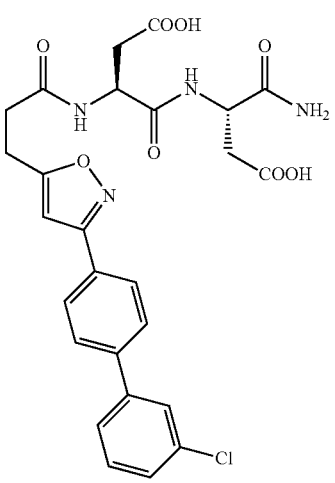
Formula (11)
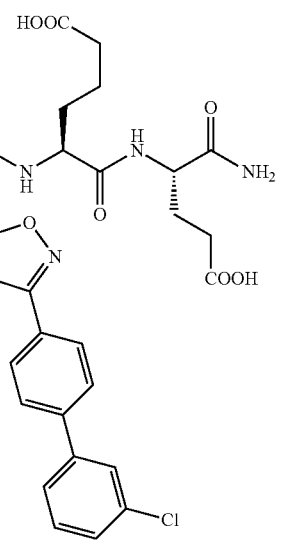
Formula (12)
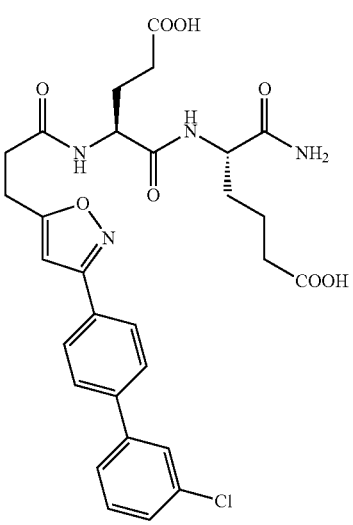

Formula (13)
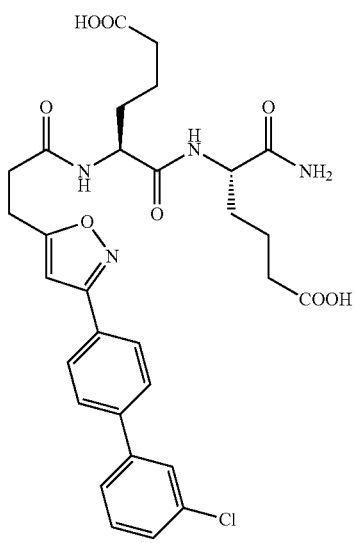
Formula (14)
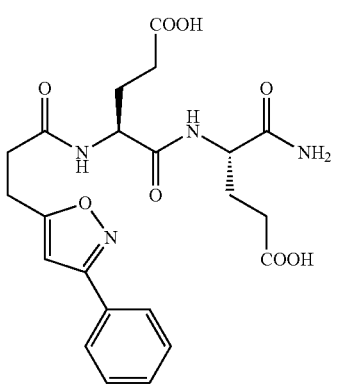
Formula (15)
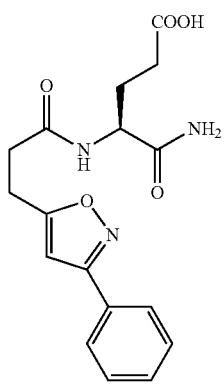
Formula (16)
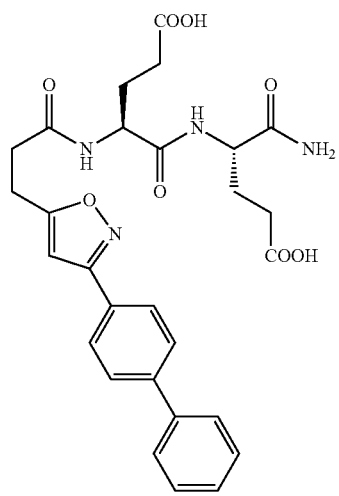
Formula (17)
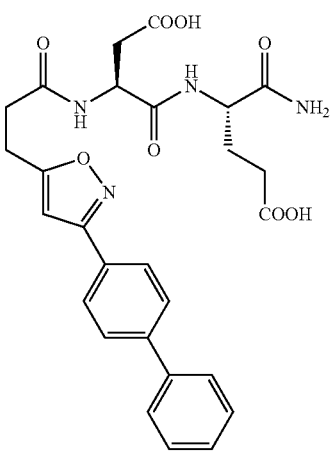
Formula (18)
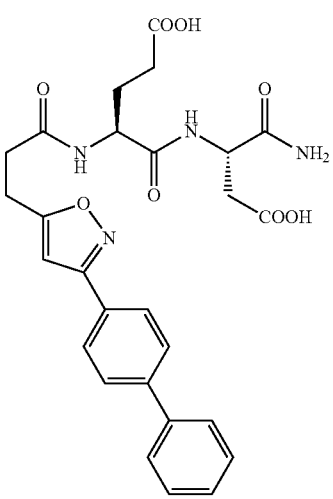

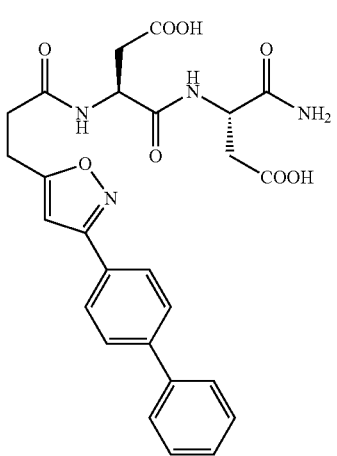
Formula (19)
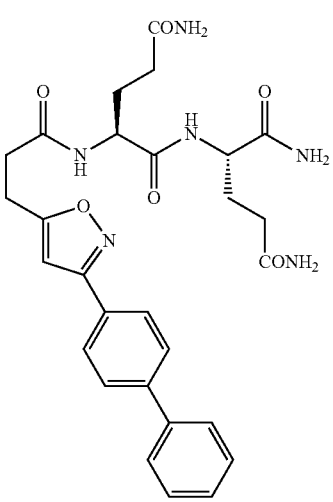
Formula (22)
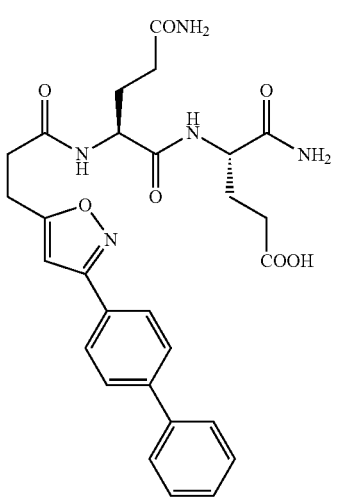
Formula (20)
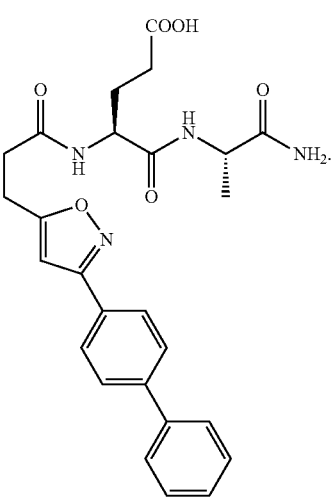
Formula (23)
4. The compound of claim 1, having formula (1-B):
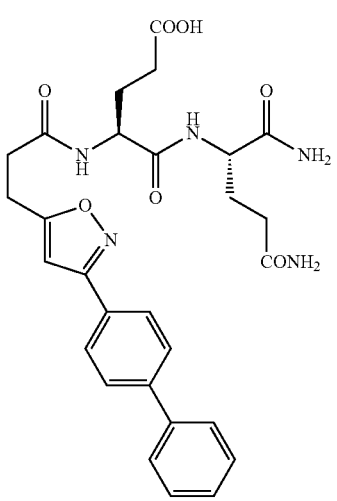
Formula (21)
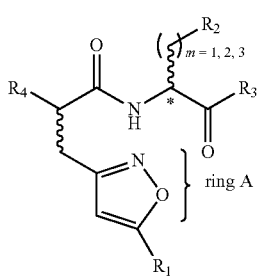
Formula (1-B)
wherein:
$R_1$ is phenyl, biphenyl or 3'-chlorobiphenyl,
m is an integer of 1 to 3,
when m is 1 or 3, $R_2$ is a carboxylic acid group,
or a diastereoisomer or enantiomer of formula (1-B).

5. The compound of claim 4, having formula (25):

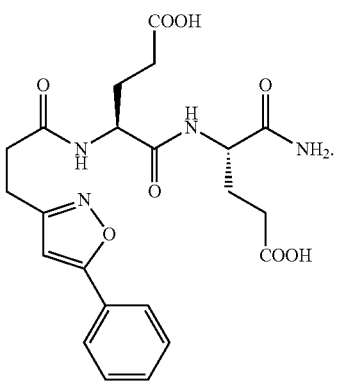
Formula (25)

6. The compound of claim 1, having formula (1-C):

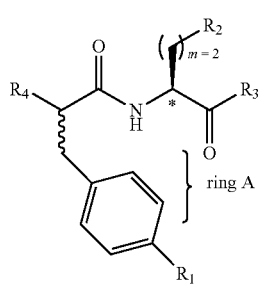
Formula (1-C)

wherein:
$R_1$ is selected from the group consisting of an iodine atom, phenyl, biphenyl, 3'-chlorobiphenyl, phenoxy, phenoxymethyl, phenylethynyl, pyrimidine, 1-methyl-1H-pyrazole, 5-methyl-1,2,4-oxadiazole, 1,2,3-thiadiazole, 1H-pyrrole, thiazole, thiophene and 3a,7a-dihydrobenzo[d]thiazole, m is 2, $R_2$ is a carboxylic acid group, or a diastereoisomer or enantiomer of formula (1-C).

7. The compound of claim 6, having a formula selected from formulae (28) to (39):

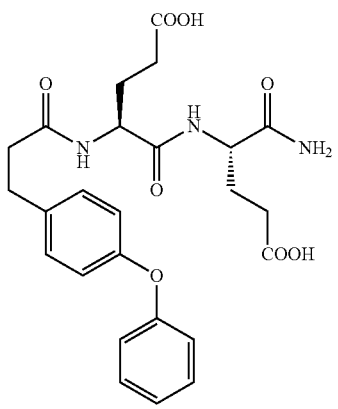
Formula (28)

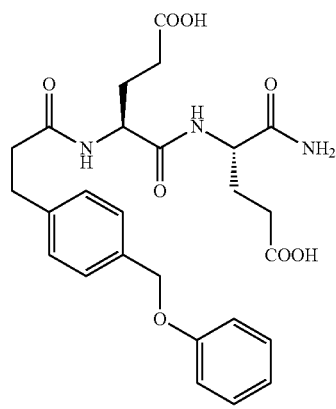
Formula (29)

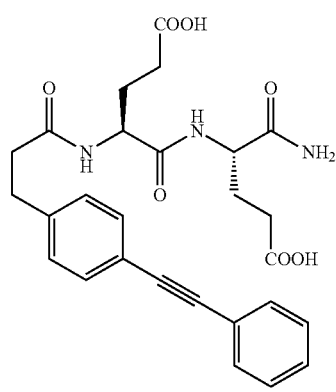
Formula (30)

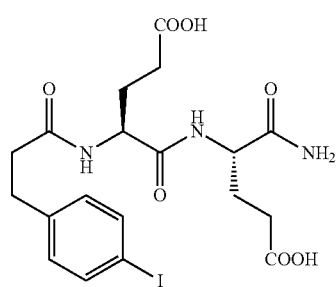
Formula (31)

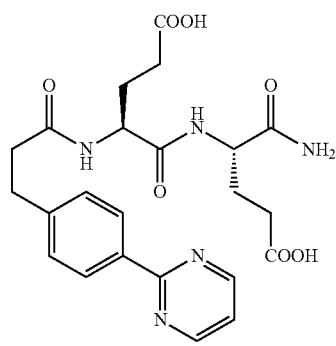
Formula (32)

-continued
Formula (33)
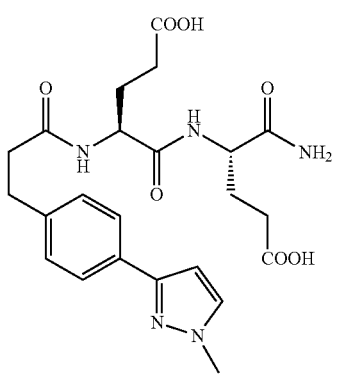
Formula (34)
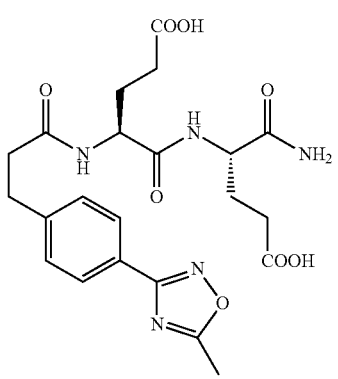
Formula (35)
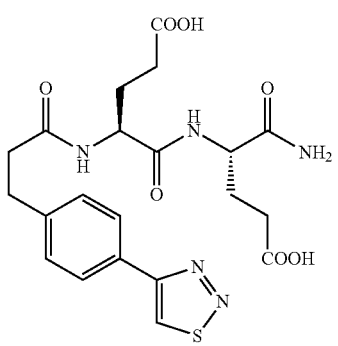
Formula (36)
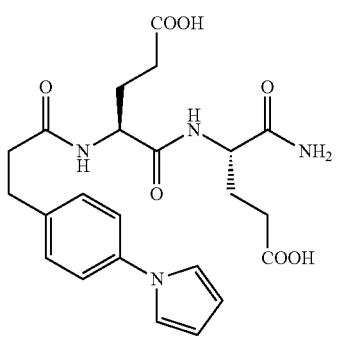
-continued
Formula (37)
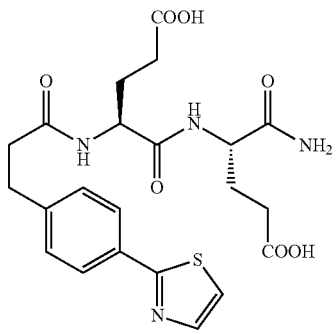
Formula (38)
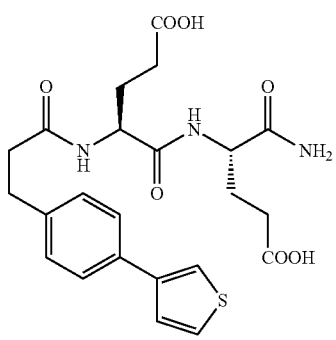
Formula (39)
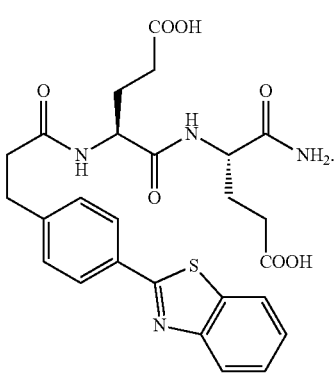
8. The compound of claim 1, having formula (1-D):
Formula (1-D)
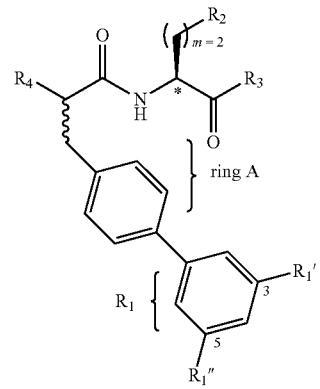
wherein:
$R_1$ is:
an unsubstituted phenyl group ($R_1'$=H and $R_1''$=H),
or a phenyl group monosubstituted in position 3 with an amino group ($R_1'$=NH$_2$, $R_1''$=H) or with a hydroxyl group ($R_1'$=OH, $R_1''$=H) or with a nitro group ($R_1'$=NO$_2$, $R_1''$=H) or with a carboxyl group ($R_1'$=COOH, $R_1''$=H) or with a chlorine atom ($R_1'$=C$_1$, $R_1''$=H) or with a methoxy group ($R_1'$=OMe, $R_1''$=H) or with a hydroxymethyl group ($R_1'$=CH$_2$OH, $R_1''$=H), or a phenyl group disubstituted in positions 3 and 5 with a chlorine atom ($R_1'$=Cl and $R_1''$=Cl), m is 2, $R_2$ is a carboxylic acid group, or a diastereoisomer of formula (1-D).

9. The compound of claim 8, having a formula selected from formulae (40) and (42) to (60):

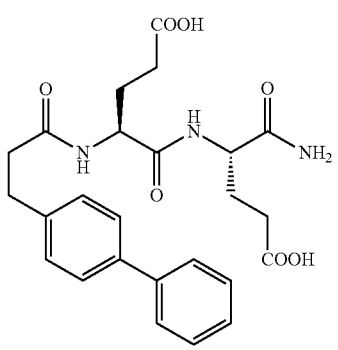

Formula (40)

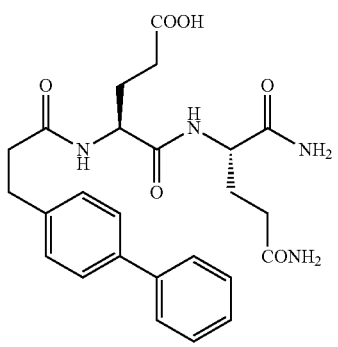

Formula (42)

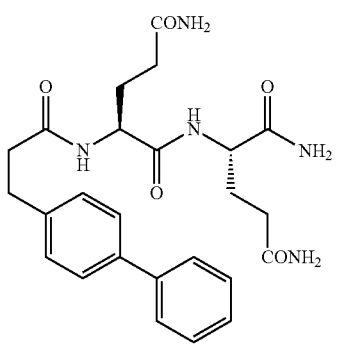

Formula (43)

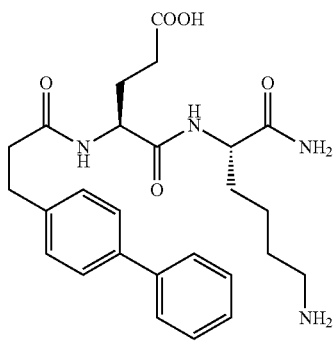

Formula (44)

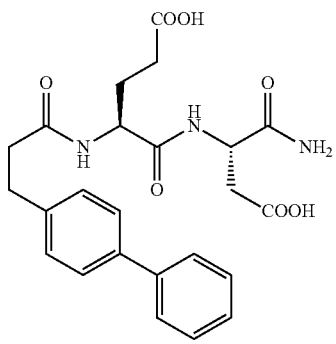

Formula (45)

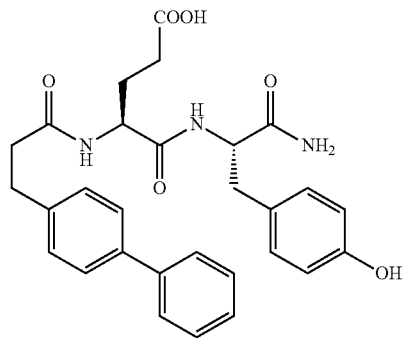

Formula (46)

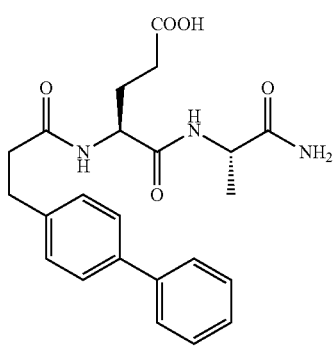

Formula (47)

Formula (48)
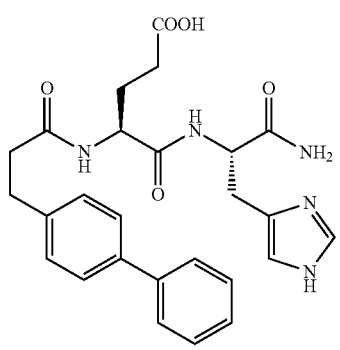
Formula (49)
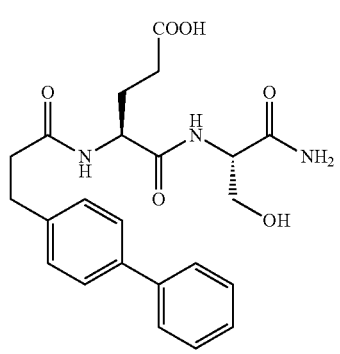
Formula (50)
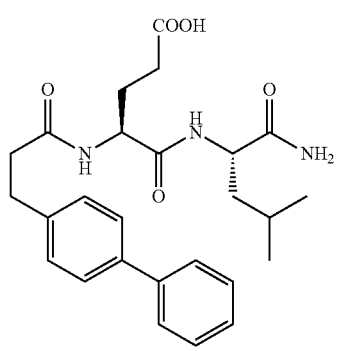
Formula (51)
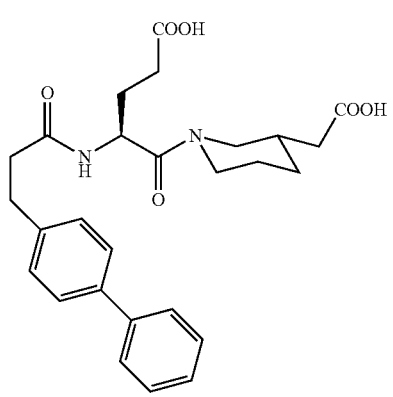
Formula (52)
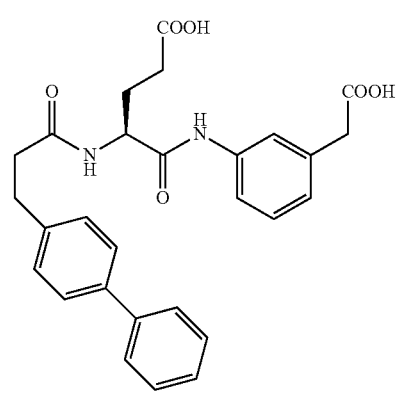
Formula (53)
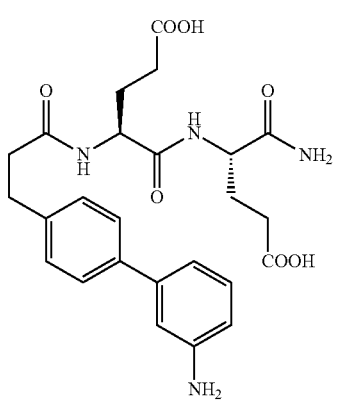
Formula (54)
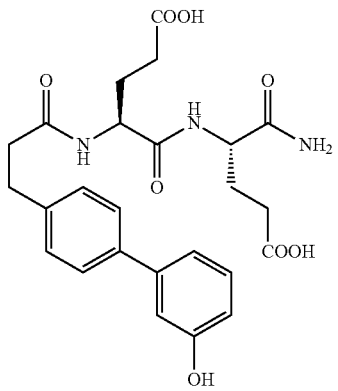
Formula (55)
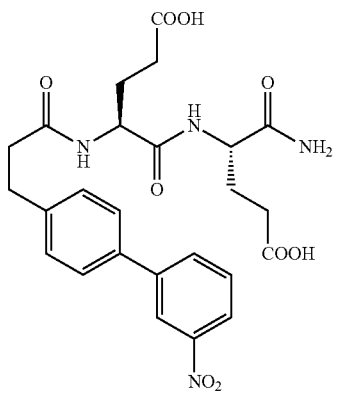

Formula (56)
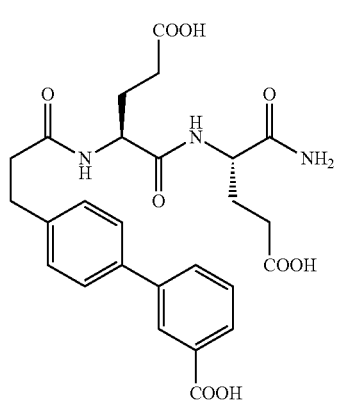
Formula (57)
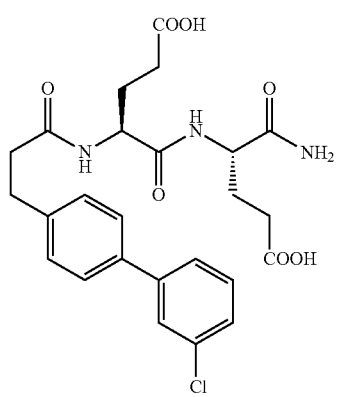
Formula (58)
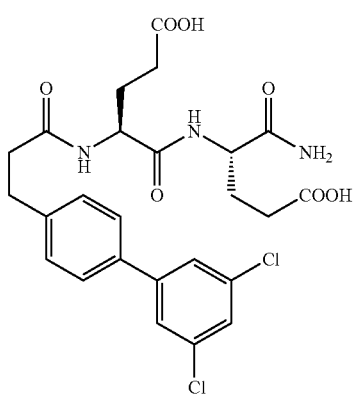
Formula (59)
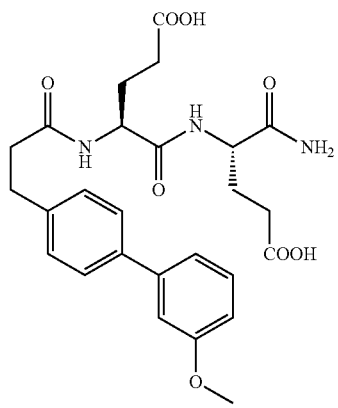
Formula (60)
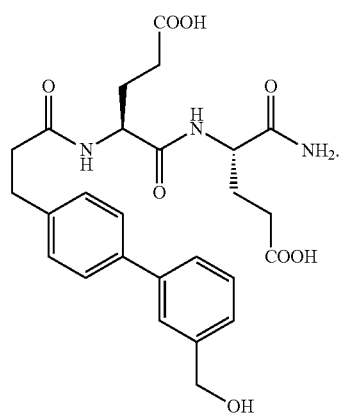
10. The compound of claim 1, having formula (1-E):
Formula (1-E)
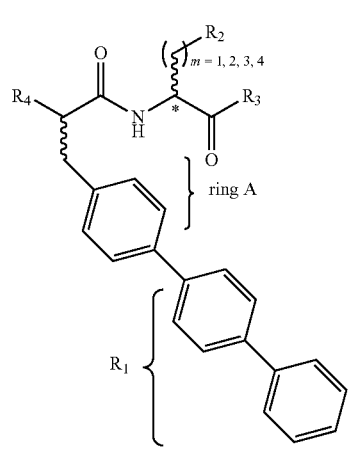
wherein:
$R_1$ is a biphenyl group,
m is 1, 2, 3 or 4,
or a diastereoisomer or enantiomer of formula (1-E).
11. The compound of claim 10, having a formula selected from formulae (61) to (79):
Formula (61)
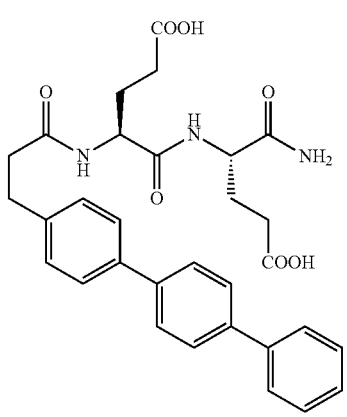

Formula (62)
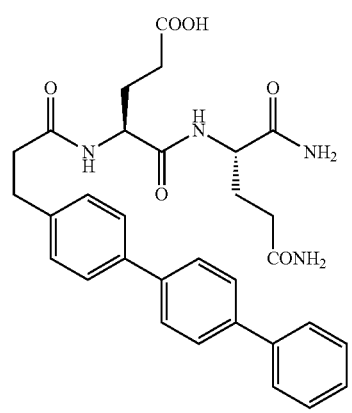
Formula (63)
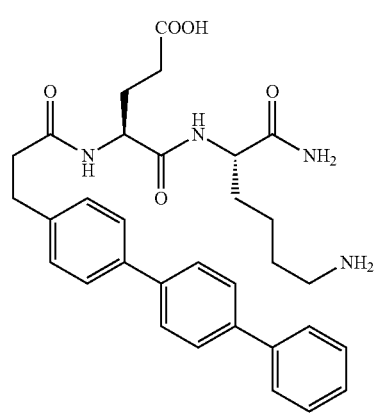
Formula (64)
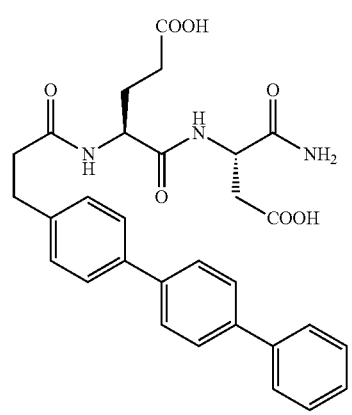
Formula (65)
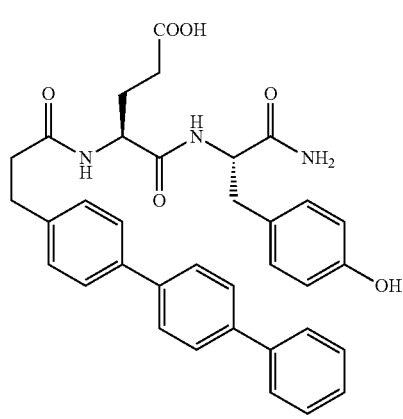
Formula (66)
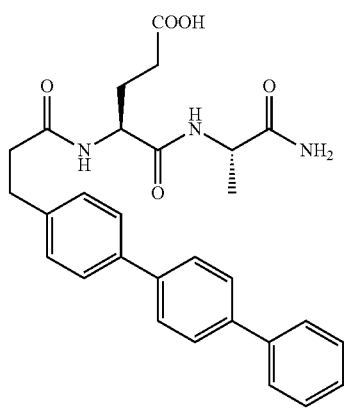
Formula (67)
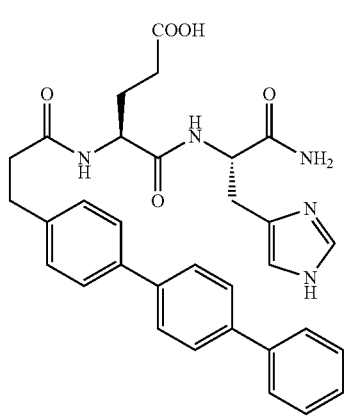
Formula (68)
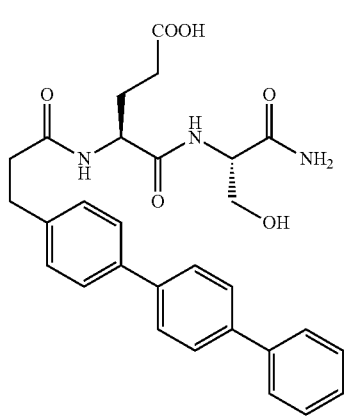
Formula (69)
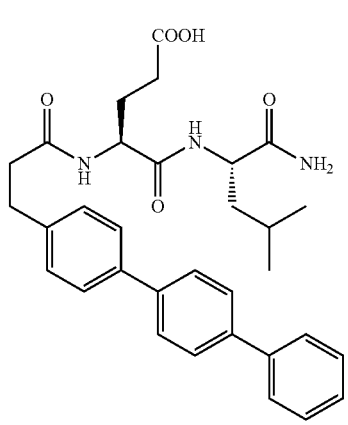

Formula (70)
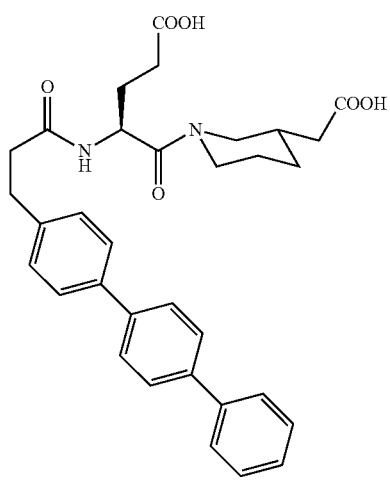
Formula (71)
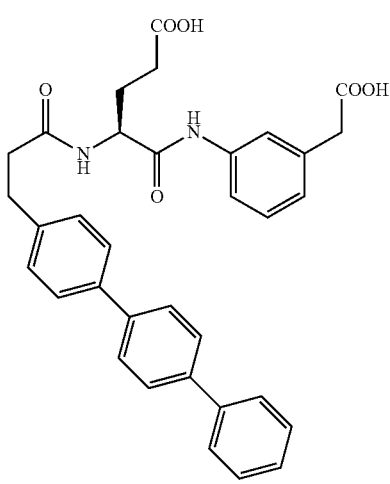
Formula (72)
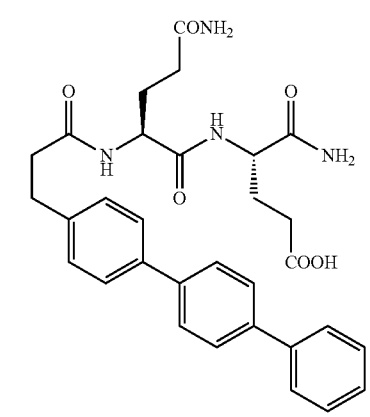
Formula (73)
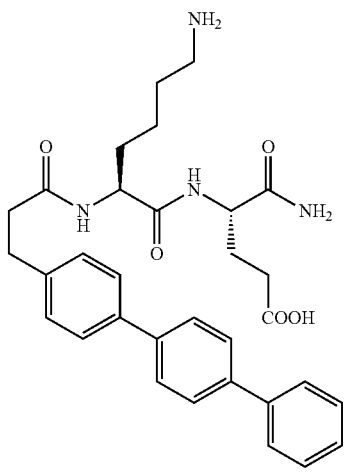
Formula (74)
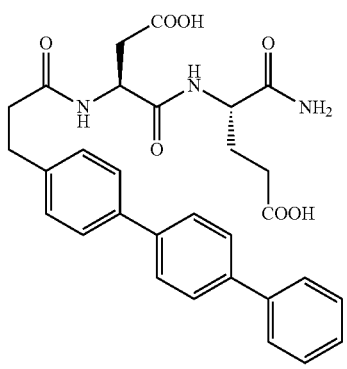
Formula (75)
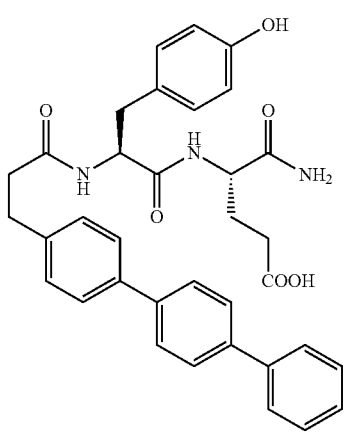
Formula (76)
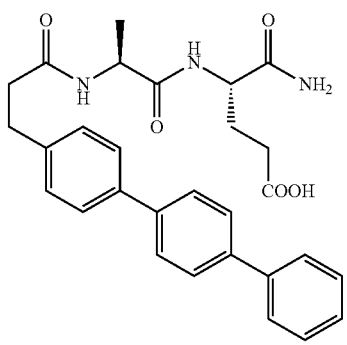

-continued

Formula (77)
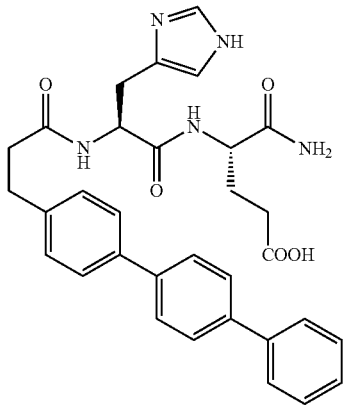

Formula (78)
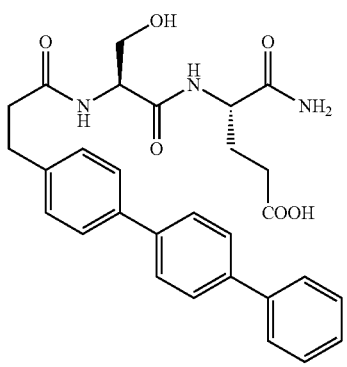

Formula (79)
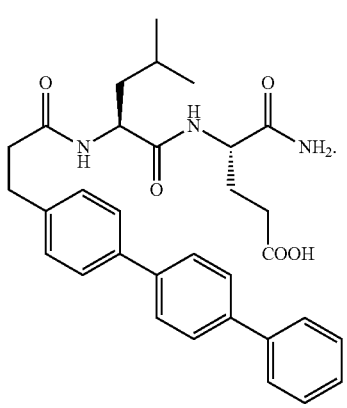

12. The compound of claim 1, having formula (1-F):

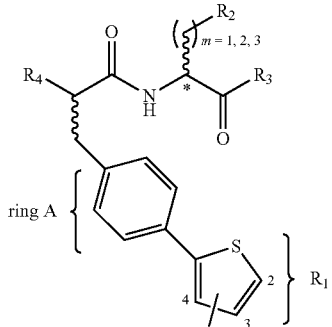

Formula (1-F)

wherein:

$R_1$ is an unsubstituted thiophene ring ($R_1''' =H$), or a thiophene ring monosubstituted either in position 2 with a group chosen from a methyl ($R_1'''=CH_3$) or phenyl ($R_1'''=Ph$) or 3a,7a-dihydrobenzo[d]thiazole group, or in position 3 with a group chosen from a methyl ($R_1'''=CH_3$) or phenyl ($R_1'''=Ph$) group, or in position 4 with a methyl group ($R_1'''=CH_3$), m=1, 2 or 3, and $R_2$ is a carboxylic acid group or an imidazole group when m=1, or a carboxylic acid group or a carboxamide group when m=2, or a carboxylic acid group when m=3, or a diastereoisomer or enantiomer of formula (1-F).

13. The compound of claim 12, having a formula selected from formulae (80) to (107):

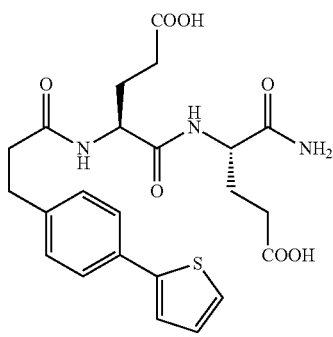

Formula (80)

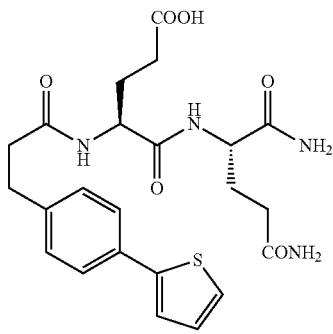

Formula (81)

Formula (82)
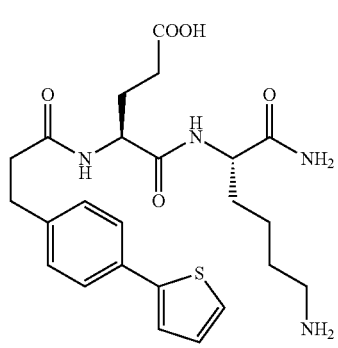
Formula (83)
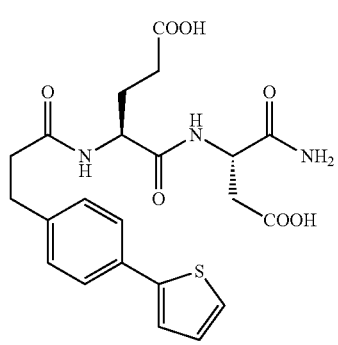
Formula (84)
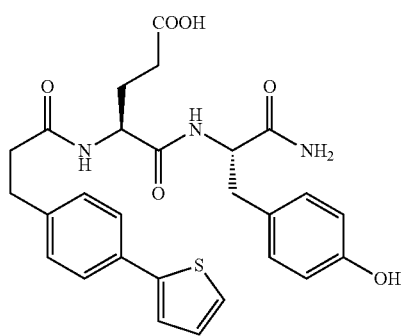
Formula (85)
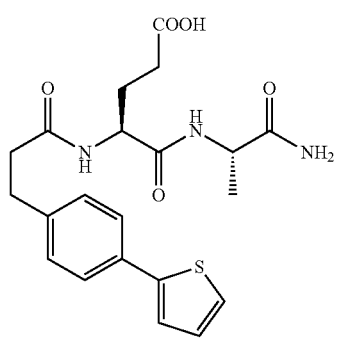
Formula (86)
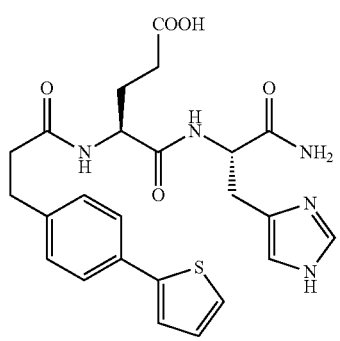
Formula (87)
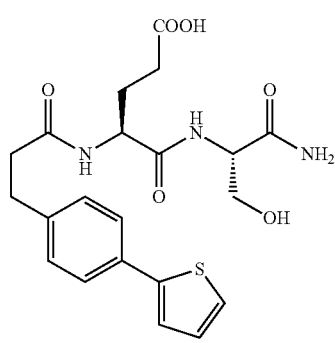
Formula (88)
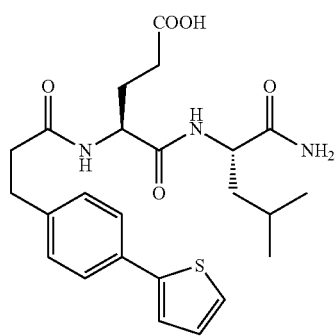
Formula (89)
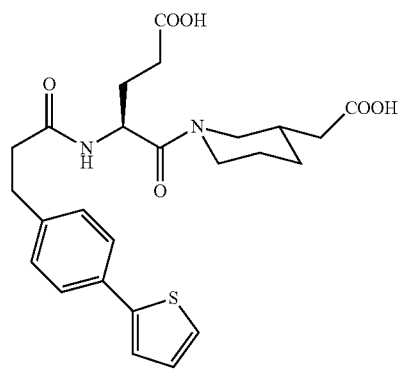

Formula (90)
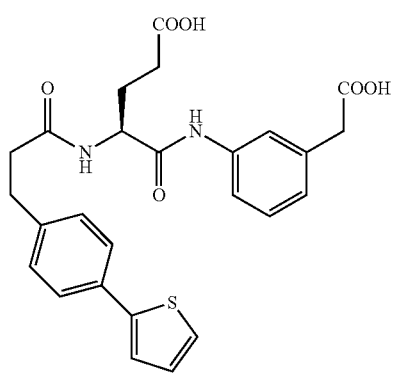
Formula (91)
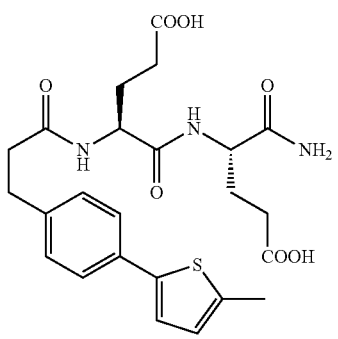
Formula (92)
Formula (93)
Formula (94)
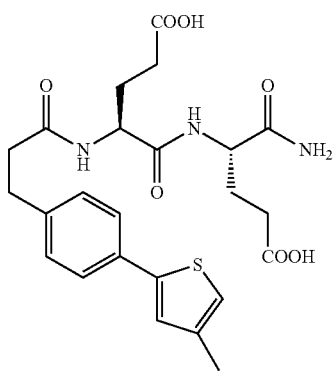
Formula (95)
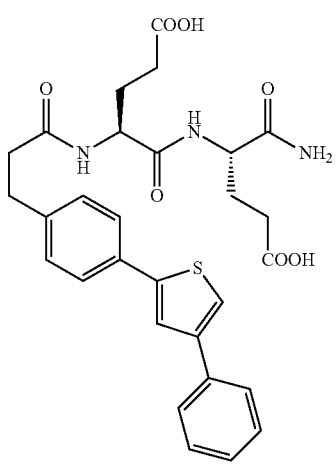
Formula (96)
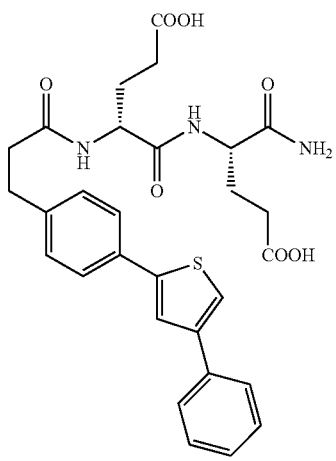

Formula (97)
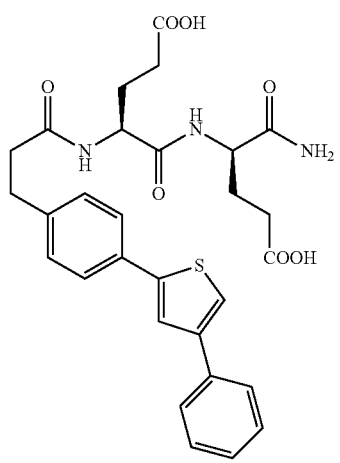
Formula (98)
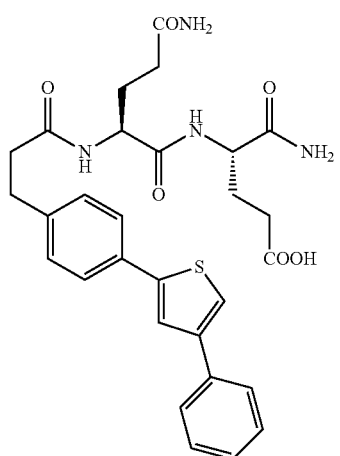
Formula (99)
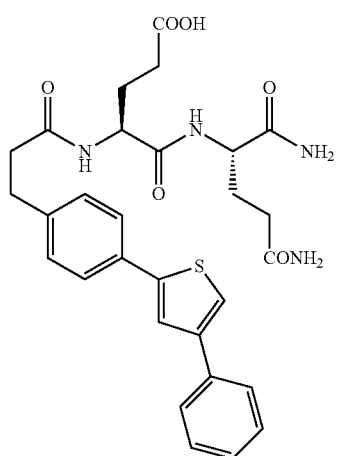
Formula (100)
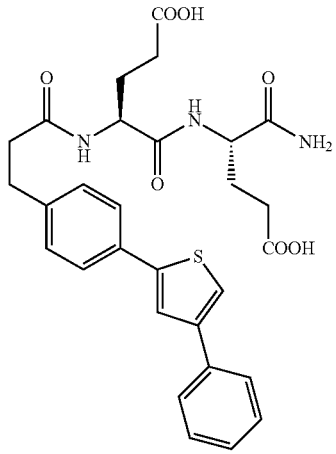
Formula (101)
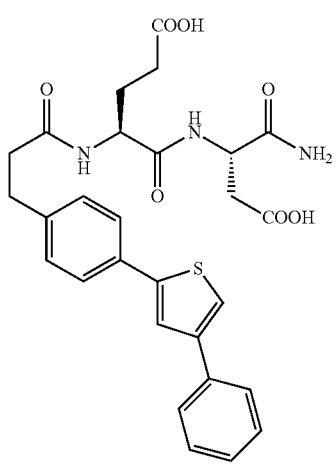
Formula (102)
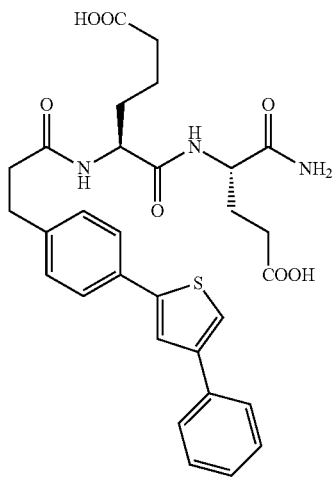

Formula (103)
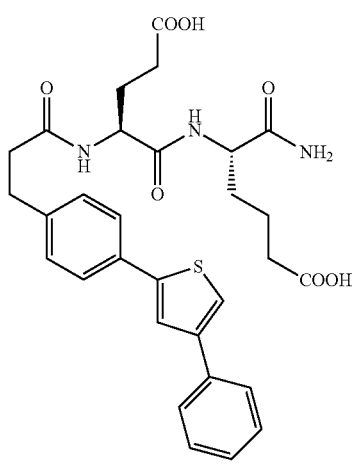
Formula (104)
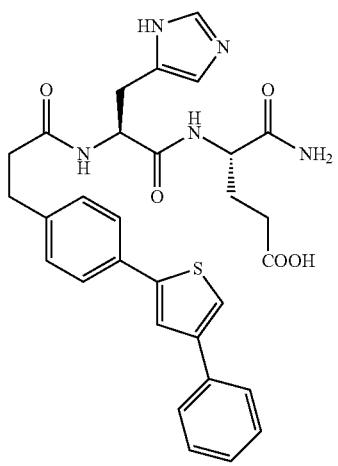
Formula (105)
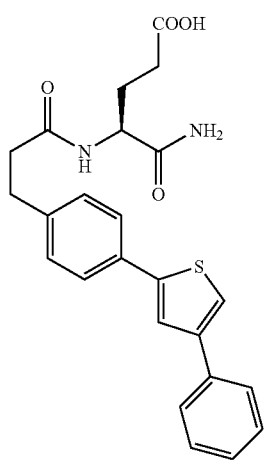
Formula (106)
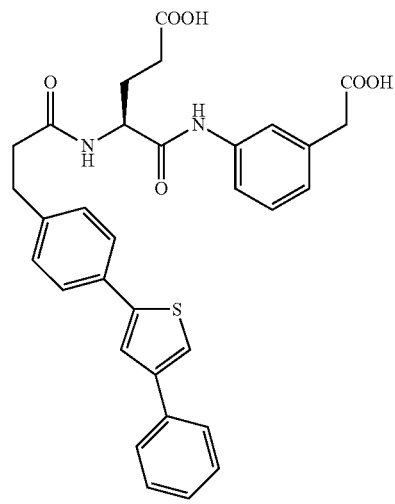
Formula (107)
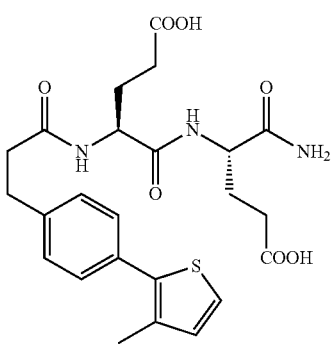
Formula (95bis)
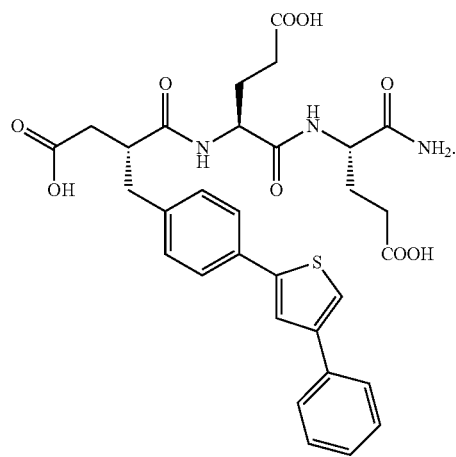

14. The compound of claim 12, having formula (1-F1):
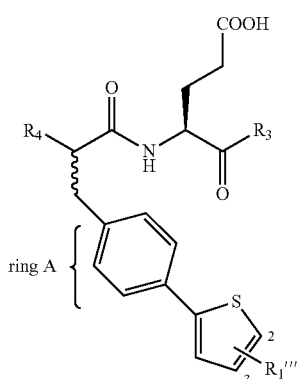
Formula (1-F1)
wherein:
$R_1'''$ is in position 2 or in position 3 of the thiophene ring and is a methyl ($R_1'''$=CH$_3$) or phenyl ($R_1'''$=Ph) group,
or a diastereoisomer or enantiomer of formula (1-F1).
15. The compound of claim 14, having formula (91), (92), (95), (97), (99), (101), (103), (105), (106) or (95bis):
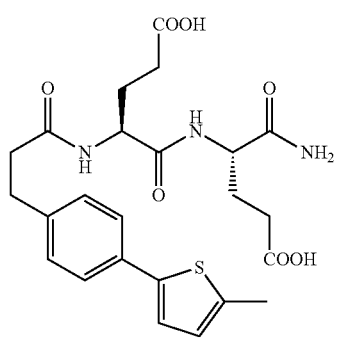
Formula (91)
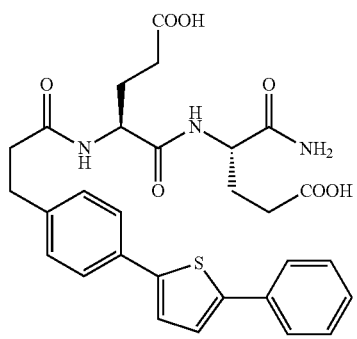
Formula (92)
-continued
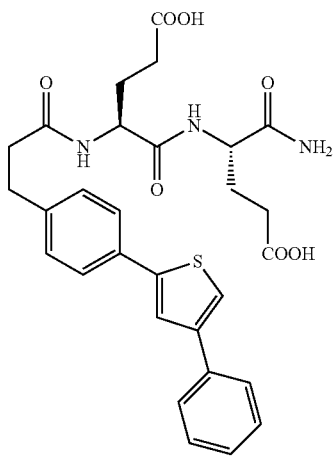
Formula (95)
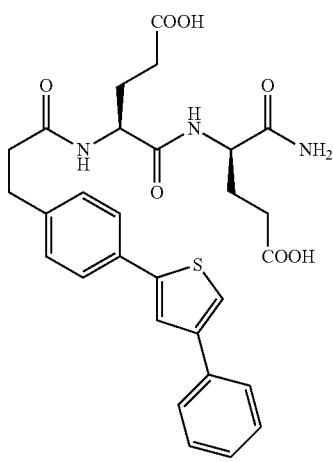
Formula (97)
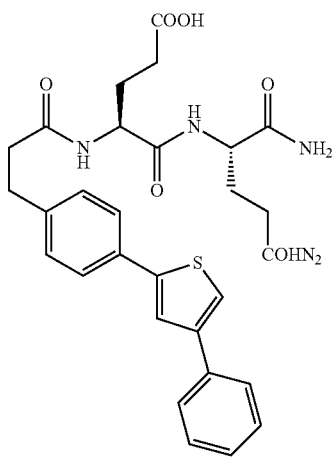
Formula (99)

Formula (101)
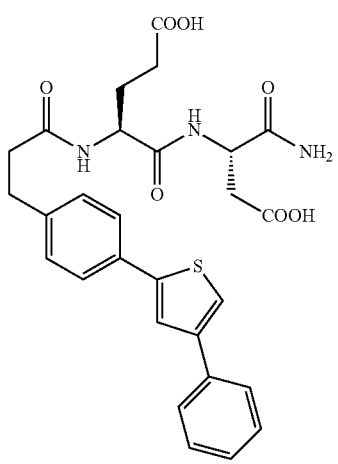
Formula (103)
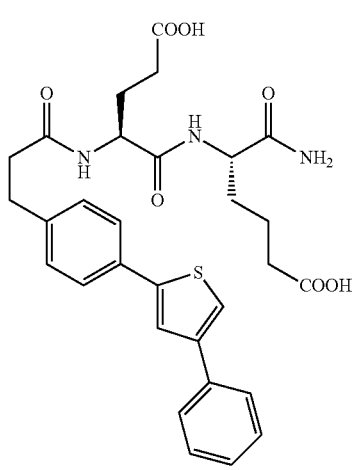
Formula (105)
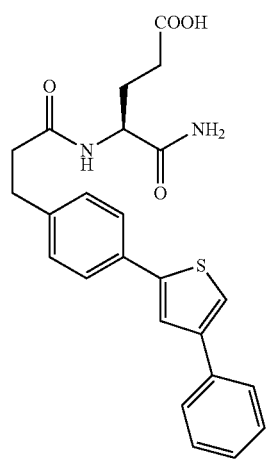
Formula (106)
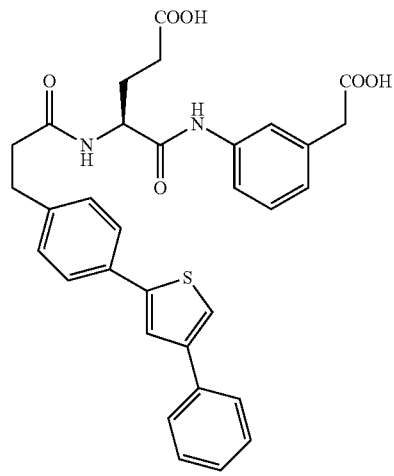
Formula (95bis)
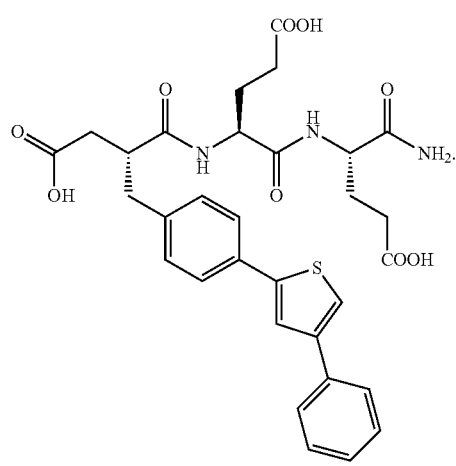
16. The compound of claim 14, having formula (1-F2):
Formula (1-F2)
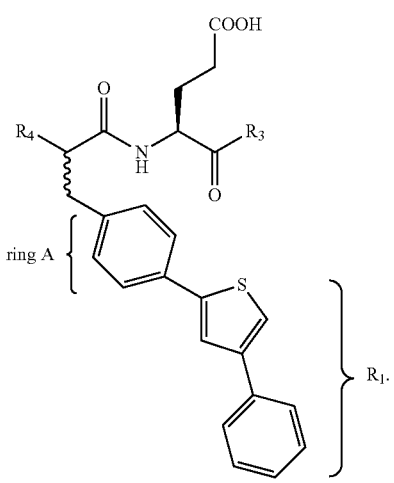
17. The compound of claim 16, having formula (95), (97), (99), (101), (103), (105), (106) or (95bis):

233 234
-continued
Formula (95)
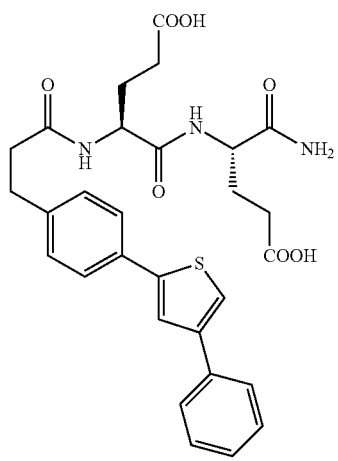
Formula (101)
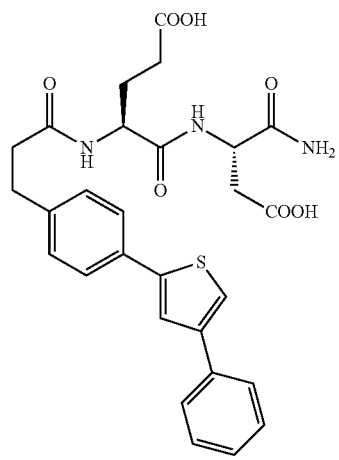
Formula (97)
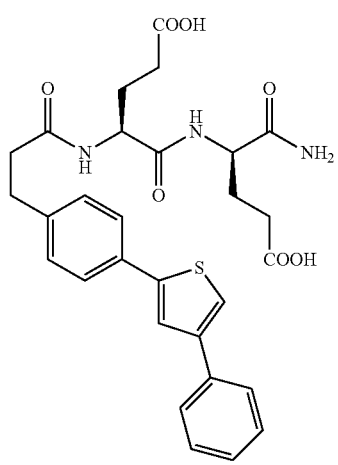
Formula (103)
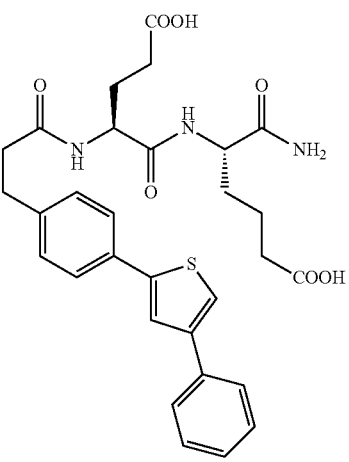
Formula (99)
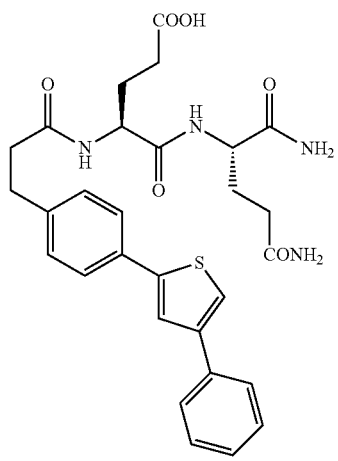
Formula (105)
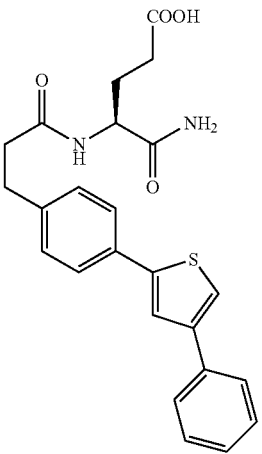

Formula (106)

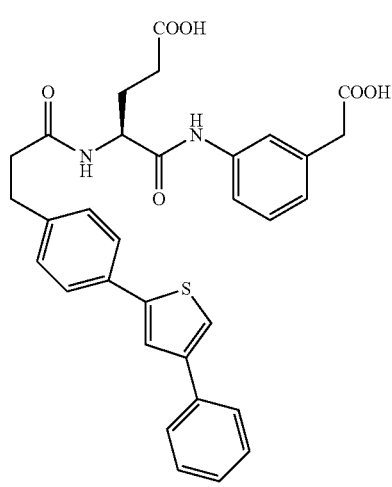

Formula (95bis)

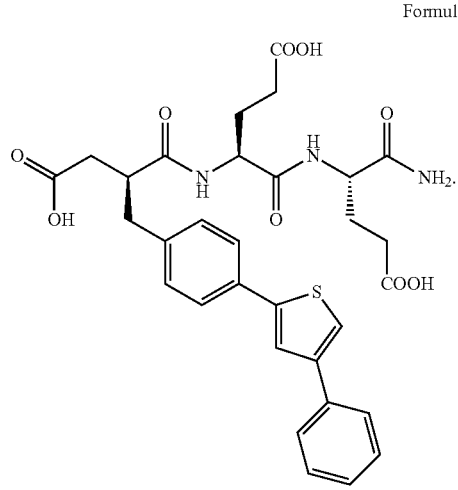

18. The compound of claim 1, wherein R₄ is H.

19. The compound of claim 1, suitable for use as a medicament.

20. The compound of claim 1, suitable for use as an extracellular matrix metalloproteinase inhibitor.

21. The compound of claim 15, suitable for use as an extracellular matrix metalloproteinase 12, MMP-12, inhibitor.

22. A pharmaceutical composition comprising the compound of claim 1 and a pharmaceutically acceptable excipient.

23. The compound of claim 1, suitable for use as a medicament for treating, inflammatory diseases, chronic obstructive pulmonary disease (COPD), arthritis, rhumatoid arthritis, atherosclerosis, or a ruptured aneurysm.

24. A compound of formula (2):

Formula (2)

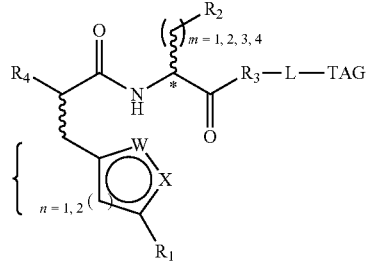

wherein:

n is 1 or 2, when n is 1, W and X each independently are O, N or C, when n is 2, W and X are C, $R_1$ is selected from the group consisting of an iodine atom, phenyl, biphenyl, 3'-chlorobiphenyl, phenoxy, phenoxymethyl, phenylethynyl, pyrimidine, 1-methyl-1H-pyrazole, 5-methyl-1,2,4-oxadiazole, 1,2,3-thiadiazole, 1H-pyrrole, thiazole, thiophene, 3a,7a-dihydrobenzo[d]thiazole, 3-aminophenyl, 3-hydroxyphenyl, 3-nitrophenyl, 3-carboxyphenyl, 3'-chlorophenyl, 3,5-dichlorophenyl, 3-methoxyphenyl, 3-hydroxymethylphenyl, and a thiophene ring substituted in at least one position selected from 2, 3, 4, and 5 with a group selected independently for each position from methyl, phenyl, and 3a,7a-dihydrobenzo[d]thiazole, wherein:

m is an integer of 1 to 4, when m is 4, $R_2$ is an amino group, when m is 3, $R_2$ is a carboxylic acid group, when m is 2, $R_2$ is a carboxamide group or a carboxylic acid group, when m is 1, $R_2$ is a carboxylic acid group, a 4-hydroxyphenyl group, a 1H-imidazole group, a hydroxyl group, an isopropyl group, or a methyl group, $R_3$ is an amino group; a carboxymethylpiperidine group; a carboxymethyl-3-aminophenyl group; or a residue selected from the group consisting of a glutamate residue of L or D configuration, a homoglutamate residue, an aspartate residue, a glutamine residue, an alanine residue, a lysine residue, a tyrosine residue, a histidine residue, a serine residue, and a leucine residue, optionally wherein a terminal carboxylic group of the residue is a carboxamide group —C(=O)NH₂, and $R_3$ is bonded via an amino group, $R_4$ is H or a carboxymethyl group —CH₂COOH, L is a spacer arm selected from a $C_1$-$C_{12}$ alkyl chain and a glycol ether wherein a carbon-based chain has 2 to 12 carbon atoms, and TAG is a label, $R_3$ being bonded to the spacer arm L via a terminal carboxamide group —C(=O)NH₂.

25. The compound of claim 24, suitable for use as a contrast agent for detecting an extracellular matrix metalloproteinase, or for detecting macrophage elastase or MMP-12.

\* \* \* \* \*